US008354237B2

(12) United States Patent
Rincon et al.

(10) Patent No.: US 8,354,237 B2
(45) Date of Patent: Jan. 15, 2013

(54) ANTI-METHYLATION-CONTROLLED J PROTEIN ANTIBODIES AND USES THEREOF

(75) Inventors: Mercedes Rincon, Burlington, VT (US); Wendy Neveu, Winooski, VT (US)

(73) Assignee: University of Vermont and State Agriculture College, Burlington, VT (US)

( * ) Notice: Subject to any disclaimer, the term of this patent is extended or adjusted under 35 U.S.C. 154(b) by 247 days.

(21) Appl. No.: 12/449,265

(22) PCT Filed: Feb. 1, 2008

(86) PCT No.: PCT/US2008/001357
§ 371 (c)(1),
(2), (4) Date: Jan. 27, 2010

(87) PCT Pub. No.: WO2008/097467
PCT Pub. Date: Aug. 14, 2008

(65) Prior Publication Data
US 2010/0129931 A1 May 27, 2010

Related U.S. Application Data

(60) Provisional application No. 60/899,093, filed on Feb. 2, 2007.

(51) Int. Cl.
*G01N 33/53* (2006.01)
(52) U.S. Cl. ...... 435/7.1; 435/320.1; 435/325; 435/326; 435/331; 435/332; 536/23.5; 436/501; 530/328; 530/350; 530/387.1; 530/387.3; 530/387.9; 530/388.2; 530/389.1
(58) Field of Classification Search .................. 530/350, 530/387.1, 387.3, 387.9, 388.2, 328, 389.1; 435/320.1, 325, 326, 331, 332, 7.1; 536/23.5; 436/501
See application file for complete search history.

(56) References Cited

U.S. PATENT DOCUMENTS
6,222,029 B1 * 4/2001 Edwards et al. ............. 536/24.1

FOREIGN PATENT DOCUMENTS
WO   WO-2006/068440 A1   6/2006

OTHER PUBLICATIONS

Shridhar et al. (Cancer Res. May 15, 2001; 61 (10): 4258-65).*
Campbell (Monoclonal Antibody Technology, Laboratory Techniques in Biochemistry and Molecular Biology, 1984, Elsevier Science Publishers B.V.: Amsterdam, The Netherlands, vol. 13, pp. 1-32).*
George et al. (Circulation. 1998; 97: 900-906).*
Rudikoff et al (Proc. Natl. Acad. Sci. USA. 1982; 79: 1979-1983).*
Mariuzza et al. (Annu. Rev. Biophys. Biophys. Chem. 1987; 16: 139-159).*
Gussow et al. (Methods in Enzymology. 1991; 203: 99-121).*
Winkler et al. (J. Immunol. Oct. 15, 2000; 165 (8): 4505-4514).*
Giusti et al. (Proc. Natl. Acad. Sci. USA. May 1987; 84 (9): 2926-2930).*
Chien et al. (Proc. Natl. Acad. Sci. USA. Jul. 1989; 86 (14): 5532-5536).*
Caldas et al. (Mol. Immunol. May 2003; 39 (15): 941-952).*
Vajdos et al. (J. Mol. Biol. Jul. 5, 2002; 320 (2): 415-428).*
De Pascalis et al. (J. Immunol. 2002; 169 (6): 3076-3084).*
Wu et al. (J. Mol. Biol. Nov. 19, 1999; 294 (1): 151-162).*
Casset et al. (Biochem. Biophys. Res. Commun. Jul. 18, 2003; 307 (1): 198-205).*
MacCallum et al. (J. Mol. Biol. Oct. 11, 1996; 262 (5): 732-745).*
Holm et al. (Mol. Immunol. Feb. 2007; 44 (6): 1075-1084).*
Alley et al., Feasibility of drug screening with panels of human tumor cell lines using a microculture tetrazolium assay. Cancer Res. Feb. 1, 1988;48(3):589-601.
Angel et al., Phorbol ester-inducible genes contain a common cis element recognized by a TPA-modulated trans-acting factor. Cell. Jun. 19, 1987;49(6):729-39.
Baerga-Ortiz et al., Epitope mapping of a monoclonal antibody against human thrombin by H/D-exchange mass spectrometry reveals selection of a diverse sequence in a highly conserved protein. Protein Sci. Jun. 2002;11(6):1300-8.
Bird, Single-chain antigen-binding proteins. Science. Oct. 21, 1988;242(4877):423-6. Erratum in: Science Apr. 28, 1989;244(4903):409.
Brummelkamp et al., A system for stable expression of short interfering RNAs in mammalian cells. Science. Apr. 19, 2002;296(5567):550-3. Epub Mar. 21, 2002.
Chen et al., Characterization of adriamycin-resistant human breast cancer cells which display overexpression of a novel resistance-related membrane protein. J Biol Chem. Jun. 15, 1990;265(17):10073-80.
Chen et al., In situ biochemical demonstration that P-glycoprotein is a drug efflux pump with broad specificity. J Cell Biol. Mar. 6, 2000;148(5):863-70.
Comerford et al., Hypoxia-inducible factor-1-dependent regulation of the multidrug resistance (MDR1) gene. Cancer Res. Jun. 15, 2002;62(12):3387-94.
Conze et al., Autocrine production of interleukin 6 causes multidrug resistance in breast cancer cells. Cancer Res. Dec. 15, 2001;61(24):8851-8.
Craig et al., The diverse roles of J-proteins, the obligate Hsp70 co-chaperone. Rev Physiol Biochem Pharmacol. 2006;156:1-21. Review.
Doyle et al., Multidrug resistance mediated by the breast cancer resistance protein BCRP (ABCG2). Oncogene. Oct. 20, 2003;22(47):7340-58.
Dérijard et al., JNK1: a protein kinase stimulated by UV light and Ha-Ras that binds and phosphorylates the c-Jun activation domain. Cell. Mar. 25, 1994;76(6):1025-37.

(Continued)

*Primary Examiner* — Stephen Rawlings
(74) *Attorney, Agent, or Firm* — Finch & Maloney PLLC

(57) ABSTRACT

This application includes, in part, methods of preparing antibodies that specifically bind to methylation-controlling J (MCJ) polypeptide. In some aspects, the application also includes, hybridoma cell lines that produce antibodies that specifically MCJ polypeptide; antibodies and antigen-binding fragments thereof produced with the methods of the application, and methods of using antibodies and antigen-binding fragments that specifically bind MCJ polypeptide for diagnosis and treatment of cancer.

20 Claims, 9 Drawing Sheets

OTHER PUBLICATIONS

Diah et al., Resistance to mitoxantrone in multidrug-resistant MCF7 breast cancer cells: evaluation of mitoxantrone transport and the role of multidrug resistance protein family proteins. Cancer Res. Jul. 15, 2001;61(14):5461-7.

Ehrlich et al., Hypomethylation and hypermethylation of DNA in Wilms tumors. Oncogene. Sep. 26, 2002;21(43):6694-702.

Fairchild et al., Isolation of amplified and overexpressed DNA sequences from adriamycin-resistant human breast cancer cells. Cancer Res. Oct. 1, 1987;47(19):5141-8.

Fairchild et al., Multidrug resistance in cells transfected with human genes encoding a variant P-glycoprotein and glutathione S-transferase-pi. Mol Pharmacol. Jun. 1990;37(6):801-9.

Fang et al., Ubiquitin-mediated fluorescence complementation reveals that Jun ubiquitinated by Itch/AIP4 is localized to lysosomes. Proc Natl Acad Sci U S A. Oct. 12, 2004;101(41):147827. Epub Oct. 5, 2004.

Fuchs et al., Phosphorylation-dependent targeting of c-Jun ubiquitination by Jun N-kinase. Oncogene. Oct. 3, 1996;13(7):1531-5.

Gao et al., Jun turnover is controlled through JNK-dependent phosphorylation of the E3 ligase Itch. Science. Oct. 8, 2004;306(5694):271-5. Epub Sep. 9, 2004.

GENBANK Submission; NIH/NCBI, Accession No. AAD38506; Shridhar et al.; May 25, 2001, 2 pages.

GENBANK Submission; NIH/NCBI, Accession No. AF126743; Shridhar et al.; May 25, 2001,1 page.

Gottesman et al., Multidrug resistance in cancer: role of ATP-dependent transporters. Nat Rev Cancer. Jan. 2002;2(1):48-58.

Halazonetis et al., c-Jun dimerizes with itself and with c-Fos, forming complexes of different DNA binding affinities. Cell. Dec. 2, 1988;55(5):917-24.

Harker et al., Multidrug (pleiotropic) resistance in doxorubicin-selected variants of the human sarcoma cell line MES-SA. Cancer Res. Sep. 1985;45(9):4091-6.

Harbottle et al., Role of glutathione S-transferase P1, P-glycoprotein and multidrug resistance-associated protein 1 in acquired doxorubicin resistance. Int J Cancer. Jun. 15, 2001;92(6):777-83.

Hatle et al., Methylation-controlled J protein promotes c-Jun degradation to prevent ABCB1 transporter expression. Mol Cell Biol. Apr. 2007;27(8):2952-66. Epub Feb. 5, 2007.

Huston et al., Protein engineering of antibody binding sites: recovery of specific activity in an anti-digoxin single-chain Fv analogue produced in *Escherichia coli*. Proc Natl Acad Sci U S A. Aug. 1988;85(16):5879-83.

Izawa et al., Identification of MRJ, a DnaJ/Hsp40 family protein, as a keratin 8/18 filament regulatory protein. J Biol Chem. Nov. 3, 2000;275(44):34521-7.

Kawakami et al., Identification and purification of a human immunoglobulin-enhancer-binding protein (NF-kappa B) that activates transcription from a human immunodeficiency virus type 1 promoter in vitro. Proc Natl Acad Sci U S A. Jul. 1988;85(13):4700-4.

Klement et al., Differences in therapeutic indexes of combination metronomic chemotherapy and an anti-VEGFR-2 antibody in multidrug-resistant human breast cancer xenografts. Clin Cancer Res. Jan. 2002;8(1):221-32.

Köhler et al., Derivation of specific antibody-producing tissue culture and tumor lines by cell fusion. Eur J Immunol. Jul. 1976;6(7):511-9.

Landschulz et al., The DNA binding domain of the rat liver nuclear protein C/EBP is bipartite. Science. Mar. 31, 1989;243(4899):1681-8.

Lee et al., Purified transcription factor AP-1 interacts with TPA-inducible enhancer elements. Cell. Jun. 19, 1987;49(6):741-52.

Lee et al., Involvement of the molecular chaperone Ydj1 in the ubiquitin-dependent degradation of short-lived and abnormal proteins in *Saccharomyces cerevisiae*. Mol Cell Biol. Sep. 1996;16(9):4773-81.

Lindsey et al., Epigenetic inactivation of MCJ (DNAJD1) in malignant paediatric brain tumours. Int J Cancer. Jan. 15, 2006;118(2):346-52.

Longley et al., Molecular mechanisms of drug resistance. J Pathol. Jan. 2005;205(2):275-92.

Mechetner et al., Levels of multidrug resistance (MDR1) P-glycoprotein expression by human breast cancer correlate with in vitro resistance to taxol and doxorubicin. Clin Cancer Res. Feb. 1998;4(2):389-98.

Mokranjac et al., Tim14, a novel key component of the import motor of the TIM23 protein translocase of mitochondria. EMBO J. Oct. 1, 2003;22(19):4945-56.

Musti et al., Differential regulation of c-Jun and JunD by ubiquitin-dependent protein degradation. Biol Chem. Oct. 1996;377(10):619-24.

Musti et al., Reduced ubiquitin-dependent degradation of c-Jun after phosphorylation by MAP kinases. Science. Jan. 17, 1997;275(5298):400-2.

Nabhan et al., The 19 S proteasomal subunit POH1 contributes to the regulation of c-Jun ubiquitination, stability, and subcellular localization. J Biol Chem. Jun. 9, 2006;281(23):16099-107. Epub Mar. 28, 2006.

Nateri et al., The ubiquitin ligase SCFFbw7 antagonizes apoptotic JNK signaling. Science. Feb. 27, 2004;303(5662):1374-8. Epub Jan. 22, 2004.

Noonan et al., Quantitative analysis of MDR1(multidrug resistance) gene expression in human tumors by polymerase chain reaction. Proc Natl Acad Sci U S A. Sep. 1990;87(18):7160-4.

Rincon et al., Cancer and Leukemia Group B. Interleukin-6, multidrug resistance protein-1 expression and response to paclitaxel in women with metastatic breast cancer: results of cancer and leukemia group B trial 159806. Breast Cancer Res Treat. Dec. 2006;100(3):301-8. Epub Jun. 14, 2006.

Salceda et al., Hypoxia-inducible factor 1alpha (HIF-1alpha) protein is rapidly degraded by the ubiquitin-proteasome system under normoxic conditions. Its stabilization by hypoxia depends on redox-induced changes. J Biol Chem. Sep. 5, 1997;272(36):22642-7.

Scheufler et al., Structure of TPR domain-peptide complexes: critical elements in the assembly of the Hsp70-Hsp90 multichaperone machine. Cell. Apr. 14, 2000;101(2):199-210.

Scotto, Transcriptional regulation of ABC drug transporters. Oncogene. Oct. 20, 2003;22(47):7496-511. Review.

Shridhar et al., Loss of expression of a new member of the DNAJ protein family confers resistance to chemotherapeutic agents used in the treatment of ovarian cancer. Cancer Res. May 15, 2001;61(10):4258-65.

Sladowski et al., An improved MTT assay. J Immunol Methods. Jan. 4, 1993;157(1-2):203-7.

Sondermann et al., Structure of a Bag/Hsc70 complex: convergent functional evolution of Hsp70 nucleotide exchange factors. Science. Feb. 23, 2001;291(5508):1553-7.

Strathdee et al., Cell type-specific methylation of an intronic CpG island controls expression of the MCJ gene. Carcinogenesis. May 2004;25(5):693-701. Epub Jan. 16, 2004.

Strathdee et al., Demethylation of the MCJ gene in stage III/IV epithelial ovarian cancer and response to chemotherapy. Gynecol Oncol. Jun. 2005;97(3):898-903.

Treier et al., Ubiquitin-dependent c-Jun degradation in vivo is mediated by the delta domain. Cell. Sep. 9, 1994;78(5):787-98.

Ungewickell et al., Role of auxilin in uncoating clathrin-coated vesicles. Nature. Dec. 7, 1995;378(6557):632-5.

Wahl et al., Improved radioimaging and tumor localization with monoclonal F(ab')2. J Nucl Med. Apr. 1983;24(4):316-25.

Young et al., More than folding: localized functions of cytosolic chaperones. Trends Biochem Sci. Oct. 2003;28(10):541-7.

Zhu et al., COOH-terminal Src kinase-mediated c-Jun phosphorylation promotes c-Jun degradation and inhibits cell transformation. Cancer Res. Jun. 1, 2006;66(11):5729-36.

\* cited by examiner

ANTI-METHYLATION-CONTROLLED J PROTEIN ANTIBODIES AND USES THEREOF

RELATED APPLICATIONS

This application is a national stage filing under U.S.C. §371 of PCT International application PCT/US2008/001357, filed Feb. 1, 2008, which was published under PCT Article 21(2) in English, and claims the benefit under 35 U.S.C. §119(e) of U.S. provisional application Ser. No. 60/899,093, filed Feb. 2, 2007, the content of each referenced application is incorporated by reference herein in its entirety.

FIELD OF THE INVENTION

This invention relates generally to preparation and use of antibodies and/or antigen-binding fragments thereof that specifically recognize and bind to an epitope at the C terminus of methylation-controlled J (MCJ) polypeptide. Aspects of the invention also relate, in part, to monoclonal and polyclonal antibodies or antigen-binding fragments thereof that bind specifically to an epitope at the C terminus of MCJ polypeptide and the use of such antibodies or antigen binding fragments thereof for cancer diagnostics, therapeutics, and research methods and compositions.

BACKGROUND OF THE INVENTION

MCJ is a recently identified member of the DnaJ protein family of co-chaperones and its expression is controlled by methylation (Shridhar et al., *Cancer Res* 61, 4258-4265, 2001). DnaJ polypeptides are characterized by the presence of the DnaJ domain containing the His-Pro-Asp signature tripeptide. The DnaJ protein family is one of the largest co-chaperone families that has members with diverse cellular localization and functions (reviewed by Craig et al., *Rev Physiol Biochem Pharmacol* 156, 1-21, 2006). In addition to the DnaJ family, two other families of co-chaperones have been identified based on the presence of the Bag domain (Sondermann et al., *Science* 291, 1553-1557, 2001) or the tetratricopeptide repeat (TRP) clamp domain (Scheufler et al., *Cell* 101, 199-210, 2000; Sonderinann et al., *Science* 291, 1553-1557, 2001)). Co-chaperones associate with the heat shock protein (Hsp) 70 (Hsp90, Hsp70, Hsc70) family of chaperones through these conserved domains and participate in protein folding and trafficking (reviewed by Young et al., *Trends Biochem Sci* 28, 541-547, 2003). Co-chaperones have a modular architecture in which a chaperone-binding domain (DnaJ, TRP or Bag) is fused to other non-conserved sequences that can interact with specific proteins and mediate a variety of diverse activities including clathrin uncoating (Ungewickell et al., *Nature* 378, 632-635, 1995) and cytoskeletal function (Izawa et al., *J Biol Chem* 275, 34521-34527, 2000). Some DnaJ co-chaperones also participate in ubiquitin dependent proteolysis either by tagging certain substrates for degradation or by facilitating the unfolding of folded proteins thus allowing degradation by proteolysis (Lee et al., *Mol Cell Biol* 16, 4773-4781, 1996).

MCJ has some unique features among the members of the DnaJ family. It is a rather small polypeptide of 150 aa (16-17 kDa) as compared to other members (~40 kDa). The DnaJ domain is located in the C-terminus (Shridhar et al., *Cancer Res* 61, 4258-4265, 2001), while it is commonly present in the N-terminus in other DnaJ proteins. In addition, a potential transmembrane domain distinguishes MCJ from most other DnaJ proteins that are present in the cytosol and interact with chaperones through the DnaJ domain. Thus, MCJ appears to be an atypical DnaJ family member.

MCJ was identified as a gene expressed in normal ovarian epithelial cells, but absent or expressed at very low levels in a number of primary ovarian tumors and ovarian carcinoma cell lines (Shridhar et al., *Cancer Res* 61, 4258-4265, 2001). Loss of MCJ was correlated with increased drug resistance in ovarian cancer cell lines (Shridhar et al., *Cancer Res* 61, 4258-4265, 2001). Hypermethylation of a CpG island present within the first exon and first intron of the MCJ gene represses MCJ expression (Strathdee et al., *Carcinogenesis* 25, 693-701, 2004). Overexpression of MCJ in ovarian cancer cells increases sensitivity to anti-neoplastic drugs in vitro (Shridhar et al., *Cancer Res* 61, 4258-4265, 2001). A recent study in ovarian cancer patients demonstrates that the high levels of CpG island methylation correlates with poor response of these tumors to chemotherapy and overall poor survival (Strathdee et al., *Gynecologic Oncology* 97, 898-903, 2005). Methylation of the MCJ gene has also been reported in some malignant pediatric brain tumors and in 90% of Wilms tumors, whereas very low levels of methylation has been found in normal tissues (Ehrlich et al., *Oncogene* 21, 6694-6702, 2002; Lindsey et al., *Int J Cancer.* 2006 Jan. 15; 118(2):346-52, 2005). However, the relevance of MCJ gene hypermethylation for chemoresistance in these tumors has not yet been addressed.

Although regulation of MCJ gene expression has received certain amount of interest, no information about the biology and function of the MCJ protein, including its cellular localization, is currently available. In addition, although the loss of MCJ gene expression by hypermethylation has been correlated with multidrug resistance in ovarian cancer, the mechanism by which this co-chaperone regulates the drug response is completely unknown.

SUMMARY OF THE INVENTION

The present invention relates, in part, to methods and compositions for making and using high-affinity antibodies that specifically bind to an epitope on methylation-controlled J protein (MCJ). The invention, in some aspects, includes the use of antibodies and antigen-binding fragments thereof that specifically bind a full-length MCJ polypeptide, or a polypeptide that is a fragment of full-length MCJ polypeptide, for diagnosis and/or treatment of cancer as well as methods and compositions for identifying and screening for compounds useful for the diagnosis and/or treatment of cancer.

The discovery of antibodies that specifically bind to an epitope of MCJ polypeptide facilitates analysis of diseases such as cancers, in which the amount of MCJ polypeptide differs from normal levels. For example, it has been discovered that a decrease in the level of MCJ polypeptide in cancer cells may lead to an increase in therapeutic drug resistance of the cancer cells. Thus, levels of expression of MCJ polypeptide may serve as a marker for drug resistance in a cancer and may be used to predict efficacy of cancer drugs and treatments. Thus, the potential efficacy of a therapeutic regimen against cancer in a subject may be evaluated by monitoring levels of MCJ polypeptide in the subject and the effects of candidate agents and compounds for the treatment of cancer or for the modulation of drug resistance in cancer cells may be assessed by monitoring the level of MCJ polypeptide in a sample or subject.

The invention also includes, in some aspects, also includes methods and compositions for identifying compounds that may modulate MCJ levels in a cell, tissue, and/or subject.

According to one aspect of the invention, isolated antibodies or antigen-binding fragments thereof that bind specifically to methylation controlled J (MCJ) polypeptide are provided. In certain embodiments, the antibody specifically binds an epitope of MCJ polypeptide, the epitope includes the sequence set forth as MAARGVIAPVGESLRYAEYL (SEQ ID NO:2). In some embodiments, the antibody competitively inhibits binding of a WN.F3, WN.A12, and/or WN.E4 antibody to the MCJ polypeptide. In some embodiments, the MCJ polypeptide includes an epitope that includes the sequence set forth as MAARGVIAPVGESLRYAEYL (SEQ ID NO:2). In some embodiments, the antibody is a monoclonal antibody. In certain embodiments, the antibody is WN.F3, WN.A12 and WN.E4. In some embodiments, the antibody specifically binds the epitope with a binding affinity of about $1\times10^{-6}$, $1\times10^{-7}$, $1\times10^{-8}$, $1\times10^{-9}$M or less. In some embodiments, the antibody specifically binds the epitope with a binding affinity of about $1\times10^{-10}$M, $1\times10^{-11}$M or about $5\times10^{-10}$M or less. In some embodiments, the antibody is a polyclonal antibody. In certain embodiments, the antibody is OD-C-MCJ. In some embodiments, the antibody specifically binds an epitope that includes SEQ ID NO:2 with greater binding affinity than the binding affinity of WN.F3, WN.A12, or WN.E4 antibody for the epitope. In some embodiments, the antibody is a recombinant antibody. In certain embodiments, the antibody is a mouse antibody, a fully human antibody, a chimeric antibody, or a humanized antibody. In some embodiments, the antibody or antigen-binding fragment thereof is attached to a detectable label. In some embodiments, the detectable label is a fluorescent label, an enzyme label, a radioactive label, a nuclear magnetic resonance active label, a luminescent label, or a chromophore label. In some embodiments, the antibody or antigen-binding fragment thereof includes an MCJ peptide-binding CDR3 region or a functional variant thereof. In certain embodiments, the CDR3 region is of a monoclonal antibody produced by: i) hybridoma N-MCJ 3C1.3F3, which was deposited under ATCC no. #PTA-8135; ii) hybridoma cell line N-MCJ 3C1.5A12, which was deposited under ATCC no. #PTA-8133; or iii) hybridoma cell line N-MCJ 2A2.5E4, which was deposited under. ATCC no. #PTA-8134. In some embodiments, the antibody or antigen-binding fragment thereof further includes a CDR2 region or a functional variant thereof. In some embodiments, the antibody or antigen-binding fragment thereof further includes a CDR3 region or a functional variant thereof.

According to another aspect of the invention, nucleic acid molecules that encode an isolated antibody or antigen-binding fragment thereof of any of the embodiments of the foregoing aspect of the invention are provided.

According to yet another aspect of the invention, hybridomas that include any of the nucleic acid molecules of the foregoing aspect of the invention are provided. In certain embodiments, the hybridoma is N-MCJ 3C1.3F3, N-MCJ 3C1.5A12, or N-MCJ 2A2.5E4.

According to yet another aspect of the invention, hybridoma cell lines that produce any of the isolated antibodies or antigen-binding fragments thereof of any embodiment of any of the foregoing aspects of the invention are provided. In some embodiments, the hybridoma is N-MCJ 3C1.3F3, N-MCJ 3C1.5A12, or N-MCJ 2A2.5E4.

According to another aspect of the invention, expression vectors that include an isolated nucleic acid molecule encoding any of the isolated antibodies or antigen-binding fragments thereof of any embodiment of any of the foregoing aspects of the invention are provided.

According to another aspect of the invention, isolated host cells that are transformed by or transfected with any of the foregoing expression vectors of a previous aspect of the invention are provided.

According to yet another aspect of the invention, plasmids that produce any antibody or antigen-binding fragment of any embodiment of any of the foregoing aspects of the invention are provided.

According to yet another aspect of the invention, compositions that include an antibody or antigen-binding fragment thereof of any embodiment of any of the foregoing aspects of the invention are provided.

According to another aspect of the invention, methods of producing an antibody that specifically binds MCJ polypeptide are provided. The methods include inoculating an animal with an MCJ polypeptide or a fragment thereof, wherein the polypeptide or fragment thereof elicits an immune response in the animal to produce the antibody; and isolating the antibody from the animal; wherein the antibody specifically binds to the MCJ polypeptide. In some embodiments, the polypeptide includes the amino acid sequence set forth as MAARGVIAPVGESLRYAEYL (SEQ ID NO:2). In some embodiments, the polypeptide includes the amino acid sequence set forth as MAARGVIAPVGESLRYAEYLC (SEQ ID NO:1). In certain embodiments, the methods also include removing a lymph node from the immunized animal, harvesting cells from the removed lymph node, fusing the harvested cells with myeloma cells to make hybridomas, expanding the hybridomas, identifying a hybridoma that produces an antibody that specifically binds to the immunogenic polypeptide, and collecting the antibody produced by the hybridoma. In some embodiments, the animal is a mouse.

According to yet another aspect of the invention, isolated, immunogenic fragments of an MCJ polypeptide are provided. In some embodiments, the immunogenic fragment includes the amino acid sequence set forth as MAARGVIAPVGESLRYAEYL (SEQ ID NO:2). In some embodiments, the immunogenic fragment is modified by the addition of a cysteine residue to the C terminal end of the fragment such that the amino acid sequence of the isolated fragment is set forth as MAARGVIAPVGESLRYAEYLC (SEQ ID NO:1).

According to certain aspects of the invention, compositions that include any of the isolated immunogenic fragments of the foregoing aspect of the invention are provided.

According to yet another aspect of the invention, methods of making an antibody that specifically binds to an MCJ polypeptide are provided. The methods include immunizing an animal with an inoculant that includes any of the isolated fragments any foregoing aspect of the invention. In certain embodiments, the inoculant also includes a carrier molecule. In some embodiments, the carrier molecule is bovine serum albumin (BSA).

According to yet another aspect of the invention, methods of determining the amount of MCJ polypeptide in a sample are provided. The methods include contacting a sample with the antibody or antigen-binding fragment thereof that binds specifically to an epitope of MCJ polypeptide, and quantitating the amount of binding of the antibody or antigen-binding fragment thereof in the sample as a determination of the amount of MCJ polypeptide in the sample. In some embodiments, the epitope of the MCJ polypeptide includes the amino acid sequence MAARGVIAPVGESLRYAEYL (SEQ ID NO:2). In certain embodiments, the antibody competitively inhibits binding of an WN.F3, WN.A12, or WN.E4 antibody to an epitope of an MCJ polypeptide. In some embodiments, the antibody is a monoclonal antibody. In some embodiments, the antibody is WN.F3, WN.A12, or WN.E4. In certain embodiments, the antibody has a CDR3 region of a monoclonal antibody produced by: i) hybridoma N-MCJ 3C1.3F3, which was deposited under ATCC no. #PTA-8135; ii) hybridoma cell line N-MCJ 3C1.5A12, which was deposited under ATCC no. #PTA-8133; or iii) hybridoma cell line N-MCJ 2A2.5E4, which was deposited under ATCC no. #PTA-8134. In some embodiments, the antibody specifically binds the epitope with an affinity of about $1\times10^{-6}$, $1\times10^{-7}$, $1\times10^{-8}$, $1\times10^{-9}$M or less. In certain embodiments, the antibody specifically binds the epitope with an affinity of about $1\times10^{-10}$M, $1\times10^{-11}$M or about $5\times10^{-10}$M or less. In some embodiments, the antibody is a polyclonal antibody. In some embodiments, the antibody is OD-C-MCJ. In some embodiments, the antibody specifically binds an epitope that includes MAARGVIAPVGESLRYAEYL SEQ ID NO:2 with an affinity greater than the affinity of a WN.F3, WN.A12, and/or WN.E4 antibody for the epitope. In certain embodiments, the antibody or antigen-binding fragment thereof includes an MCJ peptide-binding CDR3 region or a functional variant thereof. In some embodiments, the CDR3 region is of a monoclonal antibody produced by: i) hybridoma N-MCJ 3C 1.3F3, which was deposited under ATCC no. #PTA-8135; ii) hybridoma cell line N-MCJ 3C1.5A12, which was deposited under ATCC no. #PTA-8133; or iii) hybridoma cell line N-MCJ 2A2.5E4, which was deposited under ATCC no. #PTA-8134. In some embodiments, the antibody or antigen-binding fragment thereof further includes a CDR2 region or a functional variant thereof. In some embodiments, the antibody or antigen-binding fragment thereof further includes a CDR3 region or a functional variant thereof. In certain embodiments, the antibody is a recombinant antibody. In some embodiments, the antibody or antigen-binding fragment thereof is attached to a detectable label. In some embodiments, the detectable label is a fluorescent label, an enzyme label, a radioactive label, a nuclear magnetic resonance active label, a luminescent label, or a chromophore label. In certain embodiments, the MCJ polypeptide is a human MCJ polypeptide. In some embodiments, the sample is a cell sample. In some embodiments, the sample is a tissue sample. In certain embodiments, the sample is an in vivo sample. In some embodiments, the sample is obtained from a subject. In some embodiments, the subject has cancer. In certain embodiments, the sample includes cancer cells. In some embodiments, the cancer is breast cancer, ovarian cancer, peritoneal cancer, brain cancer, melanoma, uterine cancer prostate cancer, Wilms' tumor, lymphoma, or lung cancer. In some embodiments, the cancer is a cancer that may be treated with doxorubicin.

According to yet anther aspect of the invention, methods of selecting a treatment for cancer in a subject are provided. The methods include obtaining a level of MCJ polypeptide from a sample in or obtained from the subject, and selecting the treatment for cancer in the subject based at least in part on the level of MCJ polypeptide obtained, wherein the level of MCJ polypeptide is determined by the method set forth in any embodiment of any of the foregoing aspects of the invention. In some embodiments, the cancer is breast cancer, ovarian cancer, peritoneal cancer, brain cancer, melanoma, uterine cancer prostate cancer, Wilms' tumor, lymphoma, or lung cancer. In certain embodiments, the cancer is a cancer that may be treated with doxorubicin.

According to another aspect of the invention, methods evaluating a treatment for cancer are provided. The methods include determining a first level of MCJ polypeptide from a sample in or obtained from a cell culture or subject undergoing treatment for regulating MCJ polypeptide levels, determining a second level of MCJ polypeptide from a sample in or obtained from the cell culture or subject at least one day after obtaining the first level, wherein the cell culture and/or subject was administered a treatment for cancer between the first determining and the second determining, and comparing the first level to the second level as an evaluation of the treatment, wherein the levels of MCJ polypeptide are determined by the method set forth in any embodiment of any of the aforementioned aspects of the invention. In some embodiments, the cancer is breast cancer, ovarian cancer, peritoneal cancer, brain cancer, melanoma, uterine cancer prostate cancer, Wilms' tumor, lymphoma, or lung cancer. In some embodiments, the cancer is a cancer that may be treated with doxorubicin.

According to yet another aspect of the invention, methods for assessing the drug resistance status of a cancer in a subject are provided. The methods include obtaining a level of MCJ polypeptide from a sample obtained from a subject, and comparing the level to a control level of MCJ polypeptide as an assessment of the drug resistance status of the cancer, wherein the level of MCJ polypeptide is determined by the method set forth in any embodiment of any of the aforementioned aspect of the invention. In certain embodiments, the cancer is breast cancer, ovarian cancer, peritoneal cancer, brain cancer, melanoma, uterine cancer prostate cancer, Wilms' tumor, lymphoma, or lung cancer. the cancer is a cancer that may be treated with doxorubicin.

According to yet another aspect of the invention, methods for identifying a compound that modulates a level of MCJ polypeptide in a cell are provided. The methods include contacting a test cell with a candidate compound, determining the amount of MCJ polypeptide in the test cell, and comparing an amount of MCJ polypeptide detected in the test cell to an amount of MCJ polypeptide in a control cell that is not contacted with the candidate compound, wherein a change in the level of MCJ polypeptide in the test cell compared to the control cell identifies the candidate compound as modulating the level of MCJ polypeptide in the test cell. In certain embodiments, the level of MCJ polypeptide decreases indicating that the compound decreases the level of MCJ polypeptide and in other embodiments, the level of MCJ polypeptide increases indicating that the compound increases the level of MCJ polypeptide. In some embodiments, the cell is a cultured cell. In some embodiments, the cell is an in vivo cell. In certain embodiments, the cell is obtained from a subject. In some embodiments, the subject has cancer. In certain embodiments, the cancer is breast cancer, ovarian cancer, peritoneal cancer, brain cancer, melanoma, uterine cancer prostate cancer, Wilms' tumor, lymphoma, or lung cancer. In certain embodiments, the cancer is a cancer that may be treated with doxorubicin. In some embodiments, the means for determining the amount of MCJ polypeptide includes any of the methods set forth in any embodiment of any of the foregoing aspects of the invention.

According to yet another aspect of the invention, kits for detecting a level of MCJ in a cell, tissue, and/or subject sample are provided. The kits include a package including a container containing any of the isolated antibody or antigen-binding fragment thereof of any embodiment of any of the foregoing aspects of the invention, and optionally, instructions for use of the antibody or antigen-binding fragment thereof to detect the level of MCJ polypeptide in a cell, tissue, and/or subject. In some embodiments detecting the level of MCJ includes detecting the level of MCJ mRNA in the cell, tissue, or subject sample. In certain embodiments, detecting the level of MCJ includes detecting the level of MCJ polypeptide in the cell, tissue, or subject sample. In some embodiments, the sample includes cancer cells. In certain embodiments, the cancer is breast cancer, ovarian cancer, peritoneal cancer, brain cancer, melanoma, uterine cancer prostate cancer, Wilms' tumor, lymphoma, or lung cancer. In certain embodiments, the cancer is a cancer that may be treated with doxorubicin. In some embodiments, the means for determining the level of MCJ polypeptide includes any of the methods set forth in any embodiment of any of the foregoing aspects of the invention.

These and other aspects of the invention will be described in further detail in connection with the detailed description of the invention.

BRIEF DESCRIPTION OF THE DRAWINGS

FIG. 1A shows homologous MCJ polypeptide sequences in different species found by BLASTp search. Alignment made using T-Coffee program. FIG. 1B shows possible scenarios for the gene duplication event that resulted in MCJ polypeptide evolution in vertebrates. The models for gene duplication after the divergence of the Fly/worm TIM14-like clade from the vertebrates (top panel) and gene duplication prior to the divergence of Fly/worm TIM14-like clade from the vertebrate clades with subsequent possible gene loss in the Fly/worm lineage (bottom panel) are shown. In FIG. 1A: *H. sapiens* MCJ sequence is SEQ ID NO:25; *H. sapiens* TIM14 sequence is SEQ ID NO:26; *D. melanogaster* sequence is SEQ ID NO:27; *A. thaliana* sequence is SEQ ID NO:28; *D. discoideum* sequence is SEQ ID NO:29; *E. nidulans* sequence is SEQ ID NO:30; *C. elegans* sequence is SEQ ID NO:31; *S. cerevisiae* sequence is SEQ ID NO:32; *S. cerevisiae* TIM14 sequence is SEQ ID NO:33.

FIG. 3A shows results when total RNA was extracted from MCF7 and MCF7/ADR breast cancer cells and examined for the expression of MCJ and HPRT by RT-PCR. FIG. 3B shows a histogram indicating the level of expression of MCJ relative to HPRT in MCF7 and MCF7/ADR cells was examined by quantitative real time RT-PCR. FIG. 3C shows results when total RNA was extracted from MCF7 and MCF7/IL6 cells and examined for the expression of MCJ and HPRT by RT-PCR. FIG. 3D shows results when total RNA was extracted from MCF7 cells cultured for 8 days in medium alone or in the presence of IL-6 (50 ng/ml). MCJ and HPRT expression were examined by RT-PCR. FIG. 3E shows results when MCF7 cells were cultured as in FIG. 3D and MCJ expression relative to HPRT was analyzed by real-time RT-PCR. FIGS. 3F and G show results when total RNA was extracted from MDA-MB-321 and MD22 breast cancer cells (FIG. 3F and uterine cancer cells MES-SA and MES-SAIDx5 (FIG. 3G) and examined for the expression of MCJ and HPRT by RT-PCR.

FIG. 4A shows results when MCF7 cells were transfected with the empty pSuperEGFP (control) or pSuperEGFP-siMCJ (siMCJ) plasmid. Total RNA was extracted 36 h after transfection and MCJ (M) and HPRT (H) gene expression were examined by RT-PCR. FIGS. 4B and C show results when total RNA from MCF7, MCF7/siMCJ-1B and MCF7/siMCJ-3B cells was extracted and used to examine MCJ and HPRT expression by RT-PCR. FIG. 4C shows results when total RNA isolated as in FIG. 4B was used to examine MCJ expression relative to HPRT by real-time RT-PCR analysis. FIG. 4D shows results when endogenous MCJ polypeptide expression was examined by Western blot analysis. Whole extracts from MCF7 (M), MCF7/ADR (ADR), MCF7/siMCJ (siMCJ)-1B and -3B cells were examined for MCJ with an anti-MCJ Ab. As a positive control, whole extracts from MCJ-transfected 293T cells (293T MCJ) were used. Actin expression was examined as loading control. FIGS. 4E and F show results when cell viability was determined by MTT assay. $LD_{50}$ values were calculated by non-linear regression. $LD_{50}$ values for doxorubicin (E) were 0.078 µM (MCF7), 16.60 µM (MCF7/ADR), 1.35 µM (MCF7/si MCJ-1B) and 9.29 µM (MCF7/si MCJ-3B). $LD_{50}$ values for paclitaxel (F) were 0.05 µM (MCF7), 4.5 µM (MCF7/ADR), 2.0 µM (MCF7/si MCJ-1B) and 4.99 µM (MCF7/si MCJ-3B). A representative of four individual experiments is shown.

FIG. 6A shows results when whole cell extracts from MCF7 (M), MCF7/ADR (ADR), MCF7/siMCJ (siMCJ)-1B and -3B cells were used to examine ABCB1 expression by Western blot analysis. Actin was also examined as a loading control. FIG. 6B shows results when total RNA extracted from MCF7 (M), MCF7/ADR (ADR), MCF7/siMCJ (siMCJ)-1B and -3B cells was used to examine ABCB1 and HPRT gene expression by RT-PCR. FIG. 6C shows reuslts of quantitative real time RT-PCR analysis of the ABCB1 expression relative to HPRT in MCF7, MCF7/siMCJ-1B and -3B cells. FIG. 6D shows results when total RNA was extracted from MCF7 (M), MCF7/ADR (ADR), MCF7/siMCJ (siMCJ)-1B and -3B cells and used to examine ABC41, ABCG2 and HPRT gene expression by RT-PCR. FIG. 6E shows results when whole cell extracts from MCF7 (M), MCF7/ADR (ADR) and MCF7/ADR-MCJ (A-MCJ) cells were used to examine ABCB1 expression by Western blot analysis. Actin expression was examined as a loading control.

FIG. 7A shows results when MCF7 and MCF7/siMCJ-1B cells were treated with medium alone (gray-filled profiles) or with 3 µM of doxorubicin (3 h) in the absence (thin line profiles) or the presence (thick line profiles) of verapamil (10 µM). The numbers represent mean fluorescence intensity for doxorubicin. FIG. 7B shows results when MCF7, MCF7/ADR, MCF7/siMCJ-1B, MCF7/siMCJ-3B cells were plated and treated in the absence or presence of different concentrations of 5-FU. Cell viability was determined by the MTT assay. $LD_{50}$ values for 5-FU were 0.94 µM (MCF7), 2.34 µM (MCF7/ADR), 1.93 µM (MCF7/si MCJ-1B) and 1.71 µM (MCF7/si MCJ-3B).

FIG. 8A shows results from when nuclear extracts from MCF7 (M), MCF7/siMCJ (siMCJ)-1B and -3B cells were examined by EMSA using $^{32}$P-labeled double-stranded oligos specific for CEB/P, NF-κB and AP-1. FIG. 8B shows results from when AP-1 DNA binding was examined by EMSA using nuclear extracts from MCF7/siMCJ-1B cells and an AP-1 oligo. Binding reactions were performed in the absence (−) or presence of an anti-c-Jun, c-Fos, JunB or Jun family (Jun fam.) Abs. FIG. 8C shows results from when MCF7, MCF7/siMCJ-1B and MCF7/siMCJ-3B cells were co-transfected with a AP-1 luciferase reporter construct and β-gal expressing plasmid. After 24 h, luciferase values were measured and normalized to β-gal for efficiency of the transfection. The error bars represent standard error of mean (SEM) (n=3). FIG. 8D show results from whole cell extracts from MCF7 (M), MCF7/siMCJ (siMCJ)-1B and -3B cells that were analyzed for c-Jun expression by Western blot analysis. Actin was used as loading control. FIG. 8E shows results from whole cell lysates from MCF7 cells that were treated in absence or presence of a proteasome inhibitor MG132 (5 μM) for 4 h and analyzed for c-Jun expression by Western blot analysis. FIG. 8F shows results from when MCF7/siMCJ-3B (3B) and -1B (1B) cells were transfected with the empty plasmid (Cont) or dnJNK1 plasmid. Whole cell lysates were analyzed for ABCB, actin and c-Jun by Western blot. FIG. 8G shows a diagrammatic model representing Golgi localized MCJ downregulating the levels of c-Jun and thus inhibiting ABCB1 expression, allowing the intracellular accumulation of doxorubicin. In the absence of MCJ, increased levels of c-Jun leads to increased c-Jun transcriptional activity resulting in ABCB1 expression. Doxorubicin is effluxed out of the cell by the ABCB1 polypeptide.

FIG. 9A shows results of analysis of whole cell lysates from MCF7 and siMCJ cells, which were analyzed for HIF-1α expression by Western Blot. Actin was blotted as loading control. FIG. 9B shows results from when total RNA was isolated from MCF7 and MCF7/siMCJ cells and analyzed for HIF1α expression relative to HPRT expression by RT-PCR.

DETAILED DESCRIPTION OF THE INVENTION

Figure 1:
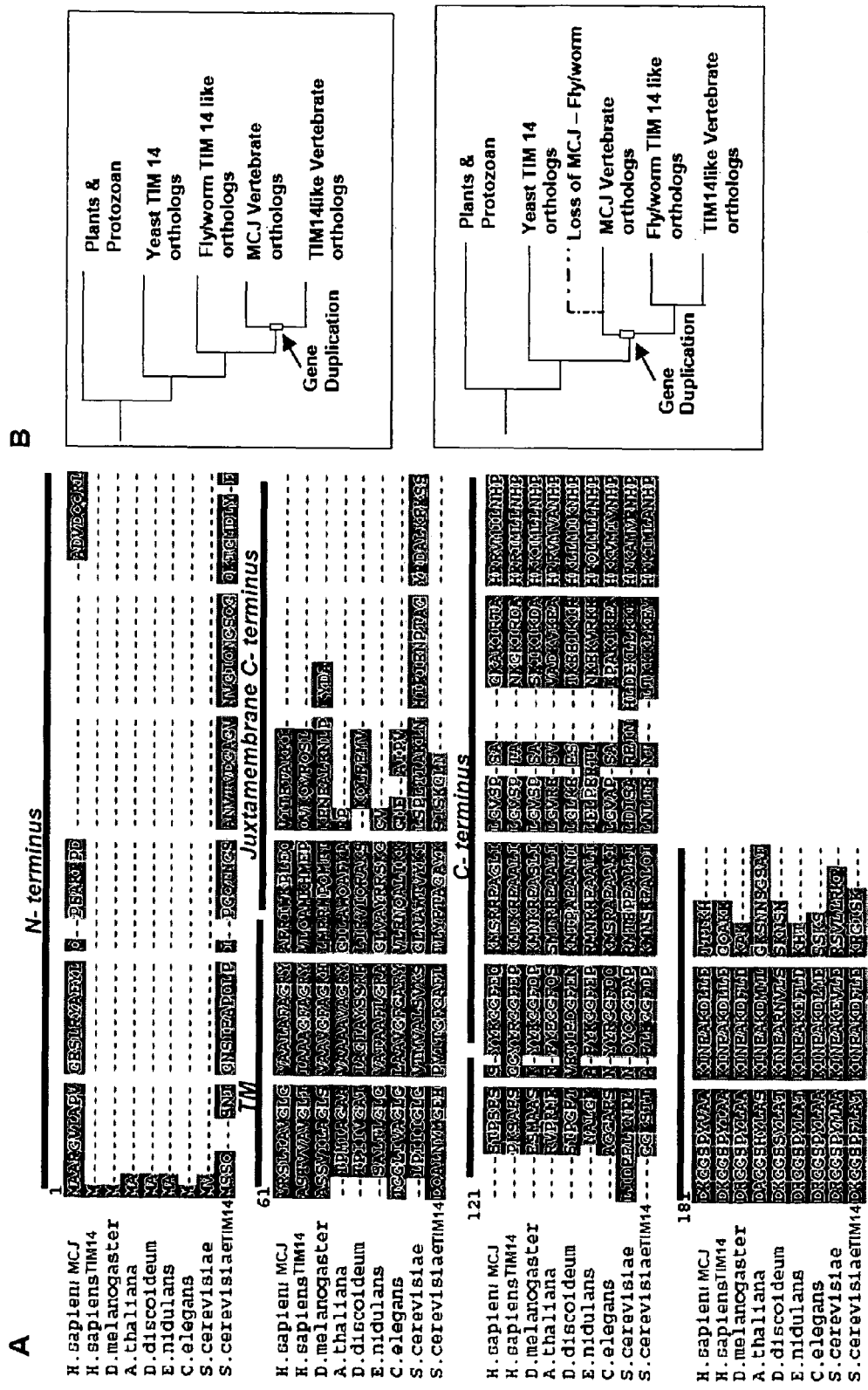
FIG. 1 provides sequences demonstrating phylogenetic analysis and sequence alignment of MCJ polypeptide.

Methylation controlled J polypeptide (MCJ) is a newly identified member of the DnaJ family of co-chaperones. Hypermethylation-mediated transcriptional silencing of the MCJ gene has been associated with increased chemotherapeutic resistance in ovarian cancer. However, the biology and function of the MCJ polypeptide remain unknown. It has now been shown that MCJ is a type II transmembrane co-chaperone localized in the Golgi apparatus and present only in vertebrates. MCJ is expressed in drug-sensitive breast cancer cells, but not in multidrug resistant cells. Inhibition of MCJ expression increases resistance to specific drugs by inducing expression of the ABCB1 drug transporter that prevents intracellular drug accumulation. Induction of ABCB1 gene expression is mediated by increased levels of c-Jun due to an impaired degradation of this transcription factor in the absence of MCJ. Thus, MCJ is important in breast cancer cells to prevent c-Jun-mediated expression of ABCB1 and maintain drug response.

The discovery of high-affinity antibodies that specifically bind MCJ polypeptide facilitates analysis of cancer and cancer therapeutics. For example, it has been discovered that a decrease in the level of MCJ polypeptide in a cancer cell may lead to an increase in cancer-drug resistance (e.g., multidrug resistance) in the cell. Thus, detection of a reduced level of MCJ in a cell, tissue, and/or subject sample diagnosed with cancer may be useful in the selection of a drug therapy with which to treat the cancer. In addition, high-affinity antibodies that specifically bind MCJ polypeptide may be useful to monitor the status of drug resistance in a cell or subject with cancer through detection of levels of MCJ polypeptide in the cell or subject. Additional methods of the invention include, in part, determining the effect of a candidate therapeutic compound on the level of MCJ polypeptide in a cell or subject. Methods and antibodies or antigen-binding fragments thereof of the invention may also be used to assess and monitor the status of multidrug resistance in a cell or subject. Methods and antibodies of the invention may also be used to assess the stage or status of cancer in a cell or subject by monitoring the level of MCJ polypeptide present in a cell or subject before and after administration of a treatment regimen, or during the onset, progression or regression of a cancer. A wild-type, full-length MCJ polypeptide amino acid sequence is set forth as GENBANK® Accession No. AAD38506. A nucleic acid sequence encoding wild-type, full-length MCJ polypeptide is set forth as GENBANK® Accession No. AF126743.

The present invention provides antibodies or antigen-binding fragments thereof that bind specifically to MCJ polypeptide, compositions that include one or a combination of such antibodies or antigen-binding fragments thereof, and hybridoma cell lines that produce the antibodies. The invention also relates to the use of anti-MCJ antibodies or antigen-binding fragments thereof for diagnosis of multidrug resistance in cancer and for use in the selection of treatments for cancer. The invention, in part, also includes fragments of an MCJ polypeptide (e.g., immunogenic fragments), compositions comprising such fragments, and the use of MCJ polypeptide fragments for the production of anti-MCJ antibodies.

There may be allelic variation in MCJ polypeptide sequences of the invention including wild-type MCJ polypeptide sequences and/or mutant MCJ polypeptide sequences. As used herein, the term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides with altered amino acid sequences. An allelic variant of a polypeptide is a polypeptide encoded by an allelic variant of a gene. It will be understood by those of ordinary skill in the art that such allelic variations may occur in full-length wild-type and mutant MCJ polypeptides and in fragments of wild-type and mutant polypeptides. MCJ polypeptides of the invention may be allelic variants of wild-type MCJ or mutant MCJ polypeptide sequences.

It has been determined that the level of MCJ polypeptide expressed in cancer cells correlates with the presence of multidrug resistance in cancer, and that a reduced amount of MCJ polypeptide expression corresponds to an increase in multidrug resistance in cancer cells and tissues. A reduction in MCJ expression in cancer cells has also now been correlated with a more negative prognosis for a subject than the prognosis if the subject's cancer cells have a higher level of MCJ expression. Thus, a higher level of expression of MCJ on cancer cells is associated with a lower occurrence of multidrug resistance and a better prognosis in the subject. One of ordinary skill in the art will recognize that the terms higher, lower, reduced, increased, may be represent relative levels or values as compared to control levels or values.

In some aspects, the invention may include the synthesis of an MCJ polypeptide (e.g., a fragment of a full-length MCJ polypeptide). Synthesis methods of the invention may include any art-known synthetic methods. As used herein, the terms "protein" and "polypeptide" are used interchangeably and thus the term polypeptide may be used to refer to a full-length protein and may also be used to refer to a fragment of a full-length protein.

As used herein with respect to polypeptides, proteins, or fragments thereof, the term "isolated" means separated from its native environment and present in sufficient quantity to permit its identification or use. Isolated, when referring to a protein or polypeptide, means, for example: (i) selectively produced by expression cloning or (ii) purified as by chromatography or electrophoresis. Isolated proteins or polypeptides may be, but need not be, substantially pure. The term "substantially pure" means that the proteins or polypeptides are essentially free of other substances with which they may be found in production, nature, or in vivo systems to an extent practical and appropriate for their intended use. Substantially pure polypeptides may be obtained naturally or produced using methods described herein and may be purified with techniques well known in the art. Because an isolated polypeptide may be admixed with a pharmaceutically acceptable carrier in a pharmaceutical preparation, the polypeptide may comprise only a small percentage by weight of the preparation. The polypeptide is nonetheless isolated in that it has been separated from the substances with which it may be associated in living systems, i.e. isolated from other polypeptides.

According to some aspects of the invention, fragments of full-length MCJ polypeptide are provided. Fragments of the invention are preferably fragments that retain a distinct functional capability of the polypeptide. Functional capabilities which can be retained in a fragment include interaction with antibodies, and interaction with other polypeptides or fragments thereof. polypeptide fragments may be natural fragments or may be synthesized using art-known methods, and tested for function using the methods exemplified herein. Full-length MCJ and fragments of MCJ that are useful in methods and compositions of the invention may be recombinant polypeptides.

A fragment of a full-length MCJ polypeptide may comprise at least 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, or 149 (including each integer in between) contiguous amino acids of MCJ polypeptide having a consecutive sequence found in wild-type MCJ polypeptide or in a modified MCJ polypeptide sequence as described herein. In some embodiments, a fragment includes the C-terminal region of an MCJ polypeptide. Such MCJ polypeptides that are fragments of full-length MCJ polypeptide may be useful for a variety of purposes, including in the preparation of molecules that bind specifically to synthetic and natural MCJ polypeptides and in immunoassay methods well known to those of ordinary skill in the art, including, but not limited to, competitive binding immunoassays.

Non-limiting examples of MCJ polypeptides that are fragments of full-length MCJ polypeptide are

| | |
|---|---|
| MAARGVIAPVGESLRYAEYL, | (SEQ ID NO: 2) |
| MAARGVIAPVGESLRYAEYLQPSAKRPDA, | (SEQ ID NO: 3) |
| MAARGVIAPVGESLRYAEYLQPSA, | (SEQ ID NO: 4) |
| MAARGVIAPVGESLRYAE, | (SEQ ID NO: 5) |
| RGVIAPVGESLRYAEYLC, | (SEQ ID NO: 6) |
| MAARGVIAPVGES, | (SEQ ID NO: 7) |
| AARGVIAPVGESLRYAEYL, | (SEQ ID NO: 8) |
| MAARGVIAPVGESLRYAEYLQPSAKRPDADV, | (SEQ ID NO: 9) |
| MAARGVIAPVGESLRYAEYLQPSAKRPDADVDQQGLVRS, | (SEQ ID NO: 10) |
| MAARGVIAPVGESLRYAEYLQPSAKRPDADVDQQGL, | (SEQ ID NO: 11) |
| MAARGVIAPVGESLRYAEYLQPSAKRPDADVD, | (SEQ ID NO: 12) |
| MAARGVIAPVGESLRYAEYLQPSAK, | (SEQ ID NO: 13) |
| MAARGVIAPVGESLRYAEYLQPSAKRPDAD, | (SEQ ID NO: 14) |
| MAARGVIAPVGESLRYAEYLQPSAKRPDADVDQQGLVRSLIAVGL; | (SEQ ID NO: 15) |
| MAARGVIAPVGESLRYAEYLQP, | (SEQ ID NO: 16) |
| MAARGVIAPVGESLRYAEYLQPSAKR, | (SEQ ID NO: 17) |
| GVIAPVGESLRYAEYL | (SEQ ID NO: 18) |
| ARGVIAPVGESLRYAEYL, or | (SEQ ID NO: 19) |
| VIAPVGESLRYAEYL. | (SEQ ID NO: 20) |

One of ordinary skill in the art will understand how to prepare additional MCJ polypeptides that are fragments of full-length MCJ polypeptide for use in the methods of the invention. It will be understood that an MCJ polypeptide may be a polypeptide that includes a desired epitope of MCJ polypeptide and that has an additional 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, or 149 amino acids, including all integers up to the sequence of a full-length MCJ polypeptide minus one amino acid. Such polypeptides are readily envisioned by one of ordinary skill in the art. For example, up to 114 amino acids may be added to the C terminal end of the immunogenic sequence that comprises the amino acid sequence set forth as MAARGVIAPVGESLRYAEYL (SEQ ID NO:2). Such MCJ polypeptides that are fragments of full-length MCJ, as well as full-length MCJ polypeptide, can be used to make antibodies that specifically bind to MCJ polypeptides.

A "modified" wild-type or mutant full-length MCJ polypeptide or polypeptide that is a fragment thereof may include deletions, point mutations, truncations, amino acid substitutions and/or additions of amino acids or non-amino acid moieties. Modifications of a polypeptide of the invention may be made by modification of the nucleic acid that encodes the polypeptide or alternatively, modifications may be made directly to the polypeptide, such as by cleavage, addition of a linker molecule, addition of a detectable moiety, such as a fluorescent label, and the like. Modifications also embrace fusion proteins comprising all or part of the polypeptide's amino acid sequence.

In general, modified polypeptides (e.g. modified MCJ wild-type or mutant polypeptides) may include polypeptides that are modified specifically to alter a feature of the polypeptide unrelated to its physiological activity. For example, cysteine residues can be substituted or deleted to prevent unwanted disulfide linkages. A residue may be added at the N or C-terminal end of the polypeptide, for example, SEQ ID NO:1, includes a cysteine residue (C) at the extreme C-terminal end of the MCJ polypeptide set forth as (SEQ ID NO:2). Polypeptides can be synthesized with modifications and/or modifications can be made in a polypeptide by selecting and introducing an amino acid substitution, deletion, or addition. Modified polypeptides then can be tested for one or more activities (e.g., antibody to binding, antigenicity, etc.) to determine which modification provides a modified polypeptide with the desired properties.

The skilled artisan will also realize that conservative amino acid substitutions may be made in a polypeptide to provide functionally equivalent polypeptides, i.e., a modified MCJ polypeptide that retains a functional capability of an un-modified MCJ polypeptide. As used herein, a "conservative amino acid substitution" refers to an amino acid substitution that does not alter the relative charge or size characteristics of the polypeptide in which the amino acid substitution is made. Modified MCJ polypeptides can be prepared according to methods for altering polypeptide sequence and known to one of ordinary skill in the art such. Exemplary functionally equivalent MCJ polypeptides include conservative amino acid substitutions of an MCJ polypeptide, or fragments thereof, such as a modified MCJ polypeptide. Conservative substitutions of amino acids include substitutions made amongst amino acids within the following groups: (a) M, I, L, V; (b) F, Y, W; (c) K, R, H; (d) A, G; (e) S, T; (f) Q, N; and (g) E, D.

Conservative amino-acid substitutions in an MCJ polypeptide typically are made by alteration of a nucleic acid encoding the polypeptide. Such substitutions can be made by a variety of methods known to one of ordinary skill in the art. For example, amino acid substitutions may be made by PCR-directed mutation, site-directed mutagenesis, or by chemical synthesis of a gene encoding the MCJ polypeptide. Where amino acid substitutions are made to a small fragment of a polypeptide, the substitutions can be made by directly synthesizing the polypeptide. The activity of functionally equivalent fragments of MCJ polypeptides can be tested by cloning the gene encoding the altered polypeptide into a bacterial or mammalian expression vector, introducing the vector into an appropriate host cell, expressing the altered polypeptide, and testing for a functional capability of the polypeptide as disclosed herein.

As described above, a fragment of a full-length MCJ polypeptide may be a synthetic polypeptide. As used herein, the term "synthetic" means artificially prepared. A synthetic polypeptide is a polypeptide that is synthesized and is not a naturally produced polypeptide molecule (e.g., not produced in an animal or organism). It will be understood that the sequence of a natural polypeptide (e.g., an endogenous polypeptide) may be identical to the sequence of a synthetic polypeptide, but the latter will have been prepared using at least one synthetic step.

An antibody of the invention may be raised against a natural or a synthetic MCJ polypeptide. Such a polypeptide, may, in some embodiments, comprise a sequence for an epitope that includes the amino acid sequence MAARGVIAPV-GELSRYAEYL (SEQ ID NO:2). An antibody raised against the polypeptide set forth as SEQ ID NO:1 is able to specifically bind with high affinity to a synthetic polypeptide or natural polypeptide that comprises the amino acid sequence MAARGVIAPVGELSRYAEYL (SEQ ID NO:2). Thus, even though an epitope of a synthetic MCJ polypeptide may differ slightly from the same epitope in a natural MCJ polypeptide, an antibody raised against an MCJ epitope specifically binds with high affinity to the natural MCJ epitope and to a synthetic MCJ epitope. Antibodies of the invention are able to distinguished between MCJ polypeptides and other polypeptides. An anti-MCJ antibody made using an MCJ antigen of the invention is useful in methods to detect MCJ polypeptides (full-length and fragments thereof) and to distinguish between MCJ polypeptides and other polypeptides.

The invention includes in one aspect, methods and compositions for preparing antibodies that specifically bind MCJ polypeptides. MCJ polypeptides may be used as antigens to make antibodies that specifically bind MCJ. Compositions useful for making an antibody of the invention may include an MCJ polypeptide. In some embodiments of the invention, an MCJ polypeptide may be full-length MCJ polypeptide or fragment thereof.

Methods of the invention may also include the use of fragments of an MCJ polypeptide for the production of antibodies that specifically bind MCJ polypeptides. In some embodiments, an antibody specifically binds to an epitope of SEQ ID NO:2 that is present in an MCJ polypeptide having the sequence set forth as MAARGVIAPVGESLRYAEYLC (SEQ ID NO:1). In some embodiments, an immunogenic polypeptide can be as small as 5 amino acids in length. In some embodiments of the invention, a carrier molecule, e.g. bovine serum albumin (BSA), or keyhole limpet hemocyanin (KLH) may be attached to a MCJ polypeptide to increase antigenicity of the polypeptide. For example, the KLH may be attached to a MCJ polypeptide such as MAARGVI-APVGESLRYAEYLC (SEQ ID NO;1) and used to generate a antibody that specifically binds an MCJ polypeptide with high affinity. Thus, full-length MCJ or fragments of MCJ that include the desired epitope for antibody production can be used in the production of an antibody that specifically binds to the epitope. In some embodiments, a residue may be added to the C-terminal end to allow the attachment of a compound such as KLH or BSA. In some embodiments, the residue added may be cysteine. For example, a cysteine residue may be added to the C-terminal end of SEQ ID NO:2 to prepare SEQ ID NO:1 and a molecule such as BSA or KLH may then be added to increase the antigenicity of the polypeptide for antibody production. Anti-MCJ polypeptide antibodies or antigen-binding fragments thereof may be purified using art-known affinity purification and/or affinity selection methods. Affinity selection is selection of antibodies or antigen-binding fragments thereof for binding to the target material (e.g., an MCJ polypeptide).

In some embodiments of the invention, an antibody that specifically binds to MCJ polypeptide is generated using full-length MCJ polypeptide as an immunogenic polypeptide. In some embodiments, antibodies that specifically bind an MCJ polypeptide may be generated using a fragment of full-length MCJ that comprises the amino acid sequence MAARGVIAPVGESLRYAEYLC (SEQ ID NO:1). For example, the monoclonal antibodies WN.F3, WN.A12, and WN.E4, have been generated and each specifically binds an MCJ epitope that includes the sequence MAARGVI-APVGESLRYAEYL (SEQ ID NO:2). Thus, the WN.F3, WN.A12, and WN.E4 antibodies specifically bind an MCJ polypeptide that includes an epitope with the sequence set forth as MAARGVIAPVGESLRYAEYL (SEQ ID NO:2). For the preparation of antibodies that specifically bind to the epitope MAARGVIAPVGESLRYAEYL (SEQ ID NO:2), longer fragments of MCJ may be also be used as long as the fragment includes the sequence set forth as MAARGVI-APVGESLRYAEYL (SEQ ID NO:2).

It will be understood by those of ordinary skill in the art that it is preferable that a fragment of MCJ for use as an immunogenic fragment in the methods of the invention be at least 5, 6, 7, 8, 9, 10, 11, 12, 13, 14, 15, 16, 17, 18, 19, 20 or more amino acids in length. In some embodiments, an immunogenic MCJ fragment may be shorter than the sequence set forth as MAARGVIAPVGESLRYAEYL (SEQ ID NO:2). One of ordinary skill in the art will be able to use the guidance provided herein to make additional fragments of MCJ polypeptide that can be used in methods of the invention.

As used herein, the term "antibody" refers to a glycopolypeptide that may include at least two heavy (H) chains and two light (L) chains inter-connected by disulfide bonds. Each heavy chain is comprised of a heavy chain variable region (abbreviated herein as HCVR or $V_H$) and a heavy chain constant region. The heavy chain constant region is comprised of three domains, $C_H1$, $C_H2$ and $C_H3$. Each light chain is comprised of a light chain variable region (abbreviated herein as LCVR or $V_L$) and a light chain constant region. The light chain constant region is comprised of one domain, CL. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system.

The term "antigen-binding fragment" of an antibody as used herein, refers to one or more portions of an antibody that retain the ability to specifically bind to an antigen (e.g., an MCJ polypeptide). It has been shown that the antigen-binding function of an antibody can be performed by fragments of a full-length antibody. Examples of binding fragments encompassed within the term "antigen-binding fragment" of an antibody include (i) a Fab fragment, a monovalent fragment consisting of the $V_L$, $V_H$, $C_L$ and $C_H1$ domains; (ii) a F(ab')$_2$ fragment, a bivalent fragment comprising two Fab fragments linked by a disulfide bridge at the hinge region; (iii) a Fd fragment consisting of the $V_H$ and CH1 domains; (iv) a Fv fragment consisting of the $V_L$ and $V_H$ domains of a single arm of an antibody, (v) a dAb fragment (Ward et al., (1989) *Nature* 341:544-546) which consists of a $V_H$ domain; and (vi) an isolated complementarity determining region (CDR). Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al. (1988) *Science* 242:423-426; and Huston et al. (1988) *Proc. Natl. Acad. Sci. USA* 85:5879-5883). Such single chain antibodies are also intended to be encompassed within the term "antigen-binding portion" of an antibody. These antibody fragments are obtained using conventional procedures, such as proteolytic fragmentation procedures, as described in J. Goding, Monoclonal Antibodies: Principles and Practice, pp 98-118 (N.Y. Academic Press 1983), which is hereby incorporated by reference as well as by other techniques known to those with skill in the art. The fragments are screened for utility in the same manner as are intact antibodies.

Isolated antibodies of the invention encompass various antibody isotypes, such as IgG1, IgG2, IgG3, IgG4, IgM, Ig1, IgA2, IgAsec, IgD, IgE. As used herein, "isotype" refers to the antibody class (e.g. IgM or IgG1) that is encoded by heavy chain constant region genes. Antibodies of the invention can be full length or can include only an antigen-binding fragment such as the antibody constant and/or variable domain of IgG1, IgG2, IgG3, IgG4, IgM, Ig1, IgA2, IgAsec, IgD or IgE or could consist of a Fab fragment, a F(ab')$_2$ fragment, and a Fv fragment.

In one embodiment of the invention, the peptide that specifically binds an MCJ polypeptide is an antibody or a functionally active antibody fragment. Antibodies are well known to those of ordinary skill in the science of immunology. As used herein, the term "antibody" means not only intact antibody molecules but also fragments of antibody molecules retaining MCJ-binding ability. Polypeptide fragments are also well known in the art and are regularly employed both in vitro and in vivo. In particular, as used herein, the term "antibody" means not only intact immunoglobulin molecules but also the well-known active fragments F(ab')$_2$, and Fab. F(ab')$_2$, and Fab fragments which lack the Fc fragment of intact antibody, clear more rapidly from the circulation, and may have less non-specific tissue binding of an intact antibody (Wahl et al., *J. Nucl. Med.* 24:316-325 (1983)). As is well-known in the art, the complementarity determining regions (CDRs) of an antibody are the portions of the antibody that are largely responsible for antibody specificity. The CDRs directly interact with the epitope of the antigen (see, in general, Clark, 1986; Roitt, 1991). In both the heavy chain and the light chain variable regions of IgG immunoglobulins, there are four framework regions (FR1 through FR4) separated respectively by three complementarity determining regions (CDR1 through CDR3). The framework regions (FRs) maintain the tertiary structure of the paratope, which is the portion of the antibody which is involved in the interaction with the antigen. The CDRs, and in particular the CDR3 regions, and more particularly the heavy chain CDR3 contribute to antibody specificity. Because these CDR regions and in particular the CDR3 region confer antigen specificity on the antibody these regions may be incorporated into other antibodies or peptides to confer the identical antigen specificity onto that antibody or peptide.

As discussed above the MCJ-binding polypeptides of the present invention, in some embodiments, encompass MCJ binding peptides that include an MCJ-binding region that specifically binds to human MCJ. Optionally the MCJ-binding region is a MCJ-binding CDR3 region. A "MCJ-binding CDR3 region" as used herein is a CDR3 peptide sequence derived from the monoclonal antibodies produced by the hybridomas deposited with the ATCC under ATCC number: PTA-8133 for hybridoma cell line N-MCJ 3C1.5A12), ATCC No. #PTA-8134 for hybridoma cell line N-MCJ 2A2.5E4), and ATCC no. #PTA-8135 for hybridoma cell line Accession No. N-MCJ 3C1.3F3. These three antibody producing hybridoma cell lines (N-MCJ 3C1.3F3, N-MCJ 3C1.5A12, and N-MCJ 2A2.5E4) were deposited by Applicants with the ATCC in Manassas, Va. on Jan. 11, 2007 and the viability of the culture was tested on Jan. 19, 2007. Hybridoma cell line N-MCJ 3C1.3F3 produces monoclonal antibody WN.F3 having binding specificity for MCJ. Monoclonal antibody WN.F3 includes the $CDR3_{WN.F3}$ region within its sequence. As used herein "$CDR3_{(WN.F3)}$" includes the CDR3 region of monoclonal antibody WN.F3. Hybridoma cell line N-MCJ 3C1.5A12 produces monoclonal antibody WN.A12 having binding specificity for MCJ. Monoclonal antibody WN.A12 includes the $CDR3_{(WN.A12)}$ region within its sequence. As used herein "$CDR3_{(WN.A12)}$" includes the CDR3 region of monoclonal antibody WN.A12. Hybridoma cell line N-MCJ 2A2.5E4 produces monoclonal antibody WN.E4 having binding specificity for MCJ. Monoclonal antibody WN.E4 includes the $CDR3_{(W-N.E4)}$ region within its sequence. As used herein "$CDR3_{(WN.E4)}$" includes the CDR3 region of monoclonal antibody WN.E4. Each of monoclonal antibody WN.F3, monoclonal antibody WN.A12, and monoclonal antibody WN.E4 specifically binds to MCJ.

The hybridoma cell line N-MCJ 3C1.3F3 is also referred to herein as WeN.F3. The hybridoma cell line N-MCJ 3C1.5A12 is also referred to herein as WeN.A12. The hybridoma cell line N-MCJ 2A2.5E4 is also referred to herein as WeN.E4.

The "MCJ-binding CDR3 region" refers to the $CDR3_{(WN.F3)}$, $CDR3_{(WN.A12)}$ and $CDR3_{(WN.E4)}$ peptide sequences. In one embodiment the peptides of the invention include functional variants of the MCJ-binding CDR3 region. A "functional variant" as used herein is a peptide having the sequence of the $CDR3_{(WN.F3)}$, $CDR3_{(WN.A12)}$, or $CDR3_{(WN.E4)}$ regions with conservative substitutions therein. As used herein, "conservative substitution" refers to an amino acid substitution which does not alter the relative charge or size characteristics of the peptide in which the amino acid substitution is made. Conservative substitutions of amino acids include substitutions made amongst amino acids with the following groups: (1) M,I,L,V; (2) F,Y,W; (3) K,R,H; (4) A,G; (5) S,T; (6) Q,N; and, (7) E,D. Such substitutions can be made by a variety of methods known to one of ordinary skill in the art. For example, amino-acid substitutions may be made by PCR-directed mutation, site-directed mutagenesis according to the method of Kunkel (Kunkel, *Proc. Nat. Acad. Sci. U.S.A.* 82: 488-492, 1985), or by chemical synthesis of a gene encoding the CDR3 region. These and other methods for altering a CDR3 region peptide will be known to those of ordinary skill in the art and may be found in references which compile such methods, e.g. Sambrook. et al., *Molecular Cloning: A Laboratory Manual,* 2nd edition, Cold Spring Harbor Laboratory Press, 1989. The activity of functionally equivalent variants of the MCJ-binding CDR3 region can be tested by the binding and activity assays discussed above.

For purposes of brevity the term "ATCC deposited hybridoma" is used throughout the specification to refer to the three hybridomas deposited with the ATCC in Manassas Va. on Jan. 11, 2007, the viability of the deposit was tested and found viable on Jan. 19, 2007. The term "deposited monoclonal antibody" is used to refer to each of the monoclonal antibodies (monoclonal antibody WN.F3, monoclonal antibody WN.A12, or monoclonal antibody WN.E4) produced by the ATCC deposited hybridomas. For purposes of definiteness in the attached claims each of the hybridomas, monoclonal antibodies, and polyclonal antibody is specifically recited.

Antibodies of the present invention can be polyclonal, monoclonal, or a mixture of polyclonal and monoclonal antibodies. Antibodies of the invention can be produced by methods disclosed herein or by a variety of techniques known in the art. An example of a method to produce an antibody that specifically binds MCJ is provided in the Examples section and is discussed further herein. In some embodiments, the antigen recognized by an antibody of the invention includes the amino acid sequence MAARGVIAPVGESLRYAEYL (SEQ ID NO:2).

Polyclonal and monoclonal antibodies may be prepared using techniques described in the Examples section and/or by using alternative methods that are known in the art. The Examples section provides methods of producing polyclonal antibodies that specifically bind to MCJ and also provides methods of producing monoclonal antibodies that specifically bind to MCJ. The term "monoclonal antibody," as used herein, refers to a preparation of antibody molecules of single molecular composition. A monoclonal antibody displays a single binding specificity and affinity for a particular epitope. The term "polyclonal antibody" refers to a preparation of antibody molecules that comprises a mixture of antibodies active that specifically bind a specific antigen.

A process of monoclonal antibody production may include obtaining immune somatic cells with the potential for producing antibody, in particular B lymphocytes, which have been previously immunized with the antigen of interest either in vivo or in vitro and that are suitable for fusion with a B-cell myeloma line. Mammalian lymphocytes typically are immunized by in vivo immunization (e.g., inoculation) of the animal (e.g., a mouse) with the desired protein or polypeptide, e.g., with MCJ polypeptide or a fragment thereof. As used herein, the term "inoculant" is a composition with which an animal is immunized. In some embodiments, the inoculant includes an MCJ polypeptide. In some embodiments, the polypeptide is a modified polypeptide as described herein. In some embodiments the polypeptide comprises the sequence set forth as SEQ ID NO:1. Such immunizations (e.g., inoculations) are repeated as necessary at intervals of up to several weeks to obtain a sufficient titer of antibodies. Once immunized, animals can be used as a source of antibody-producing lymphocytes. Following the last antigen boost, the animals may be sacrificed and spleen cells removed. Mouse lymphocytes give a higher percentage of stable fusions with the mouse myeloma lines described herein. In some embodiments of the invention, a BALB/c mouse can be used. However, other mouse strains, rat, rabbit, hamster, sheep, goats, camels, llamas, frogs, etc. may also be used as hosts for preparing antibody-producing cells. See; Goding (in Monoclonal Antibodies: Principles and Practice, 2d ed., pp. 60-61, Orlando, Fla., Academic Press, 1986). Mouse strains that have human immunoglobulin genes inserted in the genome (and which cannot produce mouse immunoglobulins) can also be used. Examples include the HuMAb mouse strains produced by Medarex/GenPharm International, and the XenoMouse strains produced by Abgenix. Such mice produce fully human immunoglobulin molecules in response to immunization.

Those antibody-producing cells that are in the dividing plasmablast stage fuse preferentially. Somatic cells may be obtained from the lymph nodes, spleens and peripheral blood of antigen-primed animals, and the lymphatic cells of choice depend to a large extent on their empirical usefulness in the particular fusion system. The antibody-secreting lymphocytes are then fused with (mouse) B cell myeloma cells or transformed cells, which are capable of replicating indefinitely in cell culture, thereby producing an immortal, immunoglobulin-secreting cell line. The resulting fused cells, or hybridomas, are cultured, and the resulting colonies screened for the production of the desired monoclonal antibodies. Colonies producing such antibodies are cloned, and grown either in vivo or in vitro to produce large quantities of antibody. A description of the theoretical basis and practical methodology of fusing such cells is set forth in Kohler and Milstein, Nature 256:495 (1975), which is hereby incorporated by reference.

Myeloma cell lines suited for use in hybridoma-producing fusion procedures preferably are non-antibody-producing, have high fusion efficiency, and enzyme deficiencies that render them incapable of growing in certain selective media which support the growth of the desired hybridomas. Examples of such myeloma cell lines that may be used for the production of fused cell lines include, but are not limited to Ag8, P3-X63/Ag8, X63-Ag8.653, NS1/1.Ag 4.1, Sp2/0-Ag14, FO, NSO/U, MPC-11, MPC11-X45-GTG 1.7, S194/5XXO Bu1, all derived from mice; R210.RCY3, Y3-Ag 1.2.3, IR983F and 4B210 derived from rats and U-266, GM1500-GRG2, LICR-LON-HMy2, UC729-6, all derived from humans (Goding, in Monoclonal Antibodies: Principles and Practice, 2d ed., pp. 65-66, Orlando, Fla., Academic Press, 1986; Campbell, in Monoclonal Antibody Technology, Laboratory Techniques in Biochemistry and Molecular Biology Vol. 13, Burden and Von Knippenberg, eds. pp. 75-83, Amsterdam, Elsevier, 1984). Those of ordinary skill in the art will be aware of numerous routine methods to produce monoclonal antibodies.

Fusion with mammalian myeloma cells or other fusion partners capable of replicating indefinitely in cell culture may be effected by standard and well-known techniques, for example, by using polyethylene glycol ("PEG") or other fusing agents (See Milstein and Kohler, Eur. J. Immunol. 6:511 (1976), which is hereby incorporated by reference).

An example of a procedure for raising polyclonal antibodies is provided in the Examples section herein and there are also alternative methods that are well known to those of ordinary skill in the art. As a non-limiting example, anti-MCJ polyclonal antibodies may be raised by administering an MCJ polypeptide subcutaneously to rabbits (e.g., New Zealand white rabbits) that have first been bled to obtain pre-immune serum. The MCJ polypeptide can be inoculated with (e.g., injected at) a total volume of 100 µl per site at six different sites, typically with one or more adjuvants. The rabbits are then bled two weeks after the first injection and periodically boosted with the same antigen three times every six weeks. A sample of serum is collected 10 days after each boost. Polyclonal antibodies are recovered from the serum, preferably by affinity chromatography using MCJ polypeptide to capture the antibody. This and other procedures for raising polyclonal antibodies are disclosed in E. Harlow, et al., editors, Antibodies: A Laboratory Manual (1988), which is hereby incorporated by reference. Those of ordinary skill in the art will be aware of numerous routine methods to produce polyclonal antibodies. In some embodiments, the epitope recognized by the polyclonal antibody includes an epitope with a sequence set forth as SEQ ID NO:2.

In some embodiments, antibodies may be recombinant antibodies. The term "recombinant antibody", as used herein, is intended to include antibodies that are prepared, expressed, created or isolated by recombinant means, such as antibodies isolated from an animal (e.g., a mouse) that is transgenic for another species' immunoglobulin genes, genetically engineered antibodies, antibodies expressed using a recombinant expression vector transfected into a host cell, antibodies isolated from a recombinant, combinatorial antibody library, or antibodies prepared, expressed, created or isolated by any other means that involves splicing of immunoglobulin gene sequences to other DNA sequences.

The present invention further provides nucleic acid molecules that encode anti-MCJ antibodies and vectors comprising the nucleic acid molecules as described herein. The vectors provided can be used to transform or transfect host cells for producing anti-MCJ antibodies with the specificity of antibodies described herein. In an important embodiment the antibodies produced will have the specificity of the WN.F3, WN.A12, Wn.E4, or polyclonal MCJ antibody, which is referred to herein as the OD-C-MCJ antibody. In some embodiments, the vectors can include an isolated nucleic acid molecule encoding a heavy chain and/or a light chain of an antibody of the invention encoded by a nucleic acid molecule. In a further embodiment, plasmids are given that produce the antibodies or antigen-binding fragments described herein.

Antibodies or antigen-binding fragments of the invention are, preferably, isolated. "Isolated", as used herein with respect to antibodies and antigen-binding fragments thereof, is intended to refer to an antibody (or antigen-binding fragment thereof) that is substantially free of other antibodies (or antigen-binding fragments) having different antigenic specificities (e.g., an isolated antibody that specifically binds to MCJ is substantially free of antibodies that specifically bind antigens other than MCJ). An isolated antibody that specifically binds to an epitope, isoform or variant of an MCJ polypeptide may, however, have cross-reactivity to other related antigens, e.g., a mutant form of MCJ, or a polypeptide from other species (e.g., MCJ species homologs). Moreover, an isolated antibody (or antigen-binding fragment thereof) may be substantially free of other cellular material and/or chemicals.

Antibodies of the invention include, but are not limited to antibodies that specifically bind to an MCJ polypeptide. In certain embodiments, an antibody of the invention specifically binds an MCJ polypeptide that includes an epitope with the amino acid sequence MAARGVIAPVGESLRYAEYL (SEQ ID NO:2). As used herein, "specific binding" refers to antibody binding to a predetermined antigen with a preference that enables the antibody to be used to distinguish the antigen from others to an extent that permits the diagnostic and other assays described herein. Specific binding to MCJ polypeptide means that the antibody preferentially binds MCJ versus other proteins. Typically, the antibody binds with an affinity that is at least two-fold greater than its affinity for binding to antigens other than the predetermined antigen. In some embodiments, an antibody or antigen-binding fragment thereof of the invention specifically binds to an MCJ polypeptide comprising an epitope with the sequence set for the as MAARGVIAPVGESLRYAEYL (SEQ ID NO:2). It will be understood that an antibody may specifically bind an MCJ polypeptide or fragment thereof as long as the MCJ polypeptide or fragment thereof includes an epitope specifically recognized by the antibody. Thus, an anti-MCJ antibody of the invention may specifically bind a wild-type MCJ or a mutant form of MCJ—as long as the MCJ polypeptide includes an epitope of MCJ that is recognized by the antibody.

Anti-MCJ antibodies or antigen-binding fragments thereof of the invention, can specifically bind MCJ protein and polypeptides with sub-nanomolar affinity. The binding affinities can be about $1 \times 10^{-6}$, $1 \times 10^{-7}$, $1 \times 10^{-8}$, $1 \times 10^{-9}$M or less, preferably about $1 \times 10^{-10}$M or less, more preferably $1 \times 10^{-11}$M or less. In a particular embodiment the binding affinity is less than about $5 \times 10^{-10}$M. In a particular embodiment the binding affinity is less than about $5 \times 10^{-11}$M.

In some aspects of the invention, an antibody or antigen-binding fragment thereof binds to a conformational epitope within an MCJ polypeptide. To determine if an anti-MCJ antibody bind to a conformational epitope, an antibody can be tested in assays using native protein (e.g., non-denaturing immunoprecipitation, flow cytometric analysis of cell surface binding) and denatured protein (e.g., Western blot, immunoprecipitation of denatured proteins). A comparison of the results will indicate whether the antibody binds a conformational epitope. Antibodies that bind to native protein but not denatured protein are those antibodies that bind conformational epitopes.

In some embodiments of the invention, antibodies competitively inhibit the specific binding of a second antibody to its target epitope on MCJ. In some embodiments, the target epitope comprises the sequence MAARGVIAPVGESL-RYAEYL (SEQ ID NO:2). In some embodiments, the second antibody is WN.F3, WN.A12, WN.E4 or the polyclonal anti-MCJ antibody OD-C-MCJ disclosed herein in the Examples section. To determine competitive inhibition, a variety of assays known to one of ordinary skill in the art can be employed. For example, competition assays can be used to determine if an antibody competitively inhibits binding to MCJ by another antibody (e.g., WN.F3, WN.A12, or WN.E4). These methods may include cell-based methods employing flow cytometry or solid phase binding analysis. Other assays that evaluate the ability of antibodies to cross-compete for MCJ molecules in solid phase or in solution phase, also can be used.

Certain antibodies competitively inhibit the specific binding of a second antibody to its target epitope on MCJ by at least about 10%, 20%, 30%, 40%, 50%, 60%, 70%, 80%, 90%, 95%, or 99%. Inhibition can be assessed at various molar ratios or mass ratios; for example competitive binding experiments can be conducted with a 2-fold, 3-fold, 4-fold, 5-fold, 7-fold, 10-fold or more molar excess of the first antibody over the second antibody.

Other antibodies of the invention may include antibodies that specifically bind to an epitope on MCJ defined by a second antibody. To determine the epitope, one can use standard epitope mapping methods known in the art. For example, fragments (peptides) of MCJ antigen that bind the second antibody can be used to determine whether a candidate antibody binds the same epitope. In some embodiments, an epitope comprises the sequence MAARGVIAPVGESL-RYAEYL (SEQ ID NO:2). In some embodiments, the second antibody is WN.F3, WN.A12, and/or WN.E4. For linear epitopes, overlapping polypeptides of a defined length (e.g., 5, 6, 7, 8 or more amino acids) may be synthesized. The polypeptides preferably are offset by 1 amino acid, such that a series of polypeptides covering every 4, 5, 6, 7, or 8 amino acid fragment (respectively) of the MCJ polypeptide sequence are prepared. Fewer polypeptides can be prepared by using larger offsets, e.g., 2 or 3 amino acids. In addition, longer polypeptides (e.g., 9-, 10- or 11-mers) can be synthesized. Binding of polypeptides to antibodies can be determined using standard methodologies including surface plasmon resonance (BIACORE) and ELISA assays. For examination of conformational epitopes, larger MCJ fragments, including in some embodiments fragments that include the amino acid sequence set forth as MAARGVI-APVGESLRYAEYL (SEQ ID NO:2) can be used. Other methods that use mass spectrometry to define conformational epitopes have been described and can be used (see, e.g., Baerga-Ortiz et al., *Protein Science* 11:1300-1308, 2002 and references cited therein). Still other methods for epitope determination are provided in standard laboratory reference works, such as Unit 6.8 ("Phage Display Selection and Analysis of B-cell Epitopes") and Unit 9.8 ("Identification of Antigenic Determinants Using Synthetic polypeptide Combinatorial Libraries") of *Current Protocols in Immunology*, Coligan et al., eds., John Wiley & Sons. Epitopes can be confirmed by introducing point mutations or deletions into a known epitope, and then testing binding with one or more antibodies to determine which mutations reduce binding of the antibodies.

An antibody or antigen-binding fragment thereof of the invention can be linked to a detectable label. A detectable label of the invention may be attached to the polypeptides, antibodies, or antigen-binding fragments thereof by standard protocols known in the art. In some embodiments, detectable labels may be covalently attached to an anti-MCJ antibody or antigen-binding fragment thereof of the invention. The covalent binding can be achieved either by direct condensation of existing side chains or by the incorporation of external bridging moieties. Many bivalent or polyvalent agents are useful in coupling protein molecules to other proteins, polypeptides or amine functions, etc. For example, the literature is replete with coupling agents such as carbodiimides, diisocyanates, glutaraldehyde, and diazobenzenes. This list is not intended to be exhaustive of the various coupling agents known in the art but, rather, is exemplary of the more common coupling agents. Additional descriptions of detectable labels useful in the invention is provided elsewhere herein.

The invention, in part, also includes nucleic acid sequences that encode polypeptide sequences for use in generating antibodies. For example, the invention includes nucleic acid sequences that encode an MCJ polypeptide or fragment thereof, and includes the use of the nucleic acid sequences that may be used to produce polypeptides that can be used as antigens with which to raise antibodies that recognize and specifically bind to MCJ polypeptides.

Additional nucleic acids of the invention include nucleic acids that encode an MCJ polypeptide, or an antibody or antigen-binding fragment thereof of the invention. In certain embodiments, a nucleic acid of the invention is a nucleic acid molecule that is highly homologous to a nucleic acid that encodes an MCJ polypeptide or an antibody or antigen-binding fragment thereof of the invention. Preferably the homologous nucleic acid molecule comprises a nucleotide sequence that is at least about 90% identical to the nucleotide sequence that encodes the MCJ polypeptide or antibody or antigen-binding fragment thereof. More preferably, the nucleotide sequence is at least about 95% identical, at least about 97% identical, at least about 98% identical, or at least about 99% identical to a nucleotide sequence that encodes an MCJ polypeptide or an antibody or antigen-binding fragment thereof of the invention. The homology can be calculated using various, publicly available software tools well known to one of ordinary skill in the art. Exemplary tools include the BLAST system available from the website of the National Center for Biotechnology Information (NCBI) at the National Institutes of Health.

One method of identifying highly homologous nucleotide sequences is via nucleic acid hybridization. Thus the invention also includes antibodies having MCJ-binding properties and other functional properties described herein, and includes additional MCJ polypeptides that are encoded by nucleic acid molecules that hybridize under high stringency conditions to a nucleic acid that encodes an antibody or antigen-binding fragment thereof of the invention, or an MCJ polypeptide of the invention, respectively. Identification of related sequences can also be achieved using polymerase chain reaction (PCR) and other amplification techniques suitable for cloning related nucleic acid sequences. Preferably, PCR primers are selected to amplify portions of a nucleic acid sequence of interest, such as a CDR.

The term "high stringency conditions" as used herein refers to parameters with which those of ordinary skill in the art are familiar. Nucleic acid hybridization parameters may be found in references that compile such methods, e.g. *Molecular Cloning: A Laboratory Manual*, J. Sambrook, et al., eds., Second Edition, Cold Spring Harbor Laboratory Press, Cold Spring Harbor, New York, 1989, or *Current Protocols in Molecular Biology*, F. M. Ausubel, et al., eds., John Wiley & Sons, Inc., New York. One example of high-stringency conditions is hybridization at 65° C. in hybridization buffer (3.5× SSC, 0.02% Ficoll, 0.02% polyvinyl pyrrolidone, 0.02% Bovine Serum Albumin, 2.5 mM $NaH_2PO_4$ (pH7), 0.5% SDS, 2 mM EDTA). SSC is 0.15M sodium chloride/0.015M sodium citrate, pH7; SDS is sodium dodecyl sulphate; and EDTA is ethylenediaminetetracetic acid. After hybridization, a membrane upon which the nucleic acid is transferred is washed, for example, in 2×SSC at room temperature and then at 0.1-0.5×SSC/0.1×SDS at temperatures up to 68° C.

Polypeptides and/or nucleic acids of the invention may be detectably labeled for use in methods and/or compositions of the invention. A wide variety of detectable labels are available for use in methods of the invention and may include labels that provide direct detection (e.g., fluorescence, colorimetric, or optical, etc.) or indirect detection (e.g., enzyme-generated luminescence, epitope tag such as the FLAG epitope, enzyme tag such as horseradish peroxidase, labeled antibody, etc.). A variety of methods may be used to detect a detectable label depending on the nature of the label and other assay components. Labels may be directly detected through optical or electron density, radioactive emissions, nonradiative energy transfers, etc. or indirectly detected with antibody conjugates, strepavidin-biotin conjugates, etc. Methods for using and detecting labels are well known to those of ordinary skill in the art. Methods of the invention may be used for in vivo, in vitro, and/or ex vivo imaging, including but not limited to real-time imaging. The presence of a labeled antibody in a subject can be detected by in vivo, ex vivo, or in vitro imaging using standard methods. Examples of detection methods include, but are not limited to, MRI, functional MRI, X-Ray detection, PET, CT imaging, immunohistochemistry, Western blot of tissues or cells, or by any other suitable detection method.

The term "detectable label" as used here means a molecule preferably selected from, but not limited to, fluorescent, enzyme, radioactive, metallic, biotin, chemiluminescent, and bioluminescent molecules. As used herein, a detectable label may be a colorimetric label, e.g., a chromophore molecule. In some aspects of the invention, a polypeptide or an antibody may be detectably labeled with a single or with two or more of the detectable labels set forth herein, or other art-known detectable labels.

Radioactive or isotopic labels may be, for example, $^{14}C$, $^{3}H$, $^{35}S$, $^{125}I$, and $^{32}P$. Fluorescent labels may be any compound that emits an electromagnetic radiation, preferably visible light, resulting from the absorption of incident radiation and persisting as long as the stimulating radiation is continued.

Examples of fluorescent labels that may be used on polypeptides and/or antibodies of the invention and in methods of the invention include but are not limited to 2,4-dinitrophenyl, acridine, CASCADE BLUE®, rhodamine, 4-benzoylphenyl, 7-nitrobenz-2-oxa-1,3-diazole, 4,4-difluoro-4-bora-3a,4a-diaza-3-indacene and fluorescamine. Absorbance-based labels may be molecules that are detectable by the level of absorption of various electromagnetic radiation. Such molecules may be, for example, the fluorescent labels indicated above.

Chemiluminescent labels in this invention refer to compounds that emit light as a result of a non-enzymatic chemical reaction. Methods of the invention may also include the use of a luminescent detectable diagnostic molecule such as enhanced green fluorescent protein (EGFP), luciferase (Luc), or another detectable expression product.

Enzymatic methods for detection may be used including the use of alkaline phosphatase and peroxidase. Additional enzymes may also be used for detection in methods and kits of the invention.

As used herein, fluorophores include, but are not limited to amine-reactive fluorophores that cover the entire visible and near-infrared spectrum. Examples of such fluorophores include, but are not limited to, 4-methylumbelliferyl phosphate, fluorescein isothiocyanate (FITC), tetramethylrhodamine isothiocyanate (TRITC), BODIPY® dyes; OREGON GREEN®, rhodamine green dyes; the red-fluorescent Rhodamine Red-X, TEXAS RED®dyes; and the UV light-excitable CASCADE BLUE®, Cascade Yellow, MARINA BLUE®, Pacific Blue™ and AMCA-X fluorophores. Fluorophores may also include non-fluorescent dyes used in fluorescence resonance energy transfer (FRET).

A labeled polypeptide or antibody of the invention can be prepared from standard moieties known in the art. As is recognized by one of ordinary skill in the art, the labeling process for preparing a detectable labeled polypeptide, antibody, or fragment thereof may vary according to the molecular structure of the polypeptide or antibody, respectively, and the detectable label. Methods of labeling polypeptides and/or antibodies with one or more types of detectable labels are routinely used and are well understood by those of ordinary skill in the art.

In some embodiments, it is contemplated that one may wish to first derivatize a polypeptide or antibody, and then attach the detectable label to the derivatized product. Suitable cross-linking agents for use in this manner include, for example, SPDP (N-succinimidyl-3-(2-pyridyldithio)propionate), and SMPT, 4-succinimidyl-oxycarbonyl-methyl-(2-pyridyldithio)toluene. In some embodiments, a radionuclide may be coupled to an antibody or antigen-binding fragment thereof by chelation.

Compositions (e.g., those that include antibodies to MCJ polypeptides and antibodies and derivatives/conjugates thereof, etc.) of the present invention may have diagnostic and therapeutic utilities. For example, these molecules can be administered to cells in culture, e.g. in vitro or ex vivo, or to a sample obtained from a subject to diagnose the drug-resistance status of a cell or subject with cancer. As detailed herein, antibodies or antigen-binding fragments thereof of the invention may be used for example to detect the presence of MCJ polypeptides in a sample from a cell, tissue or subject, thus permitting determination of the multidrug resistance status of the cell, tissue, or subject. Antibodies may be coupled to specific diagnostic labeling agents for imaging of the MCJ polypeptides or fragments thereof. The antibodies or antigen-binding fragments thereof of the invention may also be used for immunoprecipitation, immunoblotting MCJ using standard methods known to those of ordinary skill in the art.

In some embodiments, an antibody or antigen-binding fragment thereof of the invention that specifically binds to an MCJ polypeptide may be in solution or may be attached to a surface (e.g. a dipstick, microtiter plate, multiwell plate, plastic, slide, card, etc.). A sample from a subject may then be applied to the substrate and the substrate is then processed to assess whether specific binding occurs between the antibody and a polypeptide or other component of the sample. As used herein a substrate may be made of a material including any synthetic or natural material. Examples of substrates of the invention may include, but are not limited to: glass, plastic, nylon, metal, paper, cardboard, filter paper, filter membranes, etc., and can be in numerous forms including, but not limited to, tubes, centrifuge tubes, cuvettes, cards, slides, dipsticks, beads, coverslips, multiwell plates, Petri plates, etc. One of ordinary skill in the art will recognize that numerous additional types of surfaces can be used in the methods of the invention.

As will be understood by one of skill in the art, a binding assay using an antibody of the invention may also be performed in solution by contacting a sample from a subject with an antibody or antigen-binding fragment thereof of the invention when the antibody or antigen-binding fragment thereof, for example in a 96-well plate, a tube, a drop on a slide, etc.

As used herein the term "attached to a surface" means chemically or biologically linked to the surface and not freely removable from a surface. Examples of attachment, though not intended to be limiting are covalent binding between the substrate and an antibody, attachment via specific biological binding, or the like. For example, "attached" in this context includes chemical linkages, chemical/biological linkages, etc. As used herein the term "covalently attached" means attached via one or more covalent bonds. As used herein the term "specifically attached" means an antibody or fragment thereof is chemically or biochemically linked to a surface as described above with respect to the definition of "attached," but excluding all non-specific binding. In the methods of the invention, an antibody that is attached to a substrate is attached such that the antibody is not removable from the substrate without specific stripping methods or solutions. Such stripping methods may include, but are not limited to, physical methods such as scraping or heating, enzymatic methods, and chemical methods, which may include but are not limited to contacting the attached antibody and substrate with a solution such that the link between the substrate and the surface is broken and the substrate is released.

In some embodiments of the invention, an antibody or antigen-binding fragment thereof is attached to a substrate, for example a dipstick, and is contacted with a sample cell or tissue from culture or from a subject. The surface of the substrate may then be processed using procedures well known to those of skill in the art, to assess whether specific binding occurred between the antibody and an MCJ polypeptide in the subject's sample. For example, procedures may include, but are not limited to, contact with a secondary antibody, or other method that indicates the presence of specific binding.

The invention, in some aspects, includes various assays to determine levels of MCJ polypeptide. Methods of the invention that are useful to determine levels of MCJ polypeptide in cells, tissues, subjects, and samples (e.g., from subjects, in culture, etc.), include, but are not limited to: binding assays, such as described in the examples below; specific binding assays, such as using antibodies or antigen-binding fragments thereof of the invention that bind specifically to MCJ polypeptide; gel electrophoresis; mass spectrometry; NMR; and the like. Immunoassays may be used according to the invention including, but not limited to, sandwich-type assays, competitive binding assays, one-step direct tests and two-step tests such as described in the examples. Assessment of binding of antibodies that specifically bind MCJ polypeptide may also be done in vivo—in living subjects using art-known detectable labels and suitable in vivo methods.

Methods and assays of the invention (e.g. binding assays, gel electrophoresis; mass spectrometry; NMR; and the like) may be used to monitor changes in MCJ levels in cell sample and or a subject over time. Thus, methods of the invention may be used to examine changes in MCJ levels in a subject or cell sample (e.g., cell culture) over time. This allows monitoring of MCJ levels in a subject who to undergo treatment for cancer and also enables to monitoring in a subject who is currently undergoing therapy for cancer. Thus, methods of the invention may be used to diagnose or assess cancer in a subject and may also be used to assess the efficacy of a therapeutic treatment of cancer for assessment of the level of MCJ in a subject at various time points. For example, a level of a subject's MCJ can be obtained prior to the start of a therapeutic regimen (either prophylactic or as a treatment of cancer), during the treatment regimen and/or after a treatment regimen, thus providing information on the multidrug resistance status in the patient. Assessment of efficacy of candidate therapeutic agents to modulate (e.g. increase) expression of MCJ in a cell or tissue may also be done using assays of the invention in cells from culture—e.g., as screening assays to assess candidate therapeutic agents to modulate levels of MCJ. Therapeutic agents that alter levels of MCJ in a cell, tissue, or subject may be used in the treatment of cancer, or as a pretreatment for cancer (e.g., to prepare a cell or subject for subsequent treatment).

It will be understood that a therapeutic regimen may be either prophylactic or a treatment of a cancer in a subject. Thus, methods of the invention may be used to monitor a subject's response to prophylactic therapy and/or treatment for cancer provided to a subject. Methods of the invention (e.g. binding assays, gel electrophoresis; mass spectrometry; NMR; and the like) may also be useful to monitor the onset, progression, or regression of multidrug resistance in a subject with cancer. The level of MCJ may be determined in two, three, four, or more samples obtained from a subject at separate times. The level of MCJ in the samples may be compared and changes in the levels over time may be used to assess the status and stage of multidrug resistance in the subject (or in a cell or tissue sample) and/or the effect of a treatment strategy on multidrug resistance in a subject (or a cell or tissue sample).

One aspect of the present invention relates to the use of the antibodies and/or antigen-binding fragments thereof of the invention for detecting MCJ polypeptide or fragments thereof in an in vitro or in vivo sample (e.g., histological or cytological specimens, real-time in vivo assays, biopsies and the like), and, in particular, to determine the level of MCJ in a cell or subject. This method involves providing an antibody or an antigen-binding binding fragment thereof, which specifically binds to MCJ to a cell or subject. The anti-MCJ antibody may be bound to a label that permits the detection of the MCJ. In some embodiments, a sample may be contacted with a labeled anti-MCJ antibody under conditions effective to permit binding of the anti-MCJ antibody to MCJ in the sample. The presence and/or amount of MCJ in the sample may be detected by detection of the label. In some embodiments, the contact between the anti-MCJ antibody and a cell is carried out in a sample from a subject or from cells in culture. In certain embodiments, contact between an anti-MCJ antibody and a cell may be carried out in a subject. Samples to which the methods of the invention can be applied include tissue samples, cell samples, including cell culture samples, subject samples, in vivo samples, etc.

Anti-MCJ antibodies of the present invention can be used in immunohistochemical techniques to examine tissue and cell specimens. In some embodiments, the samples are fresh samples. In some embodiments, slides containing cryostat sections of frozen, unfixed tissue biopsy samples or cytological smears are air dried, formalin or acetone fixed, and incubated with an antibody preparation in a humidified chamber at room temperature. The slides are then washed and further incubated with a preparation of a secondary antibody directed against the antibody. This secondary antibody may be tagged with a detectable compound, for instance a fluorescent compound such as rhodamine or fluorescein isothiocyanate, that fluoresces at a particular wavelength. The staining pattern and intensities within the sample are then determined by standard imaging methods such as microscopy and optionally photographically recorded.

As yet another alternative, computer enhanced fluorescence image analysis or flow cytometry can be used to examine tissue specimens or cells using the anti-MCJ antibodies of the invention.

Antibodies and/or antigen-binding fragments thereof of the present invention can be used to screen patients for diseases associated with the presence of reduced levels of MCJ. As used herein, the term "reduced" means lower, for example reduced versus a control level. Antibodies and antigen-binding fragments thereof of the invention may be used to identify the status of MCJ expression by assessing the level of MCJ in a sample from a subject or culture that has HD. Antibodies of the invention are particularly useful in assays to detect whether or not a subject has multidrug resistance, because a reduced level of MCJ protein in cancer cells correlates with multidrug resistance and a poorer prognosis. The amount or level of MCJ in a sample, as compared to a control, can be used to determine the presence multidrug resistance in a cell, cell culture or subject. Antibodies of the invention can be used to obtain useful prognostic information by providing an indicator of multidrug resistance and can be used to select a therapy for the subject, for example, to select a therapy.

The step of contacting an antibody or antigen-binding fragment thereof of the invention with a sample to be tested can be carried out in a cell or tissue sample to detect the presence of MCJ protein in the sample. It is preferred that an antibody or antigen-binding fragment thereof of the invention recognize substantially no antigens in the sample other than MCJ. In some embodiments, it is preferred that the antibody or antigen-binding fragment thereof of the invention recognize substantially no antigens in the sample other than a amino acid sequence of MCJ that comprises the sequence MAARGVI-APVGESLRYAEYL (SEQ ID NO:2).

Antibodies and antigen-binding fragments thereof suitable for detecting MCJ protein and polypeptides include anti-MCJ antibodies, such as monoclonal or polyclonal antibodies. In addition, antibody fragments, half-antibodies, hybrid derivatives, probes, and other molecular constructs may be utilized. In some embodiments of the invention, antibodies are antibodies generated against the sequence MAARGVI-APVGESLRYAEYL (SEQ ID NO: 2).

Antibodies or antigen-binding fragments thereof of the invention may also be used in a variety of assays based upon detecting levels of MCJ protein in cells and/or subjects. Assays include (1) characterizing the impact of MCJ levels on cancer treatment in a subject; (2) evaluating a treatment to alter MCJ levels in a subject; (3) selecting a treatment for cancer based in part on the level of MCJ in cells of the subject; and (4) determining the status of cancer and/or multidrug resistance in a subject. Thus, subjects can be characterized, treatment regimens can be monitored, treatments can be selected and diseases status can be better understood using the assays of the present invention. For example, the antibodies or antigen-binding fragments thereof of the invention are useful in one aspect in methods for measuring the level of MCJ in a cell and/or subject, which is a direct indicator of multidrug resistance and potential drug efficacy in a cell and/or subject. The impact of the level of MCJ thus can be measured due to the negative correlation between the level of MCJ and the presence of multidrug resistance in cells, tissues, and/or subjects with cancer. The level of MCJ thus may correlate with the status of cancer and multidrug resistance in a subject. Relatively low levels of MCJ may reflect the presence of multidrug resistance and normal or high levels of MCJ may indicate a lack of multidrug resistance and/or an increase in efficacy of one or more cancer drugs in the treatment of cancer.

Antibodies and antigen-binding fragments thereof of the invention may be used in assays described herein, which are carried out in cells from culture, cells in solution, and/or on samples obtained from subjects and/or samples in a subject (in vivo sample). As used herein, a subject is a human, non-human primate, cow, horse, pig, sheep, goat, dog, cat, or rodent. In all embodiments, human subjects are preferred. The samples used herein are any cell or tissue sample, and may include neuronal cell and/or tissue samples.

Particularly important subjects to which the present invention can be applied are subjects with cancer. The term "subject with cancer" as used herein, means an individual who, at the time the sample is taken, has been diagnosed as having cancer. Methods and antibodies of the invention may also be used to detect abnormal levels of MCJ in subjects that are not yet diagnosed with cancer.

Cancers that may be assessed and treated using methods and compositions of the invention include, but are not limited to, breast cancer, ovarian cancer, (including, but not limited to those arising from epithelial cells, stromal cells, germ cells and mesenchymal cells), biliary tract cancer, brain cancer (including glioblastomas and medulloblastomas), cervical cancer, choriocarcinoma, colon cancer, endometrial cancer, esophageal cancer, gastric cancer, intraepithelial neoplasms (including Bowen's disease and Paget's disease), liver cancer, lung cancer, neuroblastomas, oral cancer (including squamous cell carcinoma), pancreatic cancer, prostate cancer, rectal cancer, renal cancer (including adenocarcinoma and Wilms tumor), sarcomas (including leiomyosarcoma, rhabdomyosarcoma, liposarcoma, fibrosarcoma and osteosarcoma), skin cancer (including melanoma, Kaposi's sarcoma, basocellular cancer and squamous cell cancer), testicular cancer including germinal tumors (seminomas, and non-seminomas such as teratomas and choriocarcinomas), stromal tumors, germ cell tumors, and thyroid cancer (including thyroid adenocarcinoma and medullary carcinoma).

Assays described herein may include the use of antibodies or antigen-binding fragments thereof of the invention and may involve measuring levels of MCJ. Levels of MCJ can be determined in a number of ways when carrying out the various methods of the invention. In one particularly important measurement, a level of MCJ is measured in relation to a control level of MCJ in a cell, tissue or subject. One possible measurement of the level of MCJ is a measurement of absolute levels of MCJ. This could be expressed, for example, in MCJ per unit of cells or tissue. Another measurement of the level of MCJ is a measurement of the change in the level of MCJ over time. This may be expressed in an absolute amount or may be expressed in terms of a percentage increase or decrease over time. Antibodies or antigen-binding fragments of the invention may be used in diagnostic methods alone or in conjunction with certain antibodies already known in the art. Known antibodies may include antibodies that specifically bind to other proteins that are cancer-associated or other cell marker proteins that may be used to quantitate the level of MCJ per unit of cancer cells, etc.

Importantly, levels of MCJ can be determined using the antibodies or antigen-binding fragments thereof of the invention and are advantageously compared to controls according to the invention. The control may be a predetermined value, which can take a variety of forms. It can be a single cut-off value, such as a median or mean. It can be established based upon comparative groups, such as in groups having normal amounts of MCJ and groups having abnormal amounts of MCJ. Another example of comparative groups may be groups having cancer or cancer symptoms and groups without cancer or cancer symptoms. Another comparative group may be a group with a family history of cancer and a group without such a family history. A predetermined value can be arranged, for example, where a tested population is divided equally (or unequally) into groups, such as a low-risk group, a medium-risk group and a high-risk group or into quadrants or quintiles, the lowest quadrant or quintile being individuals with the lowest risk (e.g. of multidrug resistance) and highest amounts of MCJ and the highest quadrant or quintile being individuals with the highest risk (e.g. of multidrug resistance) and lowest amounts of MCJ.

The predetermined value, of course, will depend upon the particular population selected. For example, an apparently healthy population will have a different 'normal' range than will a population that is known to have a condition related to abnormal MCJ protein expression or presence. Accordingly, the predetermined value selected may take into account the category in which an individual or cell falls. Appropriate ranges and categories can be selected with no more than routine experimentation by those of ordinary skill in the art. As used herein, "abnormal" means not normal as compared to a control. By abnormally high it is meant high relative to a selected control. Typically the control will be based on apparently healthy normal individuals in an appropriate age bracket or apparently healthy cells.

It will be understood that controls according to the invention may be, in addition to predetermined values, samples of materials tested in parallel with the experimental materials. Examples include samples from control populations or control samples generated through manufacture to be tested in parallel with the experimental samples.

As mentioned above, it is also possible to use the antibodies or antigen-binding fragments thereof of the invention to characterize MCJ levels by monitoring changes in the amount of MCJ over time. For example, it is expected that a decrease MCJ correlates with increase of multidrug resistance cells and/or tissues. Accordingly one can monitor levels of MCJ over time to determine if there is a change in multidrug resistance status in a subject or in a cell culture. Changes in levels of MCJ greater than 0.1% may indicate an abnormality. Preferably, the reduction in MCJ levels, which indicates an abnormality, is a reduction greater than 0.2%, greater than 0.5%, greater than 1.0%, 2.0%, 3.0%, 4.0%, 5.0%, 7.0%, 10%, 15%, 20%, 25%, 30%, 40%, 50%, or more. Decreases in the amount of MCJ over time may indicate a change in multidrug resistance status in a sample or subject.

The antibodies or antigen-binding fragments thereof of the invention may also be used in diagnostic methods to determine the effectiveness of treatments for altering multidrug resistance and/or treating cancer. "Evaluation of treatment" as used herein, means the comparison of a subject's levels of MCJ measured in samples obtained from the subject at different sample times, preferably at least one day apart. In some embodiments, the time to obtain the second sample from the subject is at least 5, 10, 20, 30, 40, 50, minutes after obtaining the first sample from the subject. In certain embodiments, the time to obtain the second sample from the subject is at least 1, 2, 3, 4, 5, 6, 7, 8, 9, 10, 11, 12, 13, 14, 15, 16, 17, 18, 19, 20, 21, 22, 23, 24, 36, 48, 72, 96, 120 or more hours after obtaining the first sample from the subject.

Antibodies or antigen-binding fragments thereof of the invention may be used to allow the comparison of levels of MCJ in two or more samples, taken at different times, which, may be used to detect the status of multidrug resistance in a subject and allows evaluation of a cancer treatment as well as evaluation of a treatment for multidrug resistance. The comparison of a subject's levels of MCJ measured in samples obtained at different times and/or on different days provides a measure of multidrug resistance that can be used to determine the effectiveness of any treatment for cancer or treatment to regulate MCJ levels in a subject. Those of ordinary skill in the art will recognize that similar assessment of candidate therapeutics can be tested in vitro by assessing any change in MCJ levels that occurs in response to contact of the cell with a candidate agent for treatment of cancer or with a candidate agent for the modulation of MCJ levels.

As will be appreciated by those of ordinary skill in the art, the evaluation of a treatment also may be based upon an evaluation of the symptoms or clinical end-points of cancer. Thus, the antibodies or antigen-binding fragments thereof of the invention are useful for determining the onset, progression or regression of a condition that is characterized by the reduction in the levels of MCJ in a cell and/or subject. In some instances, antibodies or antigen-binding fragments thereof of the invention can be used to detect levels of MCJ and multidrug resistance in subjects diagnosed as having cancer. In other instances, antibodies or antigen-binding fragments thereof of the invention can be used to obtain measurements that represent the diagnosis of multidrug resistance in a subject with cancer. In some instances, a subject may be already be undergoing drug therapy for cancer, while in other instances a subject may be without present cancer therapy.

In this aspect of the invention, the type of treatment, (e.g., treatment with drugs such as anthracyclines and taxanes, to which multidrug resistance may be exhibited, or treatment with 5-fluorouracil (5-FU), to which cells do not demonstrate multidrug resistance) are based upon selecting subjects who have abnormally low levels of MCJ. Treatments may include administration of a particular type of anti-cancer drug based on the presence or absence of an indication of multidrug resistance, or administration of a candidate therapeutic or drug to increase the level of MCJ in cells, tissues, and/or subjects. Such subjects may already be receiving a drug for treating cancer. It may be appropriate according to the invention to alter a therapeutic regimen for a subject, based upon the measurement of the level of MCJ using an antibody or antigen-binding fragment thereof of the invention. This can be understood in connection with treatment of cancer. A subject may be free of any present treatment for cancer and monitoring of MCJ levels may allow selection of the most efficacious treatment regimen and/or may identify the subject as a candidate for a treatment to increase the level of MCJ. Thus, subjects may be selected and treated with elevated levels of the same drugs or with different therapies as a result of assays that utilize the antibodies or antigen-binding fragments thereof of the invention.

According to the present invention, some subjects may be free of symptoms otherwise calling for treatment with a particular therapy, and testing with an anti-MCJ antibody of the invention may identify the subject as needing treatment. This means that absent the use of the antibodies or antigen-binding fragments thereof of the invention to assess levels of MCJ, the subject would not according to convention as of the date of the filing of the present application have symptoms calling for treatment with a particular therapy. As a result of measuring the level of MCJ of the subject, the subject become a candidate for treatment with a particular therapy. Thus, for example, treatment for a subject with a low level of MCJ may be selected to be 5-FU and treatment for a subject with a normal level of MCJ may be selected to be an anthracycline and/or taxane. Those of ordinary skill in the art will recognize that alternative drug therapies that are known to be efficacious in the presence of multidrug resistance may be selected based on the detection of MCJ levels in a cell, tissue, and/or subject.

In a subject in which an abnormally low level of MCJ is detected, an effective amount of a composition to increase the level of MCJ or other treatment is that amount effective to increase the level of MCJ in the subject. The drug (e.g., composition) for increasing the level of MCJ present in a cell, tissue, and/or subject may be administered in an effective amount. Typically an effective amount of an drug to increase MCJ will be determined in clinical trials, establishing an effective dose for a test population versus a control population in a blind study. In some embodiments, an effective amount will be that results in a desired response, e.g., an amount that diminishes multidrug resistance in cells or tissues in a subject with cancer. Thus, an effective amount may be the amount that when administered increases the amount of MCJ in the subject to an amount that that is above the amount that would occur in the subject or tissue without the administration of the composition. In the case of treating multidrug resistance in cancer, the desired response is reducing or eliminating multidrug resistance in the cell, tissue, and/or subject. This may involve only making a cell and/or tissue more responsive to the drugs to which the multidrug resistance is directed temporarily, although more preferably, it involves halting the progression of the multidrug resistance permanently. This can be monitored by using the antibodies of the invention using diagnostic methods presented herein. The desired response to treatment of the disease or condition also can be delaying the onset or even preventing the onset of the disease or condition.

Effective amounts of composition that increases MCJ levels (also referred to herein as a pharmaceutical compound) may also be determined by assessing physiological effects of administration on a cell or subject, such as a decrease of multidrug resistance following administration. Other assays will be known to one of ordinary skill in the art and can be employed for measuring the level of the response to a treatment. The amount of a treatment may be varied for example by increasing or decreasing the amount of a therapeutic composition, by changing the therapeutic composition administered, by changing the route of administration, by changing the dosage timing and so on. The effective amount will vary with the particular condition being treated, the age and physical condition of the subject being treated; the severity of the condition, the duration of the treatment, the nature of the concurrent therapy (if any), the specific route of administration, and the like factors within the knowledge and expertise of the health practitioner. For example, an effective amount may depend upon the degree to which an individual has abnormally low levels of MCJ.

Effective amounts will also depend, of course, on the particular condition being treated, the severity of the condition, the individual patient parameters including age, physical condition, size and weight, the duration of the treatment, the nature of concurrent therapy (if any), the specific route of administration and like factors within the knowledge and expertise of the health practitioner. These factors are well known to those of ordinary skill in the art and can be addressed with no more than routine experimentation. It is generally preferred that a maximum dose of an composition to increase the level of MCJ (alone or in combination with other therapeutic agents) be used, that is, the highest safe dose according to sound medical judgment. It will be understood by those of ordinary skill in the art, however, that a patient may insist upon a lower dose or tolerable dose for medical reasons, psychological reasons or for virtually any other reasons.

A pharmaceutical compound dosage may be adjusted by the individual physician or veterinarian, particularly in the event of any complication. A therapeutically effective amount typically varies from 0.01 mg/kg to about 1000 mg/kg, preferably from about 0.1 mg/kg to about 200 mg/kg, and most preferably from about 0.2 mg/kg to about 20 mg/kg, in one or more dose administrations daily, for one or more days.

The absolute amount will depend upon a variety of factors, including the material selected for administration, whether the administration is in single or multiple doses, and individual subject parameters including age, physical condition, size, weight, and the stage of the disease or condition. These factors are well known to those of ordinary skill in the art and can be addressed with no more than routine experimentation.

Pharmaceutical compounds of the invention may be administered alone, in combination with each other, and/or in combination with other drug therapies, or other treatment regimens that are administered to subjects with cancer.

A pharmaceutical compositions used in the foregoing methods preferably are sterile and contain an effective amount of a therapeutic compound that will increase the level of a MCJ polypeptide for a level that produces the desired response in a unit of weight or volume suitable for administration to a patient.

The doses of a composition to increase the level of MCJ that is administered to a subject can be chosen in accordance with different parameters, in particular in accordance with the mode of administration used and the state of the subject. Other factors include the desired period of treatment. In the event that a response in a subject is insufficient at the initial doses applied, higher doses (or effectively higher doses by a different, more localized delivery route) may be employed to the extent that patient tolerance permits.

Various modes of administration will be known to one of ordinary skill in the art which effectively deliver a composition to increase the level of MCJ protein to a desired tissue, cell or bodily fluid. Methods for administering such a composition, or other pharmaceutical compound of the invention may be topical, intravenous, oral, intracavity, intrathecal, intrasynovial, buccal, sublingual, intranasal, transdermal, intravitreal, subcutaneous, intramuscular and intradermal administration. The invention is not limited by the particular modes of administration disclosed herein. Standard references in the art (e.g, *Remington's Pharmaceutical Sciences*, 18th edition, 1990) provide modes of administration and formulations for delivery of various pharmaceutical preparations and formulations in pharmaceutical carriers. Other protocols which are useful for the administration of therapeutic compound of the invention will be known to one of ordinary skill in the art, in which the dose amount, schedule of administration, sites of administration, mode of administration (e.g., intra-organ) and the like vary from those presented herein.

Administration of a composition to increase MCJ levels to mammals other than humans, and administration and use of anti-MCJ antibodies or fragments thereof of the invention, e.g. for testing purposes or veterinary therapeutic purposes, is carried out under substantially the same conditions as described above. It will be understood by one of ordinary skill in the art that this invention is applicable to both human and animal cancers. Thus this invention is intended to be used in husbandry and veterinary medicine as well as in human therapeutics.

When administered, the pharmaceutical preparations of the invention are applied in pharmaceutically-acceptable amounts and in pharmaceutically-acceptable compositions. The term "pharmaceutically acceptable" means a non-toxic material that does not interfere with the effectiveness of the biological activity of the active ingredients. Such preparations may routinely contain salts, buffering agents, preservatives, compatible carriers, and optionally other therapeutic agents. When used in medicine, the salts should be pharmaceutically acceptable, but non-pharmaceutically acceptable salts may conveniently be used to prepare pharmaceutically-acceptable salts thereof and are not excluded from the scope of the invention. Such pharmacologically and pharmaceutically-acceptable salts include, but are not limited to, those prepared from the following acids: hydrochloric, hydrobromic, sulfuric, nitric, phosphoric, maleic, acetic, salicylic, citric, formic, malonic, succinic, and the like. Also, pharmaceutically-acceptable salts can be prepared as alkaline metal or alkaline earth salts, such as sodium, potassium or calcium salts. Preferred components of the composition are described above in conjunction with the description of the MCJ polypeptides of the invention.

An composition that increases MCJ levels may be combined, if desired, with a pharmaceutically-acceptable carrier. The term "pharmaceutically-acceptable carrier" as used herein means one or more compatible solid or liquid fillers, diluents or encapsulating substances which are suitable for administration into a human. The term "carrier" denotes an organic or inorganic ingredient, natural or synthetic, with which the active ingredient is combined to facilitate the application. The components of the pharmaceutical compositions also are capable of being co-mingled with additional cancer drug formulations in a manner such that there is no interaction which would substantially impair the desired pharmaceutical efficacy.

A pharmaceutical composition of the invention may contain suitable buffering agents, as described above, including: acetate, phosphate, citrate, glycine, borate, carbonate, bicarbonate, hydroxide (and other bases) and pharmaceutically acceptable salts of the foregoing compounds.

A pharmaceutical composition of the invention, also may contain, optionally, suitable preservatives, such as: benzalkonium chloride; chlorobutanol; parabens and thimerosal. The pharmaceutical compositions may conveniently be presented in unit dosage form and may be prepared by any of the methods well-known in the art of pharmacy. All methods include the step of bringing the active agent into association with a carrier which constitutes to one or more accessory ingredients. In general, the compositions are prepared by uniformly and intimately bringing the active compound into association with a liquid carrier, a finely divided solid carrier, or both, and then, if necessary, shaping the product.

Compositions suitable for oral administration may be presented as discrete units, such as capsules, tablets, lozenges, each containing a predetermined amount of the active compound. Other compositions include suspensions, in aqueous liquids or non-aqueous liquids such as a syrup, elixir or an emulsion.

Compositions suitable for parenteral administration may include a compound that increases a level of MCJ in cells, tissues, and/or subjects. This preparation may be formulated according to known methods using suitable dispersing or wetting agents and suspending agents. The sterile injectable preparation also may be a sterile injectable solution or suspension in a non-toxic parenterally-acceptable diluent or solvent, for example, as a solution in 1,3-butane diol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono-or di-glycerides. In addition, fatty acids such as oleic acid may be used in the preparation of injectables. Carrier formulation suitable for oral, subcutaneous, intravenous, intramuscular, etc. administrations can be found in *Remington's Pharmaceutical Sciences*, Mack Publishing Co., Easton, Pa.

Also within the scope of the invention are kits comprising the compositions of the invention and instructions for use. The kits can further contain at least one additional reagent, such as one or more additional antibodies of the invention (e.g., an antibody having a complementary activity which binds to an epitope in an MCJ polypeptide distinct from the first antibody).

Kits containing antibodies or antigen-binding fragments thereof of the invention can be prepared for in vitro diagnosis, prognosis and/or monitoring the level of MCJ in cells, tissues, and/or subjects using immunohistological, immunocytological and/or immunoserological methods described above. Components of the kits can be packaged either in aqueous medium or in lyophilized form. When the antibodies or antigen-binding fragments thereof are used in the kits in the form of conjugates in which a label moiety is attached, such as an enzyme or a radioactive metal ion, the components of such conjugates can be supplied either in fully conjugated form, in the form of intermediates or as separate moieties to be conjugated by the user or the kit. In some embodiments of a kit of the invention, an antibody or antigen-binding fragment thereof may be attached to a substrate, for example a dipstick, card, slide, plate, dish, tube, vial, etc.

A kit may comprise a carrier being compartmentalized to receive in close confinement therein one or more container means or series of container means such as test tubes, vials, flasks, bottles, syringes, or the like. A first of said container means or series of container means may contain one or more anti-MCJ antibodies or antigen-binding fragments thereof or an MCJ polypeptide. A second container means or series of container means may contain a label or linker-label intermediate capable of binding to the primary anti-MCJ antibodies (or fragment thereof).

A kit of the invention may also include instructions. Instructions typically will be in written form and will provide guidance for carrying-out the assay embodied by the kit and for making a determination based upon that assay.

MCJ polypeptides, and antibodies and antigen-binding fragments of the invention may also be useful in methods of screening for candidate agents that modulate levels of MCJ polypeptides in cells, tissues, and/or subjects. Methods can include mixing the candidate agent with cells or tissues or in a subject and using the antibodies of the invention to determine the level of MCJ before and after contact with the candidate agent. An increase in the amount of MCJ in comparison to a control is indicative of an agent capable of increasing the level of MCJ. An increase in the amount of MCJ in a subject known to have cancer and/or multidrug resistance in comparison to a control is indicative of that the candidate agent/compound is capable of increasing the level of MCJ and may be useful to reduce and/or eliminate multidrug resistance in cells, tissues, and/or subjects.

The assay mixture comprises a candidate agent. The candidate agent is preferably an antibody, a small organic compound, or a polypeptide, and accordingly can be selected from combinatorial antibody libraries, combinatorial protein libraries, or small organic molecule libraries. Typically, a plurality of reaction mixtures are run in parallel with different agent concentrations to obtain a different response to the various concentrations. Typically, one of these concentrations serves as a negative control, i.e., at zero concentration of agent or at a concentration of agent below the limits of assay detection.

Candidate agents encompass numerous chemical classes, although typically they are organic compounds, proteins or antibodies (and fragments thereof that bind antigen). In some preferred embodiments, the candidate agents are small organic compounds, i.e., those having a molecular weight of more than 50 yet less than about 2500, preferably less than about 1000 and, more preferably, less than about 500. Candidate agents comprise functional chemical groups necessary for structural interactions with polypeptides and/or nucleic acids, and typically include at least an amine, carbonyl, hydroxyl, or carboxyl group, preferably at least two of the functional chemical groups and more preferably at least three of the functional chemical groups. The candidate agents can comprise cyclic carbon or heterocyclic structure and/or aromatic or polyaromatic structures substituted with one or more of the above-identified functional groups. Candidate agents also can be biomolecules such as polypeptides, saccharides, fatty acids, sterols, isoprenoids, purines, pyrimidines, derivatives or structural analogs of the above, or combinations thereof and the like.

Candidate agents are obtained from a wide variety of sources including libraries of synthetic or natural compounds. For example, numerous means are available for random and directed synthesis of a wide variety of organic compounds and biomolecules, including expression of randomized oligonucleotides, synthetic organic combinatorial libraries, phage display libraries of random or non-random polypeptides, combinatorial libraries of proteins or antibodies, and the like. Alternatively, libraries of natural compounds in the form of bacterial, fungal, plant, and animal extracts are available or readily produced. Additionally, natural and synthetically produced libraries and compounds can be readily modified through conventional chemical, physical, and biochemical means. Further, known agents may be subjected to directed or random chemical modifications such as acylation, alkylation, esterification, amidification, etc. to produce structural analogs of the agents.

A variety of other reagents also can be included in the mixture. These include reagents such as salts, buffers, neutral proteins (e.g., albumin), detergents, etc., which may be used to facilitate optimal protein-protein and/or protein-agent binding. Such a reagent may also reduce non-specific or background interactions of the reaction components. Other reagents that improve the efficiency of the assay such as protease inhibitors, nuclease inhibitors, antimicrobial agents, and the like may also be used.

The order of addition of components, incubation temperature, time of incubation, and other parameters of the assay may be readily determined. Such experimentation merely involves optimization of the assay parameters, not the fundamental composition of the assay. Incubation temperatures typically are between 4° C. and 40° C. Incubation times preferably are minimized to facilitate rapid, high throughput screening, and typically are between 0.1 and 10 hours. After incubation, the presence or absence of and/or the level of MCJ is detected by any convenient method available to the user.

For example, the level of MCJ can be determined through the measure of a detectable label using standard methods and as described herein.

EXAMPLES

Example 1

Chemotherapy (e.g., anthracyclines and taxanes) is one of the most effective and widely used treatments for breast cancer. However, the response to these drugs varies among individuals and no predictive markers are available. It has now been shown that MCJ is expressed in drug-sensitive breast cancer cells, but its expression is lost in multidrug resistant cells. More importantly, inhibition of MCJ expression induces multidrug resistance by inducing c-Jun-mediated ABCB1 transporter expression and preventing intracellular accumulation of chemotherapeutic drugs. Methylation of MCJ gene has been correlated with poor response of ovarian cancer patients to chemotherapy and results presented herein suggest that MCJ could also be used as a marker for chemotherapy response in breast cancer. These findings have direct implications in the breast cancer chemotherapy.

It is also now shown herein that MCJ is a Golgi localized, type II transmembrane DnaJ protein that arose in vertebrates as a result of gene duplication. Results provided herein demonstrate that MCJ is required to repress the expression of the ABCB1 drug transporter in breast cancer cells. Loss of MCJ expression leads to increased levels of c-Jun protein that triggers the expression of ABCB1 and thereby multidrug resistance.

Methods
Cell Culture.

MCF7 and MCF7/ADR cells were a kind gift from Dr. Ken Cowan (National Cancer Institute, Bethesda, Md.). MCF7, MCF7/ADR, MCF7/siMCJ-1B MCF7/siMCJ-3B, MDA-MB-321, MD22, MES-SA and MES-Dx5 cells were maintained in RPMI-1640 (Life technologies, Inc., Gaithersburg, Md.) containing 5% FBS (Hyclone, Logan, Utah), Penicillin/streptomycin and 1-glutamine (Gibco). 293T cells were cultured in DMEM-F12 medium (Life technologies, Inc.) supplemented with 10% FBS (Hyclone, Logan, Utah).

Plasmids.

The siMCJ targeting construct was generated using the human H1-RNA-polymerase III promoter (Brummelkamp et al., *Science* 296, 550-553, 2002) cloned into the pCMV-EGFP-N1 vector (Invitrogen, Carlsbad, Calif.) upstream of the CMV-EGFP cassette to obtain the pSuper-EGFP vector. The siRNA for MCJ 5'-gatccccGAAGATTTCAACTC-CTAGCttcaagagaGCTAGGAGT-TGAAATCTTCatttggaag-3 (SEQ ID NO:21); Sigma Genosys, Woodlands, Tex.) was cloned into the BglII and HindIII-sites downstream of the H1-promoter. The human MCJ target sequences are shown in capital letters. The pEGZ-HA-MCJ expressing plasmid was generated by cloning MCJ downstream of HA-tag in pEGZ plasmid containing the IRES-EGFP.

Transient and Stable Transfection.

For transient transfection, cells were transfected using LIPOFECTAMINE® 2000 as recommended by the manufacturer (Invitrogen, Carlsbad, Calif.). For stable transfection, the above procedure was followed and clones were selected in medium containing 400 μg/ml of G418 (Life technologies, Inc) as described (Conze et al., Cancer Res 61, 8851-8858, 2001). 293T cells were transfected using calcium phosphate.

Luciferase Assay.

MCF7, MCF7/siMCJ-1B and -3B cells were co-transfected with AP-1-luciferase reporter construct and pCMV-.beta.-Gal plasmids using LIPOFECTAMINE® 2000. After 24 h, the cells were washed, trypsinized, lyzed and relative luciferase activity was determined as recommended by the manufacturer (Promega, Madison, Wis.) using TD-20/20 Luminometer (Turner Biosystems, Inc, Sunnyvale, Calif.). Luciferase activity was normalized to .beta.-galactosidase activity as control for transfection efficiency.

Cell Viability Assay (MTT Assay).

The dose response of cell line to different drugs was determined by MTT assay as described previously (Conze et al., Cancer Res 61, 8851-8858, 2001; Sladowski et al., J Immunol Methods 157, 203-207, 1993). Different concentrations of drug were used, ranging from 0-100 μM for Doxorubicin, 0-30 μM for Paclitaxel and 0-30 μM for 5-Flurouracil. $LD_{50}$ values were calculated by non-linear regression and plotted graphically as percentage of viable cells.

Analysis of Drug Internalization.

Flow Cytometry.

Figure 10:
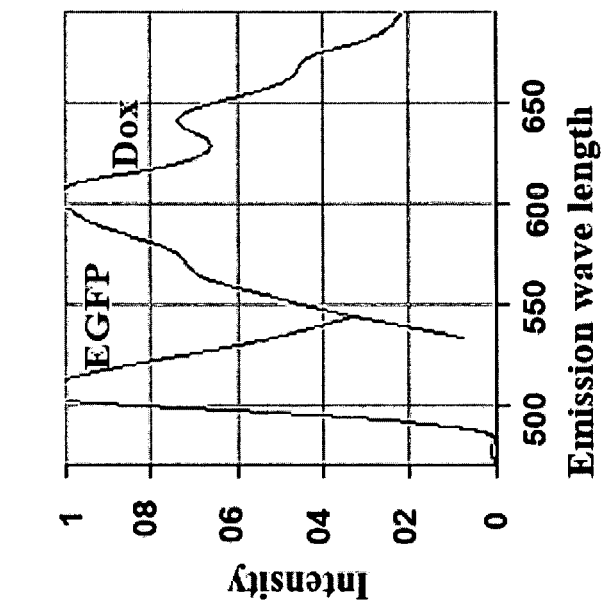
FIG. 10 is a graph of emission spectral analysis. EGFP and doxorubicin emission in MCF7 cells were measured using lambda mode on a Zeiss LSM 510 META confocal microscope. The cells were excited by the 488 nm wavelength line of an argon laser, and emission signals were acquired using the lambda imaging mode.

MCF7, MCF7/ADR, MCF7/siMCJ-1B and MCF7/siMCJ-3B cells were treated with doxorubicin (0.3 or 3 μM) for 3 h at 37° C. Negative controls had no drug added. Cells were washed 3 times with PBS and trypsinised and doxorubicin fluorescence was examined by flow cytometry using a LSRII flow cytometer (BD Biosciences, Mass.). FLP3, 695/40 nm filter with 685 nm long pass was used to measure doxorubicin fluorescence. For MCF7/siMCJ cells, EGFP was detected in FLP1, 530/30 nm band-pass with 505 nm long pass. No overlap of two fluorescences could be detected. Confocal microscopy: MCF7, MCF7/ADR, MCF7/siMCJ-1B and -3B ($3\times10^4$) cells were seeded on BD Biocoat coverslips (BD Biosciences, Bedford, Mass.) and treated with doxorubicin in the presence or absence of veraparnil (10 μM). After different periods of time (0, 2, 3 h) cells were washed with PBS and fixed in 3.7% paraformaldehyde to be examined by confocal microscopy. Since both, EGFP (present in MCF7/siMCJ cells) and doxorubicin are excited by 488 nm, the conventional multi track type of analysis could not be used. Instead, the Lambda Mode analysis in the Zeiss confocal microscope (Zeiss LSM 510 META Confocal Laser Scanning Imaging System, Carl Ziess Microimaging Inc, Thronwood, N.Y.) was used that allows a precise analysis of the emission spectrum for each fluorochrome (Chen and Simon, J Cell Biol 148, 863-870, 2000). The cells were excited at 488 nm and emission peaks were readily separated by this methodology with EGFP emission at 500 nm and doxorubicin at 600 nm (FIG. 10).

Immunofluorescence Staining by Confocal Microscopy.

MCF7, MCF7/ADR, MCF7/siMCJ-1B, MCF7/siMCJ-3B and 293T cells plated on BD BioCoat poly-D-lysine coverslips. Cells were washed with PBS, fixed in 3.7% paraformaldehyde and permeabilized in a blocking solution (DMEM-F12 with 5% FBS, 0.01% lysine) containing 0.1% TRITON®X-100 for 2 h at room temperature. Cells were then incubated with primary Ab in blocking solution for 1 h at room temperature followed by incubation with the Alexa-568 anti-rabbit or Alexa-568 anti-mouse secondary Abs (Molecular Probes, Eugene, Oreg.) for 30 min. For nuclear staining, either TOPRO™-3 or YOYO® (Molecular Probes, Eugene, Oreg.) was used and MITOTRACKER®-647 (Molecular Probes, Eugene, Oreg.) was used to stain mitochondria. The primary antibodies used included the mouse anti-HA Mab (Cell Signaling Technology, Inc.) Rabbit anti-MCJ polyclonal Ab was generated by using recombinant mouse MCJ (aa 62-150) (Proteintech Group Inc, Chicago, Ill.). The rabbit antiserum was further purified over an antigen column to obtain the MCJ antibody. The semipermiabilization method of freeze thaw was modified from previously described (Mardones and Gonzalez, Journal of Immunological Methods 275, 169-177, 2003) and the staining was performed as mentioned above. Immuno-stained cells were examined by confocal microscopy using the Zeiss LSM 510 META Confocal Laser Scanning Imaging System (Carl Ziess Microimaging Inc, Thronwood, N.Y.)

mRNA Isolation and RT-PCR.

Total RNA was isolated using ULTRASPEC® RNA isolation systems, as recommended by the manufacturer (Biotecx Laboratories, Inc, Houston, Tex.). The first strand cDNA was obtained by reverse transcription as described previously (Conze et al., Cancer Res 61, 8851-8858, 2001). cDNA was used to detect human ABC34, HPRT, MCJ, ABCG2 and ABCC1 expression by conventional PCR or real-time RT-PCR. Previously described primers were used for the conventional RT-PCR amplification of ABCB1 (Noonan et al., Proc Natl Acad Sci USA 87, 7160-7164, 1990), HPRT (Conze et al., Cancer Res 61, 8851-8858, 2001), ABCC1 (Harbottle et al., Int J Cancer 92, 777-783, 2001), ABCG2 (Doyle and Ross, Oncogene 22, 7340-7358, 2003) and MCJ (Shridhar et al., Cancer Res 61, 4258-4265, 2001). For the real-time RT-PCR analysis, by TAQMAN® system (Applied Biosystems), an Assay on Demand Kit for human HPRT and ABCB1 (Sigma, Genosys) was used. For the detection of MCJ by real time RT-PCR, we used the following probe and primer set were used (Sigma, Genosys) (probe 5'-CCTTGCCAGCA-GATGGGCTTACACCTAAA-3; (SEQ ID NO:22) sense primer 5'-CAGAAAATGA GTAGGCGAGAAGC-3' (SEQ ID NO:23) and anti-sense primer 5'-TGACTCTCCTAT-GAGCTGTTCTAATC-3' (SEQ ID NO:24). HPRT was used as an endogenous control to normalize the mRNA values in each sample. The relative values were determined by the comparative CT analysis method.

Western Blot Analysis.

Whole cell extracts were prepared in lysis buffer as previously described (Pedraza-Alva et al., J Biol Chem 276, 729-737, 2001). 40-100 μg of proteins were separated by electrophoresis and transferred on to a nitrocellulose membrane (Conze et al., Cancer Res 61, 8851-8858, 2001). Primary antibodies for Western blotting include anti-ABCB1 (JSB-1 clone) from (ALEXIS corporation Switzerland), rabbit polyclonal anti-MCJ, anti-HA, anti-c-Jun, from (Cell Signaling Technology, Inc) anti-actin and the secondary antibodies goat anti-mouse HRP, goat anti-rabbit HRP and donkey anti-goat HRP Ab from (Santa Cruz Biotechnology). LUMIGLO® chemiluminescent substrate system (KPL, Maryland) was used to visualize the proteins. Levels of actin were determined as loading control.

Immuno-electron Microscopy. 293T cells were transfected with HA-MCJ containing plasmid. After 24 h, transfected cells were fixed by immersion in 3% paraformaldehyde containing 0.1% glutaraldehyde, washed and resuspended in 0.05 M Ammonium chloride. Cells were embedded in agarose and refixed in paraformaldehyde-glutaraldehyde, washed and dehydrated at lower temperature in increasing concentrations of ethanol, followed by infiltration and embedded in the hydrophilic resin LOWICRYL® K4M at −35° C. (Jaskiewicz et al., Glycoconj J 13, 213-223, 1996). Immunostaining was performed with anti-HA MAb (Cell Signaling) overnight incubation at 4° C. followed by a secondary anti-rabbit antibody and protein A-gold particles (10 nm). Contrasting was done using 3% aqueous uranyl acetate and lead citrate. Sections were examined using a JEOL 1210 Transmission Electron Microscope (JEOL-USA, Inc., Peabody, Mass.).

Phylogenetic Analysis.

BLASTp and PSI-BLAST (Altschul et al., Nucleic Acids Res 25, 3389-340, 1997) were used to search for homologous protein sequences in the GENBANK® (ncbi.nlm.nih.gov) nr protein database. A search with the human MCJ ortholog protein (GI 66472920) found 99 proteins (e-value of 0.001). A total of 47 sequences were used in the analysis, all of which were eukaryotic. The protein sequences were aligned using the T-Coffee program to (Notredame et al., In J Mol Biol, pp. 205-217, 2000) with standard parameters. Five evolutionary clades (i.e., groups of sequences with a common ancestor) were identified: plants, yeast TIM14, Fly/worm TIM14-like, vertebrate MCJ and vertebrate TIM14-like. Confidence in each clade was determined by three parameters: 1) bootstrap support under maximum parsimony, 2) bootstrap support using the neighbor joining algorithm, and 3) the posterior probability obtained from MCMC simulation using Mr. Bayes program. The plant clade was set as outgroup. The confidence for yeast TIM14 group of proteins in fungi as a clade was 30/66/NA according to the above parameters and confidence for the ecdysozoan (flies and worms), MCJ and TIM-like sequences as a clade was 86/95/1.00. The confidence for a gene duplication leading to two vertebrate clades, the MCJ and the TIM14-like clades (86/95/1.00). Low confidence (NA/54/NA) was obtained for a gene duplication event had occurred after the divergence of vertebrates from the fly/worm (ecdysozoa) lineage. Stronger support was found for MCJ being the result of gene duplication prior to the divergence of ecdysozoa from vertebrates (50/NA/0.99). Phylogenetic analysis was made using Mr Bayes 3.1 (Huelsenbeck and Ronquist, Bioinformatics 17, 754-755, 2001) for Bayesian methods, and PROTPARS and PROTDIST/NEIGHBOR from the PHYLIP 3.6 package (Felsenstein, Methods Enzymol 266, 418-427, 1996) for maximum parsimony and Neighbor Joining methods respectively.

Nuclear Extracts and Electromobility Shift Assay (EMSA).

Mini nuclear extracts were made from cells as described previously (Schreiber et al., *Nucleic Acids Res* 17, 6419, 1989). Binding reactions were done using 2 µg of nuclear protein in presence of specific $^{32}$P-end-labeled double stranded oligonucleotide as described (Schreiber et al., *Nucleic Acids Res* 17, 6419, 1989). The oligos used in this study are as follows: AP-1 (Angel et al., *Cell* 49, 729-739, 1987; Lee et al., *Cell* 49, 741-752, 1987), C/EBP (Landschulz et al., *Science* 243, 1681-1688, 1989), NF-κB (Kawakami et al., *Proc Natl Acad Sci USA* 85, 4700-4704, 1988). Gel shift assay was performed using 1 µl of the anti-c-Jun, c-Fos, JunB and Jun family Abs (Santa Cruz).

Results and Discussion

MCJ is a Unique Transmembrane DnaJ Protein, Highly Conserved in Vertebrates.

Although some studies have examined the regulation of the MCJ gene by methylation, the biology and function of the MCJ protein remain unknown. A PSI-BLAST search (Altschul et al., *J Mol Biol* 215, 403-410, 1990) was performed using the human MCJ protein sequence to examine its potential evolutionary association with other proteins of known function. The search revealed that MCJ is a member of a set of eukaryotic proteins that contain a conserved transmembrane domain (66%-100%) and the C-terminal DnaJ domain (FIG. 1A). This set includes the previously described yeast TIM14, a component of a mitochondrial inner membrane translocase (Mokranjac et al., *Embo J* 22, 4945-4956, 2003) (FIG. 1A). It also includes a non-characterized human DnaJ protein that has been denominated as "translocase of mitochondria inner membrane" because of its high similarity (67%, p-value: $4\times10^{-15}$) with the yeast TIM14. This TIM14 human ortholog that will be referred as a TIM14-like protein is similar to human MCJ (74%, p-value: $6\times10^{-32}$), but lacks the corresponding N-terminus (FIG. 1A). The sequence similarity searches indicate no other human proteins within this eukaryotic phylogeny.

Five evolutionary clades (i.e. groups of sequences with a common ancestor) (FIG. 1B) were identified: plants, yeast TIM14, Fly/worm TIM14-like, vertebrate TIM14-like and vertebrate MCJ. The plant clade was set as outgroup, meaning that the other four clades share with each other a common ancestor that is not shared with plants (FIG. 1B). The ecdysozoan (flies and worms), MCJ and TIM14-like sequences form a clade. A gene duplication leading to two vertebrate clades, the MCJ and the TIM14-like clades (FIG. 1B) was found with high confidence. Although gene duplication could have occurred after the divergence of vertebrates from the fly/worm (ecdysozoa) lineage (FIG. 1B, upper panel) this was not strongly supported by the results (described in methods). Stronger support was found for MCJ being the result of gene duplication prior to the divergence of ecdysozoa from vertebrates (FIG. 1B lower panel). This would imply that MCJ must then have been lost in the fly/worm lineage(s).

Unlike the transmembrane and C-terminal DnaJ regions that are highly conserved within the five clades, the juxtamembrane C-terminal region is distinct among clades, although it is conserved within each clade (FIG. 1A). Thus, vertebrate MCJ orthologs have a unique juxtamembrane C-terminal region that is not conserved in other clades. In addition, the N-terminus region (35 aa) present in the MCJ clade is absent in the TIM 14-like vertebrate and ecdysone clades and is highly variable in the yeast TIM14 clade (FIG. 1A). However within the MCJ clade, 7 sites of this N-terminus are perfectly conserved and above 90% of the sites exhibit some degree of conservation. The presence of the highly conserved N-terminal region specifically in the MCJ clade, but not in the TIM14-like vertebrate clade suggests distinct functions of these two proteins in vertebrates.

MCJ is a Type II Transmembrane Protein Localized in the Golgi Apparatus.

Figure 2:
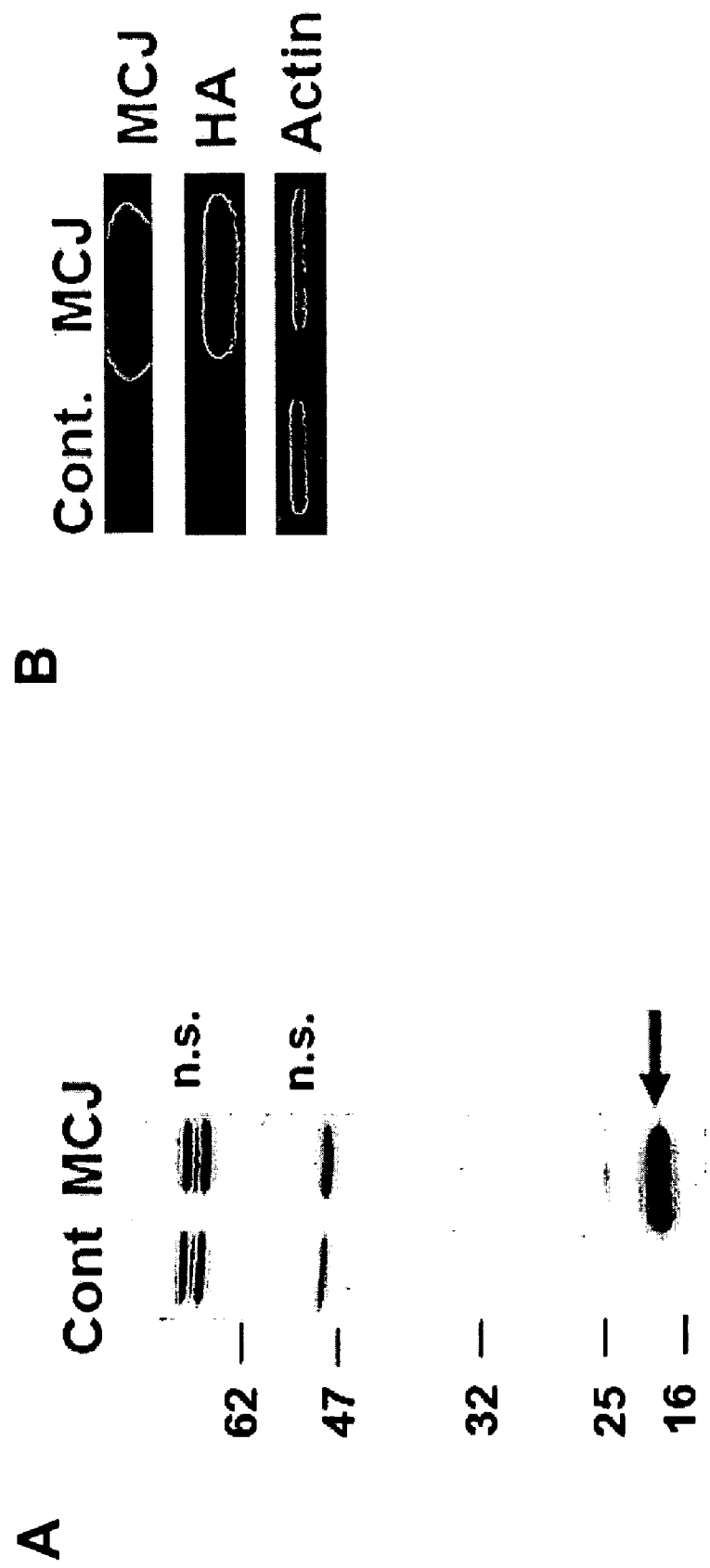
FIG. 2 provides images of blots demonstrating localization of MCJ in the Golgi apparatus. For the Western blots, 293T cells were transfected with a MCJ expressing plasmid (MCJ) or an empty plasmid (Cont). Whole cell extracts were examined for MCJ expression by Western blot using an anti-MCJ polyclonal Ab, an anti-HA Ab and an anti-actin Ab as loading control.

The above MCJ phylogenetic analysis revealed the evolutionary ancestor of MCJ as yeast TIM14 which is localized in the inner mitochondrial membrane (Mokranjac et al., *Embo J* 22, 4945-4956, 2003). No previous studies have addressed the subcellular localization of the MCJ protein. An HA-tagged-MCJ expressing construct was generated that also contains an IRES-EGFP gene and transfected it into 293T cells. MCJ expression was first tested in transfected cells by Western blot analysis. In correlation with its predicted size, a protein of approximately 16-18 kDa was detected only in MCJ-transfected 293T cells, but not in cells transfected with an empty plasmid (FIG. 2A).

MCJ subcellular localization was examined by confocal microscopy analysis in transfected cells. 293T cells were transfected with an MCJ expressing plasmid. Transfected cells were fixed, permeabilized, and stained. MCJ intracellular distribution was examined by confocal microscope. MCJ, EGFP, and TOPRO®-3 nuclear staining was performed. MCJ was clearly a cytoplasmic protein with a distinct punctate distribution in well-defined areas of the cytosol that resembled the distribution of intracellular organelles. No MCJ staining was observed in the untransfected cells. To investigate whether MCJ was localized in the mitochondria, MCJ-transfected cells were co-stained with MITOTRACKER®, a specific marker for mitochondria. However, MCJ did not co-localize with the MITOTRACKER®. To test if MCJ was localized in the endoplasmic reticulum, MCJ expressing plasmid was co-transfected with the pDsRed2-ER plasmid that expresses a red fluorescence protein targeted to the ER by the ER retention (KDEL) sequence. No clear co-localization of MCJ with the pDsRed2-ER was observed by confocal microscopy. To precisely determine the organelle/s where MCJ was localized, immuno-electron microscopy (EM) was performed. MCJ transfected 293T cells were fixed, embedded, sectioned and stained with antibody coated gold particles (pAg10). A clear punctate distribution of MCJ was visualized specifically in the Golgi apparatus. No MCJ localization was detected in the mitochondria, endoplasmic reticulum, or nuclear membrane. Thus, MCJ is an intracellular transmembrane protein localized primarily in the Golgi apparatus.

The superfamily HMM protein topology prediction program predicted that MCJ was a type II transmembrane protein (i.e. intracellular N-terminus and extracellular C-terminus). Because the EM studies showed that MCJ was present in the Golgi, this prediction would suggest that the MCJ C-terminus was in the Golgi lumen whereas the N-terminus was cytoplasmic. To confirm this prediction and further characterize the orientation of MCJ protein, the permeabilization/semipermeabilization method, previously described (Mardones and Gonzalez, Journal of Immunological Methods 275, 169-177, 2003) was used. This approach is based on comparative epitope accessibility by the antibody (Ab) for the detection of intracellular transmembrane protein topology. The classical method of immunostaining involves the permeation of fixed cells with a detergent (e.g. TRITON™ X 100) that allows the antibodies to detect all intracellular proteins independently of their localization. However, the semi-permeabilization method uses a rapid freeze-thawing technique that selectively permeates the plasma membrane, but the intracellular membranes remain impermeable. Because the HA-tag is present at the N-terminus of MCJ the anti-HA Ab was used for detection of the MCJ N-terminal region. For the detection of the C-terminus, a rabbit polyclonal antibody against the C-terminus of MCJ was generated. The specificity of this anti-MCJ Ab was examined by Western blot analysis using extracts from HA-MCJ transfected and non-transfected 293T cells. The anti-MCJ antibody was able to detect MCJ only in the MCJ transfected 293T cells (FIG. 2B). Specificity of the detected band of MCJ was further demonstrated by reprobing the blot with anti-HA Ab (FIG. 2B).

Therefore both anti-HA and anti-MCJ Abs were used to detect MCJ by confocal microscopy analysis. 293T cells were transfected with a HA-MCJ expressing plasmid, fixed, permeabilized, stained with either anti-HA or anti-MCJ Abs and analyzed by confocal microscopy. Both anti-HA and anti-MCJ Abs detected MCJ with similar pattern of expression in the transfected cells. In parallel, HA-MCJ transfected cells were rapidly frozen-thawed for semi-permeabilization fixed, stained with anti-HA and anti-MCJ Abs and analyzed by confocal microscopy. MCJ was detected with the anti-HA Ab, but not with the anti-MCJ Ab indicating that MCJ C-terminus was not accessible to the Ab. These results confirm that the N-terminus of MCJ is cytosolic whereas the C-terminus resides within the Golgi lumen. Thus, MCJ is a type II co-chaperone that resides within the Golgi.

MCJ is Expressed in Drug Sensitive, but not in Drug Resistant Breast Cancer Cells.

Figure 3:
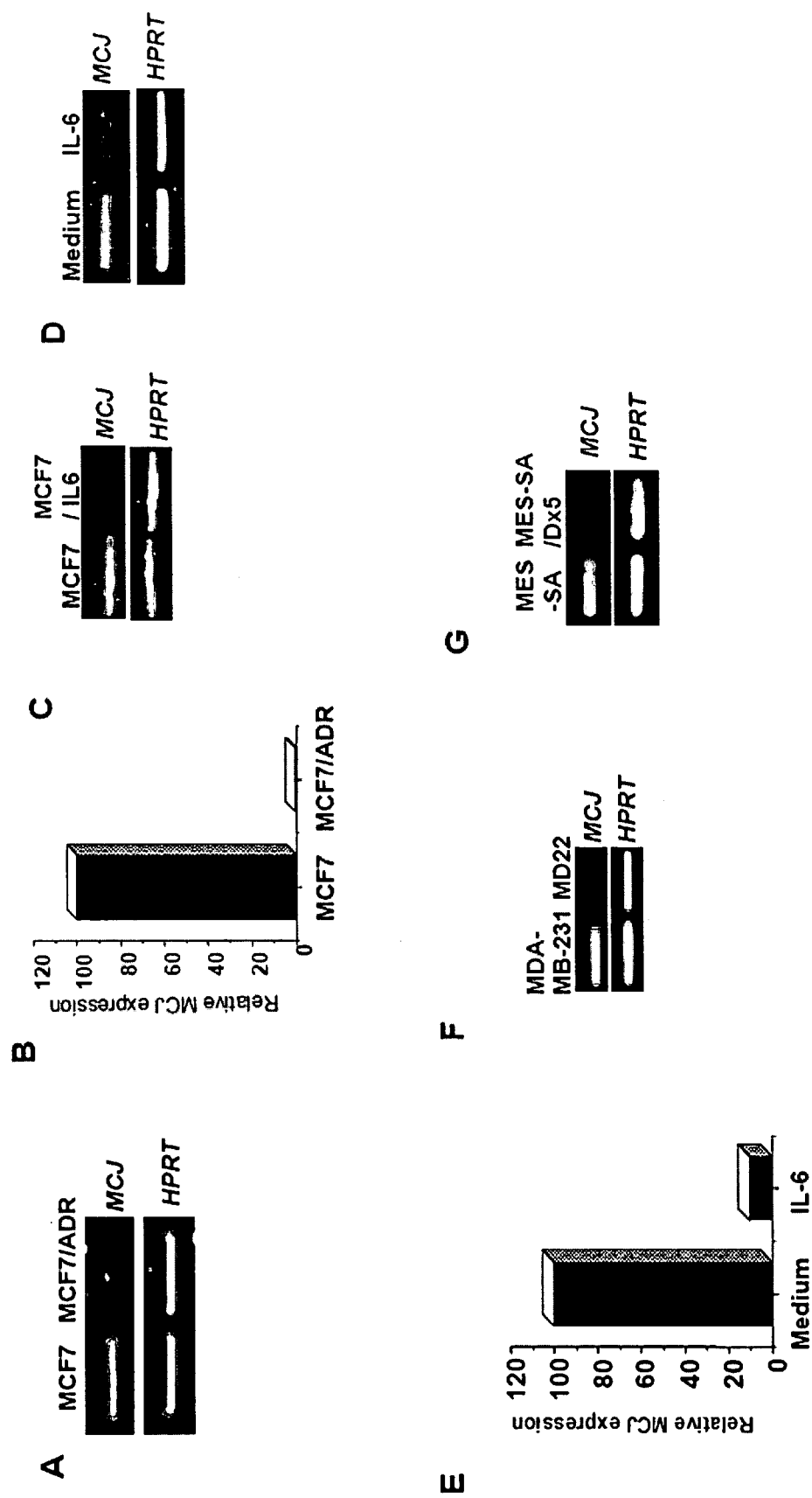
FIG. 3 shows images of gels and histograms indicating the loss of MCJ expression in multidrug resistant breast cancer cells.

Loss of MCJ expression has been associated with increased resistance to chemotherapeutic drugs in ovarian cancer cells ((Shridhar et al., *Cancer Res* 61, 4258-4265, 2001); (Strathdee et al., *Carcinogenesis* 25, 693-701, 2004); (Strathdee et al., *Gynecologic Oncology* 97, 898-903, 2005)). Multidrug resistance is a common phenomenon observed in other cancer types such as breast cancer. To investigate whether the loss of MCJ expression in drug resistant cells was extended to cancer types other than ovarian, MCJ expression was examined in breast cancer cells. MCJ expression in drug sensitive MCF7 breast cancer cells was compared with its expression in MCF7/ADR cells that are derived from MCF7 cells, but are resistant to several drugs including doxorubicin (adriamycin), paclitaxel and vincristine (Fairchild et al., *Cancer Res* 47, 5141-5148, 1987). Total RNA was isolated from MCF7 and MCF7/ADR cells and MCJ expression was examined by conventional reverse transcriptase (RT)-PCR using HPRT as an internal control. MCJ was highly expressed in MCF7 cells, but was undetectable in MCF7/ADR cells (FIG. 3A). Similar results were obtained by quantitative real-time RT-PCR of MCJ (FIG. 3B).

To confirm the loss of MCJ expression in multidrug resistant cells, other MCF7 derived cells with a multidrug resistant phenotype were used. It has previously been shown that multidrug resistant, but not drug sensitive breast cancer cells produce IL-6 and stable expression of IL-6 in MCF7 cells (MCF7/IL-6 cells) confers multidrug resistance (Conze et al., *Cancer Res* 61, 8851-8858, 2001). Therefore total RNA was isolated from MCF7 and MCF7/IL6 cells and examined MCJ expression by RT-PCR. MCJ was expressed in MCF7 cells, but not in the multidrug resistant MCF7/IL6 cells (FIG. 3C). It has also been shown that transient treatment of MCF7 cells with exogenous IL-6 increased drug resistance of these cells (Conze et al., *Cancer Res* 61, 8851-8858, 2001). Experiments were run to test whether this increased resistance was associated with decreased MCJ expression. MCF7 cells that were treated with exogenous IL-6 for one week contained reduced levels of MCJ mRNA compared with untreated MCF7 cells (FIGS. 3D and 3E).

To rule out the possibility that the correlation of reduced MCJ expression and chemoresistance was restricted to this breast cancer cell line another breast cancer cell line, MDA-MB-321, and its doxorubicin-resistant derived MD22 cells (Klement et al., *Clin Cancer Res* 8, 221-232, 2002) were examined. Unlike the multidrug resistant MCF7/ADR cells, MD22 cells are resistant specifically to doxorubicin. RNA was isolated and used to performed RT-PCR for MCJ and HPRT expression. While MDA-MB-321 cells expressed high levels of MCJ, very low levels were detected in MD-22 cells (FIG. 3F). To examine whether MCJ expression was also blocked in other multidrug resistant cells, the drug sensitive MES-SA and its multi-drug resistant derivative MES-SA/Dx5 uterine cancer cell lines (Harker and Sikic, *Cancer Res* 45, 4091-4096, 1985) were examined by RT-PCR. Similarly to MCF7 cells, MCJ was expressed in the MES-SA cells, but its expression was undetectable in MES-SA/Dx5 cells (FIG. 3G). Thus, loss of MCJ expression in drug resistant cells could be a common phenomenon in a number of solid tumors suggesting that MCJ could be a multidrug resistance marker independent of the cancer type.

MCJ is Required for Breast Cancer Cells to Maintain the Tesponse to Chemotherapeutic Drugs.

Figure 4:
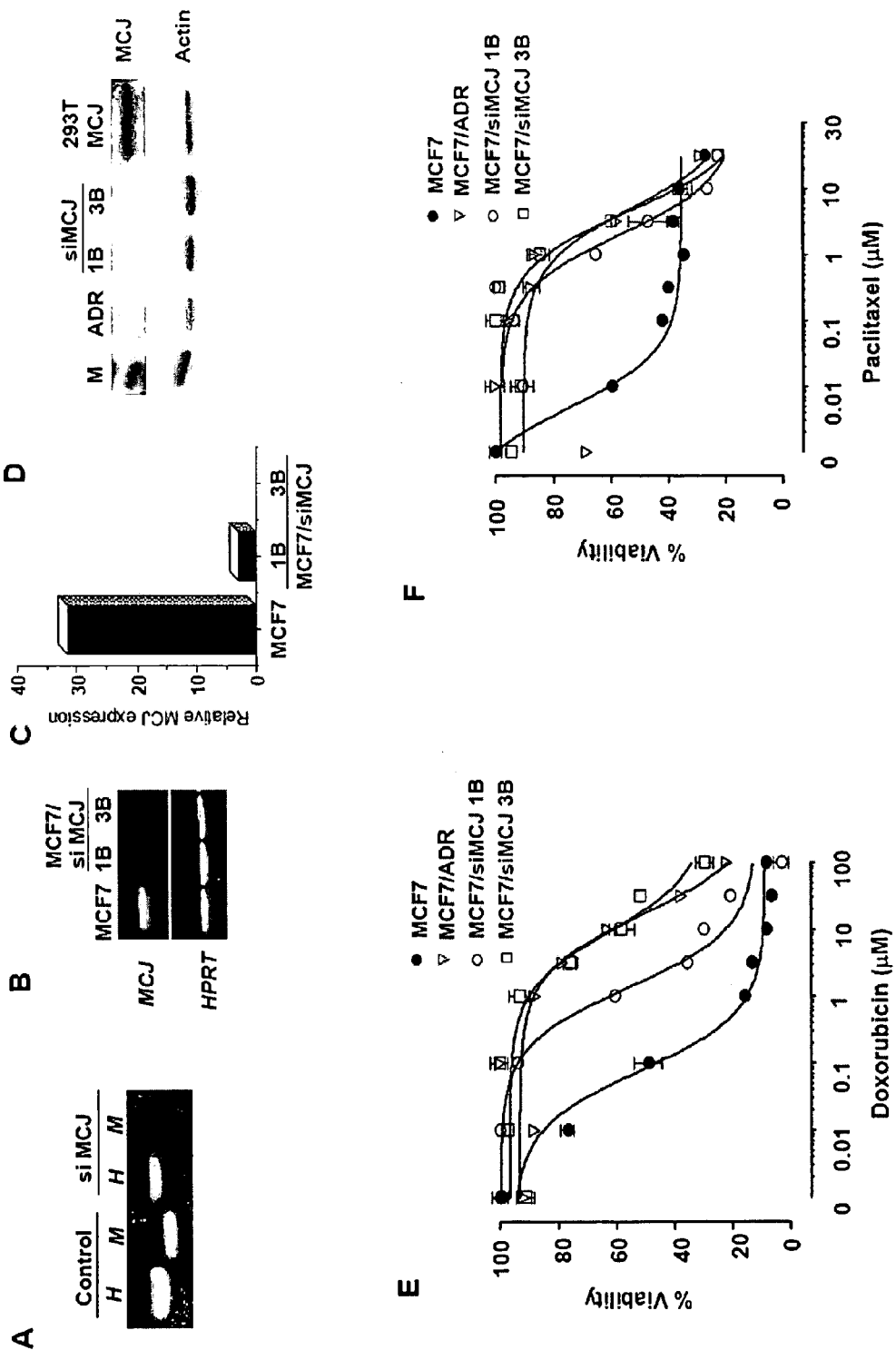
FIG. 4 shows photographs of gels and graphs indicating that MCJ is required for breast cancer cells to maintain chemotherapy response.

To address whether the absence of this Golgi-associated protein by itself could induce multidrug resistance in breast cancer cells, the effect of inhibition of MCJ expression by RNA interference (RNAi) was examined. A siRNA MCJ target sequence (siMCJ) was cloned downstream of the H1 RNA polymerase III promoter in pSuperEGFP, a modified version of the pSuper plasmid (Brummelkarnp et al., *Science* 296, 550-553, 2002) that includes the EGFP gene under control of the CMV-promoter. MCF7 cells were transiently transfected with pSuperEGFP-siMCJ or empty plasmid. Cells transfected with siMCJ have lower levels of MCJ mRNA than cells transfected with the empty plasmid as determined by RT-PCR (FIG. 4A). Stable transfection was then performed with the pSuperEGFP-siMCJ construct in MCF7 cells (MCF7/siMCJ). Two MCF7/siMCJ clones (MCF7/siMCJ-1B and -3B) were selected for further expansion and characterization. Total RNA was isolated from MCF7, MCF7/siMCJ-1B and MCF7/siMCJ-3B cells and examined for MCJ gene expression. No MCJ mRNA was detected in MCF7/siMCJ-3B and MCF7/siMCJ-1B cells by conventional RT-PCR (FIG. 4B) and very low levels were detected only in MCF7/siMCJ-1B cells by quantitative real-time RT-PCR (FIG. 4C).

To confirm that expression of siMCJ in MCF7/siMCJ cells abrogates not only MCJ mRNA expression, but also protein expression, endogenous MCJ protein levels were examined by Western blot using the anti-MCJ Ab. MCJ was clearly present in MCF7 but it was almost undetectable in MCF7/siMCJ-1B and MCF7/siMCJ-3B cells, as well as in MCF7/ADR cells (FIG. 4D). As positive control extracts from MCJ transfected 293T cells (FIG. 4D) were used. These data indicate that, MCJ mRNA and protein expression were abrogated in MCF7/siMCJ cells.

The MCF7/siMCJ-1B and -3B cells have a rate of proliferation similar to that of MCF7 cells and no difference in viability of these cells in culture was observed. Experiments were performed to examine whether inhibition of MCJ expression could increase resistance to doxorubicin (anthracyclin), a commonly used chemotherapeutic drug for breast cancer treatment. MCF7, MCF7/siMCJ-1B and MCF7/siMCJ-3B cells were cultured in the absence or presence of different concentrations of doxorubicin and the percent viability was measured by the MTT assay. In correlation with previous studies (Alley et al., *Cancer Res* 48, 589-601, 1988), MCF7 cells were highly sensitive to doxorubicin while MCF7/ADR cells were highly resistant (FIG. 4E). Interestingly, MCF7/siMCJ-1B and MCF7/siMCJ-3B cells were significantly more resistant to doxorubicin than MCF7 cells (FIG. 4E). The response to paclitaxel (taxane), another commonly used chemotherapeutic drug for breast cancer was also tested. MCF7 cells were highly sensitive to paclitaxel (FIG. 4F). In contrast, MCF7/siMCJ-1B and MCF7/siMCJ-3B cells were highly resistant, similar to MCF7/ADR cells (FIG. 4F). Together, these results demonstrate that MCJ is required for breast cancer cells to respond to different drugs such as doxorubicin and paclitaxel and that inhibition of MCJ expression causes multidrug resistance.

MCJ is Required for Intracellular Accumulation of Chemotherapeutic Drugs.

Impaired intracellular accumulation of chemotherapeutic drugs due to transport-mediated efflux is the best characterized mechanism involved in multidrug resistance (reviewed by (Longley and Johnston, *J Pathol* 205, 275-292, 2005)). The effect of MCJ protein down-regulation on the intracellular accumulation of doxorubicin was examined by confocal microscopy. MCF7, MCF7/siMCJ-1B and MCF7/siMCJ-3B were treated with medium alone or with doxorubicin for 1, 2 or 3 h. Cells were then washed, fixed and doxorubicin fluorescence was visualized by confocal microscopy. No doxorubicin fluorescence was detected in MCF7 cells treated with medium alone or with doxorubicin for only 1 h. After 2 h of treatment, some doxorubicin fluorescence was detected in the MCF7 cells, but maximum level of intracellular accumulation was reached after 3 h. Both MCF7/siMCJ-1B and -3B cells express EGFP, but no doxorubicin fluorescence was observed in these cells after 3 h of treatment. Similarly, no doxorubicin fluorescence was detected at shorter (1 and 2 h) and longer (4 h) periods of treatment in MCF7/siMCJ cells.

To demonstrate that this phenotype was due to inhibition of MCJ expression rather than a result of the selection of the siMCJ cell clones, MCF7 cells were transiently transfected with either an empty pSuperEGFP plasmid or pSuperEGFP-siMCJ plasmid. 36 h after transfection, cells were treated with doxorubicin for 3 h and examined by confocal microscopy analysis. Transfected cells were identified by the presence of EGFP. Both EGFP positive and EGFP negative cells in the control plasmid-transfected MCF7 cells showed doxorubicin accumulation. In contrast, doxorubicin fluorescence could only be detected in EGFP negative, but not EGFP positive siMCJ-transfected MCF7 cells. Thus, transient inhibition of MCJ expression interferes with the intracellular accumulation of the drug.

Figure 5:
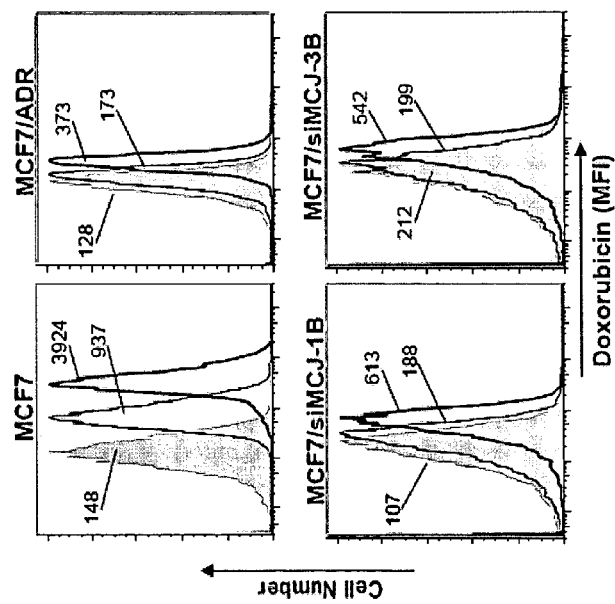
FIG. 5 shows graphs indicating that MCJ is required for intracellular accumulation of doxorubicin. The graphs show results when MCF7, MCF7/ADR, MCF7/siMCJ-1B and MCF7/siMCJ-3B cells were treated with medium alone (gray-filled profiles) or with doxorubicin at 0.3 µM (thin line profiles) or 3 µM (thick line profiles) for 3 h. Doxorubicin intracellular accumulation was examined by flow cytometry. Numbers represent the mean fluorescence intensity (MFI) of doxorubicin.

To confirm the confocal microscopy results, intracellular accumulation of doxorubicin was examined by flow cytometry. MCF7, MCF7/ADR, MCF7/siMCJ-1B and MCF7/siMCJ-3B cells were treated with doxorubicin (0.3 and 3 µM) for 3 h, washed extensively and examined by flow cytometry. High levels of doxorubicin were present in MCF7 cells even at the lower dose (FIG. 5). In contrast, no intracellular accumulation of doxorubicin could be detected in MCF7/siMCJ-1B and -3B cells at the lower dose of doxorubicin (0.3 µM) and very low intracellular levels were detected at the higher dose (3 µM) (FIG. 5). In addition, no doxorubicin was observed in MCF7/ADR cells (FIG. 5). Together, these results demonstrate that the presence of MCJ is required to allow intracellular accumulation of the drug.

MCJ Suppresses ABCB1 Gene Expression.

Figure 6:
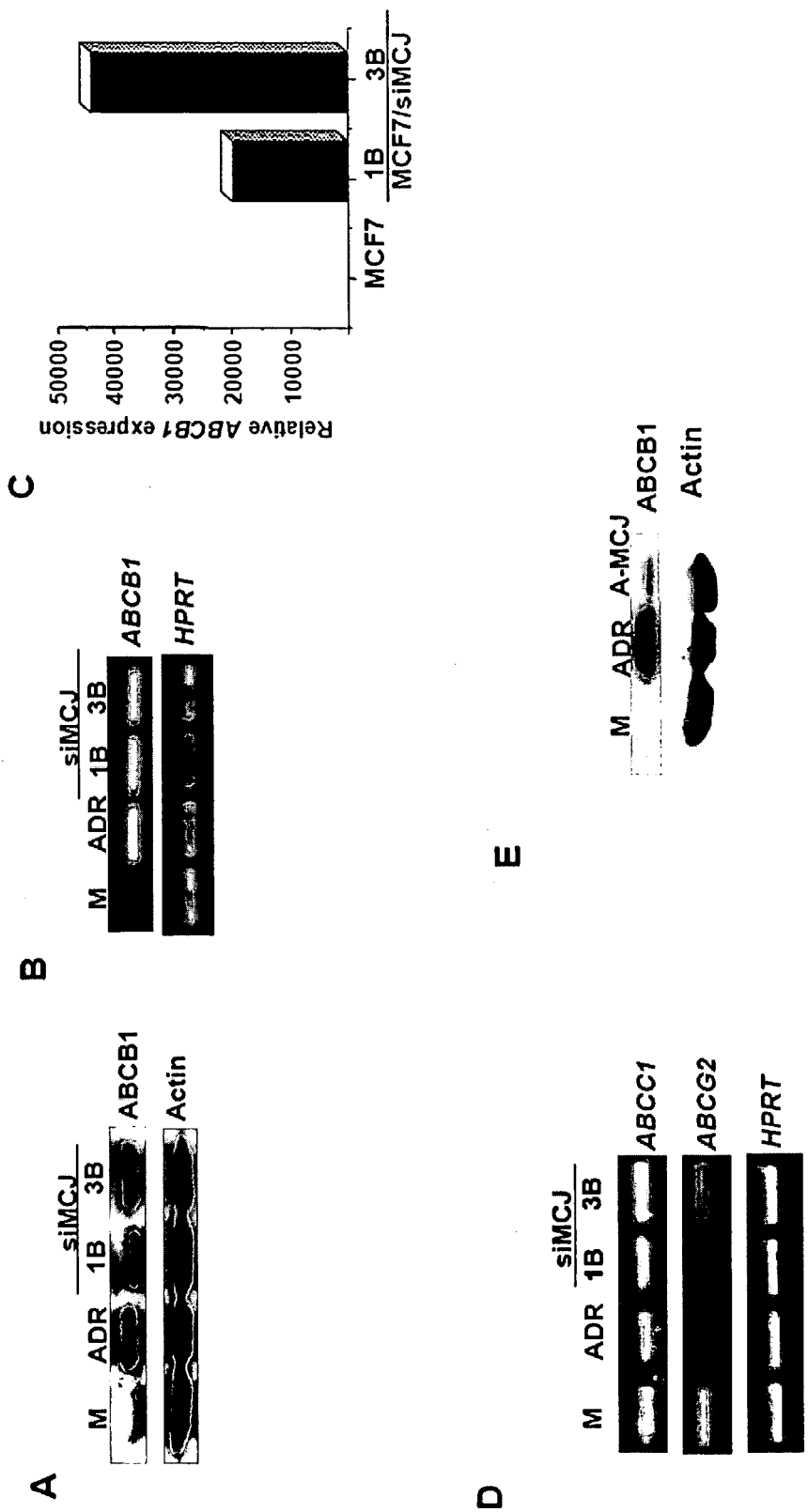
FIG. 6 shows photographs of gels and a histogram indicating that MCJ suppresses ABCB1 gene expression.

The presence of specific ATP-Binding cassette (ABC) transporters that promote drug efflux or drug retention in intracellular compartments of cancer cells is one of the mechanisms to prevent drugs to reach its specific intracellular targets. The ABC transporters constitute a large family with 48 members in humans. Some ABC transporters that use specific drugs as substrates are over-expressed in the cancer cell lines and tumors that are multidrug resistant (reviewed by (Gottesman et al., *Nat Rev Cancer* 2, 48-58, 2002)). The substrates of a large number of these transporters however remain unknown. The best-characterized member of this family is ABCB1 (also named as mdr1 or P-glycoprotein). Since ABCB1 is known to be absent in drug sensitive MCF7 cells (Fairchild et al., *Mol Pharmacol* 37, 801-809, 1990) its expression was examined in MCF7/siMCJ cells by Western blot analysis. In contrast to MCF7 cells, high levels of ABCB1 were present in MCF7/siMCJ-1B and -3B cells (FIG. 6A). As previously described, high levels of ABCB1 were also present in MCF7/ADR cells (FIG. 6A).

To determine whether the effect of MCJ on ABCB1 levels could be due to changes in the expression of the ABCB1 gene, ABCB1 mRNA levels were measured by conventional RT-PCR. ABCB1 was not expressed in MCF7 cells (FIG. 6B), but it was highly expressed in MCF7/siMCJ-1B and -3B cells (FIG. 6B). Similar results were obtained by quantitative real time RT-PCR (FIG. 6C). In addition, inhibition of MCJ expression in MCF7 cells by transient transfection with the pSuperEGFP-siMCJ plasmid also caused an up-regulation of ABCB1 expression. Unlike ABC34, the expression of other multidrug ABC transporters like ABCC1 (MRP)(Diah et al., *Cell* 76, 1025-1037, 2001) and ABCG2 (BCRP) (Doyle and Ross, *Oncogene* 22, 7340-7358, 2003) that are expressed in MCF7 cells, were not altered in MCF7/siMCJ cells (FIG. 6D). Thus, MCJ appears to selectively regulate ABCB1 gene expression.

To further demonstrate the negative role of MCJ on ABCB1 expression, whether or not the expression of MCJ in MCF7/ADR cells downregulates ABCB1 expression was examined. MCF7/ADR cells were transfected with a MCJ-expressing plasmid. Stable MCJ-transfected MCF7/ADR clones (MCF7/ADR-MCJ) were selected. The expression of MCJ did not affect the cell survival or proliferation of these cells. The ABCB1 expression in these cells was examined by Western blot analysis. Although not totally abrogated, the ABCB1 levels in MCF7/ADR-MCJ were substantially reduced compared with MCF7/ADR cells (FIG. 6E). Together these results indicate that MCJ is able to negatively regulate ABCB1 expression.

Multidrug Resistance Induced by the Loss of MCJ Expression is Mediated by ABCB1.

To determine whether the presence of ABCB1 expression in MCF7/siMCJ cells was responsible for the inability of these cells to accumulate doxorubicin, the effect of verapamil, a known pharmacological inhibitor of ABCB1 (Chen et al., *J Biol Chem* 265, 10073-10080, 1990) was examined. MCF7/siMCJ-1B and MCF7/ADR cells were treated with doxorubicin for 3 h in the presence or absence of verapamil. Intracellular drug accumulation was examined by confocal microscopy. No doxorubicin fluorescence was detected in MCF7/siMCJ-1B cells, but clear intracellular accumulation was observed after addition of verapamil. Similar results were observed in MCF7/ADR cells. To confirm these results doxorubicin fluorescence was measured by flow cytometry analysis. Verapamil allowed the intracellular accumulation of doxorubicin in MCF7/siMCJ-1B cells and had no effect in MCF7 cells (FIG. 7A).

In contrast to anthracyclins and taxanes, 5-fluorouracil (5-FU) is not a substrate for ABCB1 and MCF7/ADR cells are therefore equally sensitive to this drug as MCF7 cells (Mechetner et al., Clin Cancer Res 4, 389-398, 1998). To further confirm the involvement of ABCB1 in multidrug resistance of MCF7/siMCJ cells, the response of these cells to 5-FU by MTT assay was examined. The dose-response to 5-FU was comparable in MCF7, MCF7/ADR, MCF7/siMCJ-1B and -3B cells (FIG. 7B). Together, these results indicate that the inability of MCF7/siMCJ cells to accumulate doxorubicin is at least partially mediated by overexpression of ABCB1.

The Absence of MCJ Increases c-Jun Levels and Transcriptional Activity

Figure 8:
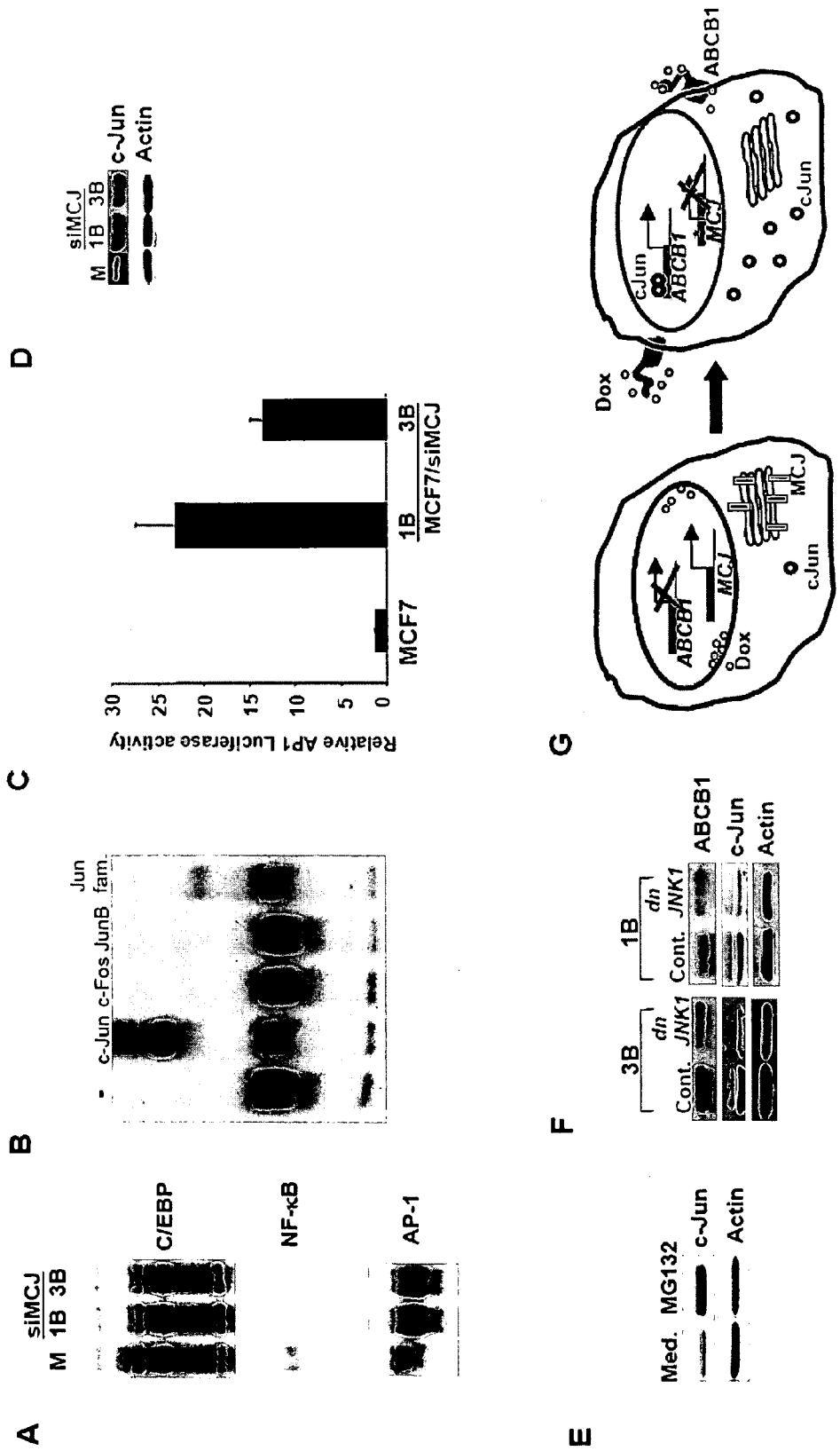
FIG. 8 shows photographic images of gels, a histogram and a cell diagram indicating that MCJ downregulates ABCB1 expression by modulation of AP1 transcription factor.

Several transcription factors have been shown to be involved in the regulation of ABCB1 gene expression including AP-1, C/EBP and NF-κB (reviewed by Scotto, *Oncogene* 22, 7496-7511, 2003). To investigate the mechanism by which MCJ regulates ABCB1 expression, AP-1, C/EBP and NF-κB DNA binding was examined by Electrophoretic Mobility Shift Assay (SMSA) using the nuclear extracts from MCF7 and MCF7/siMCJ cells. No difference in C/EBP DNA binding was observed between MCF7 and MCF7/siMCJ cells (FIG. 8A). Low levels of NF-κB DNA binding could be detected in MCF7 cells, and the levels in MCF7/siMCJ cells were practically undetected (FIG. 8A). In contrast, AP-1 DNA binding was highly increased in MCF7/siMCJ cells compared with MCF7 cells (FIG. 8A).

AP-1 is composed of either heterodimers of Jun and Fos family members or homodimers of Jun family members (Halazonetis et al., *Cell* 55, 917-924, 1988). To identify the composition of the AP-1 complex in the MCF7/siMCJ cells, supershift analysis was performed with Ab specific for AP-1 components using nuclear extracts from these cells. Anti-JunB and anti-Fos Ab did not substantially compete with AP-1 DNA binding and no supershift complex could be detected, indicating that neither of these members was present in the complex (FIG. 8B). In contrast, anti-cJun Ab strongly inhibited the AP-1 binding and a supershift complex was present (FIG. 8B). Similarly, an Ab that does not supershift but competes with the DNA binding of the three Jun family members (c-Jun, JunB and JunD) also inhibited the AP-1 complex present in the siMCJ cells (FIG. 8B). These results indicate that the AP-1 complexes present in MCF7/siMCJ cells consist predominantly of c-Jun dimers.

To examine whether increase c-Jun DNA binding resulted in increased AP-1-mediated transcription, MCF7 and MCF7/siMCJ cells were transfected with an AP-1-luciferase reporter construct. In correlation with the high AP-1 DNA binding activity, increased AP-1 transcriptional activity was detected in MCF7/siMCJ cells (FIG. 8C). Loss of MCJ therefore induced AP-1 mediated transcription.

It was determined whether the increased c-Jun DNA binding in siMCJ cells could be due to an upregulation of c-Jun protein levels. The levels of c-Jun by Western blot analysis were examined using whole cell lysates. Very low levels of c-Jun were detected in MCF7 cells, but high levels were present in MCF7/siMCJ cells (FIG. 8D). It has been previously reported that c-Jun levels can be regulated by ubiquitination and proteasome mediated degradation (Treier et al., Cell 78, 787-798, 1994). Whether the low levels of c-Jun in MCF7 cells were due to increased proteasomal degradation was examined by treating these cells with the proteasome inhibitor MG132 and performing Western blot analysis. Increased levels of c-Jun were observed in the MG132-treated MCF7 cells compared with untreated MCF7 cells (FIG. 8E).

To demonstrate that c-Jun is responsible for the induction of ABCB1 expression in MCF7/siMCJ cells, c-Jun mediated transcription was inhibited. c-Jun transcription activity requires its phosphorylation at $Ser^{63}$ and $Ser^{73}$ by JNK1 (Derijard et al., *Cell* 76, 1025-1037, 1994). MCF7/siMCJ cells were transiently transfected with a dominant negative JNK1 (dnJNK1) mutant expressing plasmid (Derijard et al., *Cell* 76, 1025-1037, 1994). ABCB1 expression in non-transfected and transfected cells was examined by Western blot. The presence of dnJNK1 in MCF7/siMCJ-1B and -3B cells caused a substantial reduction of the ABCB1 levels (FIG. 8F). Thus, induction ABCB1 expression by the loss of MCJ is mediated by c-Jun.

In addition to transcriptional activity, phosphorylation of c-Jun by JNK has also been shown to protect c-Jun from ubiquitination and degradation (Fuchs et al., *Oncogene* 13, 1531-1535, 1996; Musti et al., *Science* 275, 400-402, 1997). Therefore experiments were performed to examine the levels of c-Jun in MCF7/siMCJ cells transfected with the dnJNK1 mutant. In agreement with the reduction of ABCB1 levels, the levels of c-Jun were also substantially decreased in the presence of dnJNK1. Together, these data indicate that the loss of MCJ leads to increased levels of c-Jun and c-Jun-mediated ABCB1 expression.

Discussion

Multidrug resistance is a complex and multifactorial phenomenon. It appears to be the major cause of chemotherapy failure in breast cancer since it is associated with the lack of response to a variety of drugs. The identification of tumor markers that can help to predetermine the response to a given type of chemotherapy is therefore an area of high priority'n breast cancer research. The overexpression of markers (e.g. specific ABC transporters) exclusively in multidrug resistant cancer cells and their absence in their drug-sensitive counterparts is the most frequent scenario (reviewed by (Longley and Johnston, *J Pathol* 205, 275-292, 2005)). In contrast, loss of expression of specific markers and multidrug resistance is less frequent. Loss of MCJ expression by methylation of the MCJ gene has been correlated with multidrug resistance in ovarian cancer cell lines. In addition, it has been recently shown that high levels of methylation of the MCJ gene correlate with poor response of ovarian tumors to therapy and patient's poor survival rates (Strathdee et al., *Gynecologic Oncology* 97, 898-903, 2005). Here it has now been shown that loss of MCJ expression also correlates with multidrug resistance in two independent breast cancer cell lines and in a uterine cancer cell line. Immuno-histochemistry analysis of MCJ in breast tumor arrays indicated that MCJ expression in a number of tumors is lost, but further studies are needed to show the correlation with chemotherapy response. Thus, MCJ may be a widely used marker for chemoresistance among different types of cancer.

MCJ however is not just a marker for chemotherapy response. Here it has been shown that the presence or absence of MCJ clearly modulates the response of breast cancer cells to specific chemotherapeutic drugs. MCJ was already associated with chemotherapeutic response in ovarian cancer cells, but no mechanism has yet been proposed. In this study, it has now been determined that the absence of MCJ prevents intracellular drug accumulation. This is at least partially due to the upregulation of the ABCB1 transporter since verapamil reverses doxorubicin intracellular accumulation in the absence of MCJ and the expression of ABCC1 and ABCG2 is not affected. However, it is possible that MCJ may also regulate the expression of other uncharacterized ABC transporters of unknown function that might be additional targets for verapamil.

It has been shown herein that the expression of the ABCB1 induced by the loss of MCJ is mediated by c-Jun. The intracellular concentration of c-Jun is normally tightly regulated through rapid turnover by ubiquitination and degradation, a process that is regulated in part by phosphorylation of c-Jun. Phosphorylation of c-Jun by JNK has been shown to reduce c-Jun ubiquitination leading to increased c-Jun stabilization (Fuchs et al., *Oncogene* 13, 1531-1535, 1996; Musti et al., *Science* 275, 400-402, 1997; Musti et al., *Biol Chem* 377, 619-624, 1996). In contrast, phosphorylation of c-Jun by COOH-terminal Src kinase (CSK) at Y26 and Y170 appears to promote cJun degradation (Zhu et al., *Cancer Res* 66, 5729-5736, 2006). Here we show that MCF7 cells do not contain significant amounts of c-Jun despite of being tumor cells. However, inhibition of the proteasome function highly increased c-Jun levels indicating that an active ubiquitination and degradation process prevents c-Jun to accumulate in these cells. In the absence of MCJ however, c-Jun is able to accumulate in MCF7 cells. Thus, it is proposed that MCJ promotes ubiquitination and/or degradation of c-Jun although the mechanism is further investigated in future studies.

Figure 9:
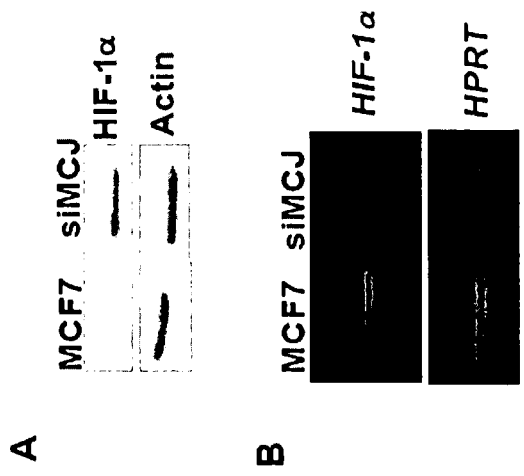
FIG. 9 shows images of blots indicating HIF-1α expression in MCF7 and siMCJ cells.

Recently, it has been shown that ubiquitination of c-Jun is carried out by specific ubiquitin ligases such as Itch (Gao et al., *Science* 306, 271-275, 2004) and SCF$^{Fbw7}$ (Nateri et al., *Science* 303, 1374-1378, 2004). In addition, c-Jun is also regulated by deubiquitination through the deubiquitinase POH1 (Nabhan and Ribeiro, *J Biol Chem* 281, 16099-16107, 2006). Both ubiquitination and deubiquitination have been subcellularly localized to lysosomes and endosomes (Fang and Kerppola, *Proc Natl Acad Sci USA* 101, 14782-14787, 2004; (Nabhan and Ribeiro, *J Biol Chem* 281, 16099-16107, 2006)). Thus, MCJ may promote ubiquitination or inhibit deubiquitination of c-Jun and potentially other proteins. In this regard, it was also found that the levels of hypoxia inducible factor (HIF)1α, a transcription factor primarily regulated by ubiquitination and degradation (Salceda and Caro, *J Biol Chem* 272, 22642-22647, 1997), were higher in the MCF7/siMCJ cells relative to MCF7 cells (FIG. 9). Although HIF1α has also been involved in the transcription of ABCB1 gene in hypoxia (Comerford et al., *Cancer Res* 62, 3387-3394, 2002), inhibition of HIF-1α expression in the MCF7/siMCJ cells did not interfere with ABCB1 gene expression.

In summary, MCJ is a unique type II trans-membrane DnaJ protein present in the Golgi apparatus that acts as a repressor of the ABCB1 by promoting degradation of c-Jun in breast cancer cells. Loss of MCJ expression causes an increased stabilization of c-Jun-mediated transcription leading to the induction of ABCB1 expression. ABCB1 actively effluxes the drug out of the cell and causes multidrug resistance as summarized in the model (FIG. 8G).

Example 2

Generation of Anti-MCJ Monoclonal Antibodies

Previous studies in ovarian cancer patients have examined the correlation of MCJ gene methylation and chemotherapy response (Strathdee, G., et al., *Gynecologic Oncology* 97, 898-903 (2005). However, this assay requires the isolation of genomic DNA from frozen tumor samples, sodium bisulphate treatment of the genomic DNA, PCR amplification, purification of PCR fragments, sequencing of the fragments and assessment of the relative peak intensity of the sequencing reaction. Thus, although highly informative, this type of assay is a relatively complex test to be carried out in a standard clinical laboratory for a large sample population. MCJ expression has now been examined in paraffin embedded breast tumors by immunohistochemistry, a standard clinical assay. However, there are no commercial anti-MCJ antibodies and no studies have published any available antibody or performed studies with MCJ protein. Antibodies against MCJ have now been generated. A rabbit polyclonal antibody was generated against the recombinant full-length MCJ protein (Proteintech Group Inc). This anti-MCJ polyclonal Ab gave immunoreactivity only in 293T cells transfected with a MCJ-expressing construct, but not the non-MCJ expressing cells, and the intracellular distribution was identical to that obtain with an anti-HA antibody that recognizes tagged-MCJ. This polyclonal antibody also recognized MCJ by western blot analysis.

Although polyclonal antibodies may have more affinity and often work better for immunostaining in fixed sections, there are several concerns for their use in clinical diagnosis. Because polyclonal antibodies are normally generated by immunization of rabbits (or alternative host) with the specific protein, there is some variability among batches of sera depending of the immune response of the individual immunized host. Variability in the batch of antibody is a common problem that can substantially affect the results when a large population is examined over time and in different performance sites. Thus, as a routine assay that can be used for an unlimited period of time and with minimal variability it is important to generate monoclonal antibodies (MAbs) produced by clonal hybridomas. Monoclonal antibodies ensure consistency and reproducibility in any type of assay. Monoclonal antibodies against MCJ have now been generated that may be for clinical studies.

An N-terminus (35 aa) polypeptide [MAARGVI-APVGESLRYAEYLC (SEQ ID NO:1)] was used as an immunogen because this region has no homology with any other human proteins (FIG. 1A). This results in reduced binding of the antibody to other non-specific proteins. In addition, this polypeptide has an amino acid composition appropriate to maintain the polypeptide soluble for immunization purpose. The MCJ N-terminus polypeptide was coupled to KLH and used to immunize (e.g., inoculate) mice, and followed by the fusion of spleen cells from immunized mice. 72 pools of hybridomas were isolated. Screening of supernatants from the 72 different mouse hybridoma pools was performed by immunostaining fixed MCJ-transfected 293T cells and confocal microscopy analysis. 293T cells were transfected with MCJ and EGFP expressing constructs. Following the protocol described in Example 1, [see section entitled: MCJ is a type II transmembrane protein localized in the Golgi apparatus], cells were then fixed, permeabilized and individually stained with each of the 72 hybridoma pool supernatants, followed by staining with an Alexa$^{568}$-conjugated anti-mouse secondary antibody. Each of the 72 immunostained slides were then analyzed by confocal microscopy.

Figure 7:
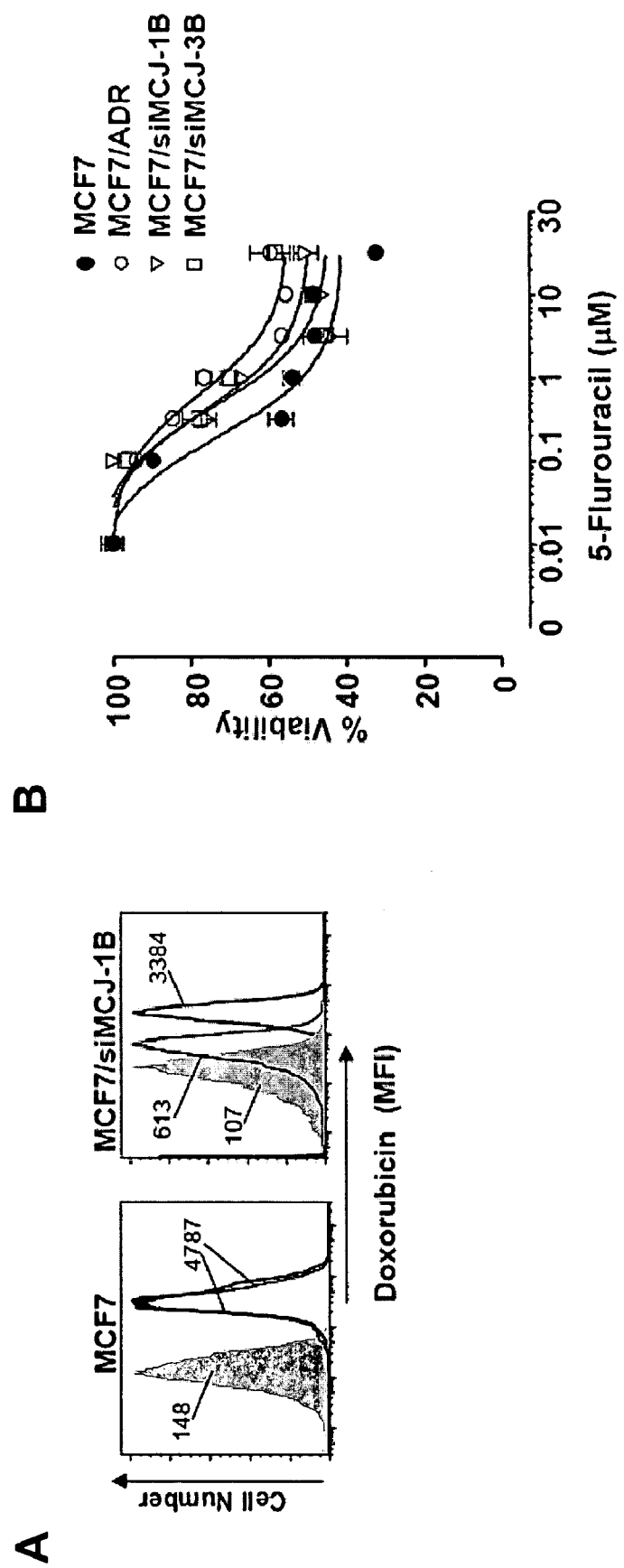
FIG. 7 shows graphs indicating that Multidrug resistance induced by the loss of MCJ expression is mediated by ABCB1.

Antibody pools were selected that reacted only with the MCJ-transfected cells (EGFP positive) and showed the same intracellular punctate distribution previously obtained for MCJ using the anti-HA antibody (FIG. 7). The antibodies that showed immunoreactivity in both MCJ-transfected and non-transfected cells and showed different cellular localization (e.g., nucleus) were discarded. Although a labor intensive screening system, it was intentionally designed to select antibodies that specifically recognize the native MCJ protein (versus denatured protein by Western blot analysis) in fixed samples since these antibodies will then be used for staining in fixed tumor tissues. In addition, this screening system permitted to select only those antibodies that provide the same specific MCJ intracellular distribution that we obtained with anti-tag antibodies.

Three pools (3C, 2A and 3B) that gave very strong specific staining were selected for a second re-cloning to isolate individual clones. 45, 59 and 62 single hybridoma clones (monoclonal) from each pool, respectively, have been recently screened following the same protocol (confocal microscopy). Three individual hybridoma clones (N-MCJ 3C1.3F3, N-MCJ 3C1.5A12, and N-MCJ 2A2.5E4) were selected for further expansion, freezing of cells and purification of the antibody. The monoclonal antibodies of these three hybridomas are referred to herein as: WN.F3, WN.A12, and WN.E4, respectively. Cells were analyzed with these anti-N-terminus MCJ MAbs. 293T cells were transiently transfected with MCJ and EGFP-expressing plasmid. Cells were then fixed, permeabilized, and stained with the WN.A12, WN.F3 and WN.E4 anti-MCJ Mabs individually. The nuclear dye TOPRO (blue) was used to visualize all cells. Immunostaining was examined by confocal microscopy. Each of the three selected anti-MCJ monoclonal antibodies showed staining in MCJ-transfected 293T cells. The nuclear dye TOPRO (blue) was used as marker to visualize all cells (transfected and non-transfected). Anti-MCJ antibodies (red) immuoreact only with MCJ-transfected (EGFP positive, green), but not in non-trasfected cells (EGFP negative cells). MCJ punctate distribution could be seen at higher magnification with the EGFP (green) channel turned off. A similar pattern and intensity of staining was obtained for the three MAbs.

Figure 11:
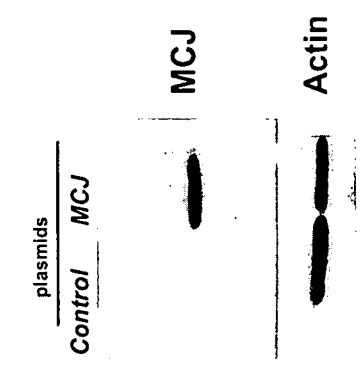
FIG. 11. shows a blot depicting results for 293T cells that were transfected with a MCJ expressing plasmid (MCJ) or a plasmid control (Control). Whole cell extracts were examined for MCJ expression by Western blot analysis using the WeN.A12 anti-MCJ Mab (MCJ). Blot was reprobed for actin as a loading control.

To further confirm the specificity of anti-MCJ Abs, Western blot analysis has been performed using extracts from MCJ-transfected or non-transfected 293T cells and the WN.A12 anti-MCJ MAb. A specific band of the corresponding size was observed only in the MCJ-transfected cells (FIG. 11). The non-specific background of the antibody was minimal.

Analysis of Anti-MCJ mAb in Fixed Breast Cancer Sections.

The data indicated that the three MAbs recognize MCJ in fixed cells and suggests that these antibodies are likely to work also in fixed tissue. Preliminary immunohistochemistry analysis for MCJ has now been performed on 25 independent tumor samples, each of them represented by three needle biopsies, using one of the Mabs. The breast tumor sections were made from paraffin embedded tissue blocks randomly chosen from the Vermont Cancer Center tissue bank.

The protocol followed for MCJ immunostaining was similar to the protocol used for detection of P-gp/ABCB1 and IL-6 in recent work described in Rincon, M., et al., *Breast Cancer Res Treat.* 100(3):301-308 December (2006)). Tissue sections (5 microns) from paraffin embedded blocks were deparaffinized and rehydrated. Sections were then treated with 1.5% hydrogen peroxide/methanol solution to block endogenous peroxidase activity. Antigen retrieval was performed by boiling the sections in 0.1M citrate buffer (pH 6.0), followed by incubation with Protein Block (normal serum). The sections were incubated with the anti-MCJ WN.A12 MAb. For this experiment supernatant of the N-MCJ 3C1.5A12 hybridoma was used (1:2 dilution) because they had not yet completed the final purification of the antibody from the supernatant. Incubation was done overnight (16 h) at 4° C. After a series of washes (PBS/Tween), sections were incubated with a biotinylated anti-mouse polyclonal secondary Ab (30 min at room temp) followed by three washes. A combination of an avidin-biotin system and a 3,3'-diaminobenzidine (DAB) peroxidase substrate system was used. Sections were also stained with the anti-mouse secondary antibody alone to determine the background of negative controls. Slides were counterstained with hematoxylin, dehydrated, coverslipped and examined on an Olympus BX41 light microscope.

MCJ was clearly present in tumor cells (not in stroma cells) in some but not all the samples (46% of the 25 samples were positive for MCJ). Results were consistent among the three sections within each tumor. The staining was clean, without background. No staining was obtained with the secondary antibody alone in the absence of anti-MCJ MAb, in correlation with the previously performed study (Rincon, M., et al., *Breast Cancer Res Treat.* 100(3):301-308 December (2006)). In addition, a higher magnification of the positive samples showed that the immunoreactivity was exclusive in the cytoplasm (no nuclear or cytoplasmic membrane staining) and the staining in the cytoplasm was somewhat punctated (as we observed in cells in vitro) instead of a largely diffused staining. These data indicate that the anti-MCJ MAb can be successfully used in paraffin embedded tissues as predicted based on the screening system used, and that MCJ is present in primary breast cancer cells. The data also that indicate that the use of anti-MCJ MAbs is sensitive enough to clearly detect endogenous levels of MCJ in tissues, that not all tissue samples show immunoreactivity for MCJ and that the staining is well defined (not staining in stroma) to distinguish the specific signal from background.

The purified monoclonal antibodies of Example 2 referred to herein as WN.F3, WN.A12, and WN.E4 and are derived from clones 45, 59, and 62, respectively. The hybridoma cell line identified as N-MCJ 3C1.3F3, which produces the antibody WN.F3 was deposited with the American Type Culture Collection (ATCC) at 10801 University Avenue, Manassas, Va. 20110, U.S.A. on Jan. 11, 2007 and has been assigned ATCC Patent Depository Number: #PTA-8135, by the ATCC. The hybridoma identified as N-MCJ 3C1.5A12, which produces the antibody WN.A12 was deposited in the ATCC in Manassas, Va. on Jan. 11, 2007 and has been assigned ATCC Patent Depository Number: #PTA-8133, by the ATCC. The hybridoma N-MCJ 2A2.5E4, which produces the antibody WN.E4 was deposited with the ATCC in to Manassas, Va. on Jan. 11, 2007 and has been assigned ATCC Patent Depository Number: #PTA-8134, by ATCC.

Although the invention has been described in detail for the purpose of illustration, it is understood that such detail is solely for that purpose and variations can be made by those skilled in the art without departing from the spirit and scope of the invention which is defined by the following claims.

The contents of all references, patents and published patent applications cited throughout this application are incorporated herein by reference in their entirety.

What is claimed is:

1. An isolated monoclonal antibody or antigen-binding fragment thereof that binds specifically to an epitope of the methylation-controlled J (MCJ) polypeptide set forth herein as SEQ ID NO:25, wherein said epitope is contained within the region of the MCJ polypeptide consisting of the amino acid sequence of SEQ ID NO: 1.

2. The isolated monoclonal antibody or antigen-binding fragment thereof of claim 1, wherein the monoclonal antibody competitively inhibits binding of a WN.A12 antibody produced by the hybridoma deposited under ATCC Deposit No. PTA-8133 to the epitope of the MCJ polypeptide.

3. The isolated monoclonal antibody or antigen-binding fragment thereof of claim 1, wherein the monoclonal antibody is a WN.A12 antibody produced by the hybridoma deposited under ATCC Deposit No. PTA-8133.

4. An isolated polyclonal antibody that specifically binds to one or more epitopes of a peptide consisting of SEQ ID NO: 1.

5. The isolated antibody or antigen-binding fragment thereof of claim 1, wherein the antibody specifically binds the epitope of the MCJ polypeptide with a binding affinity of $1 \times 10^{-9}$ M or less.

6. The isolated monoclonal antibody or antigen-binding fragment thereof of claim 1, wherein the monoclonal antibody is a recombinant antibody.

7. A nucleic acid molecule that encodes the isolated antibody of claim 1.

8. A hybridoma that comprises the nucleic acid molecule of claim 7.

9. A hybridoma cell line that produces the isolated antibody of claim 1.

10. The hybridoma cell line of claim 9, wherein the hybridoma is N-MCJ 3C1.5A12 deposited under ATCC Deposit No.: PTA-8133.

11. An expression vector comprising an isolated nucleic acid molecule encoding the isolated antibody or antigen-binding fragment thereof of claim 1.

12. An isolated host cell transformed by or transfected with the expression vector of claim 11.

13. A plasmid which produces the antibody or antigen-binding fragment thereof of claim 1.

14. A composition comprising the antibody or antigen-binding fragment thereof of claim 1.

15. An isolated, immunogenic fragment of a methylation-controlled J (MCJ) polypeptide consisting of SEQ ID NO: 1.

16. A composition comprising the isolated immunogenic fragment of claim 15.

17. A method of determining the amount of a methylation-controlled J (MCJ) polypeptide comprising SEQ ID NO: 25 in a sample, said method comprising:
    contacting a sample with an antibody or antigen-binding fragment thereof that binds specifically to an epitope of the MCJ polypeptide, and
    quantitating the amount of binding of the antibody or antigen-binding fragment thereof in the sample as a determination of the amount of the MCJ polypeptide in the sample, wherein said epitope is contained within the region of the MCJ polypeptide consisting of the amino acid sequence of SEQ ID NO: 1.

18. The isolated antibody or antigen-binding fragment thereof of claim 1, wherein the antibody competitively inhibits binding of a WN.F3 antibody produced by the hybridoma deposited under ATCC Deposit No. PTA-8135 or a WN.E4 antibody produced by the hybridoma deposited under ATCC Deposit No. PTA-8134 hybridoma, to a methylation-controlled J (MCJ) polypeptide set forth herein as SEQ ID NO:25.

19. The isolated antibody or antigen-binding fragment thereof of claim 1, wherein the antibody is a WN.F3 antibody produced by the hybridoma deposited under ATCC Deposit No. PTA-8135 or a WN.E4 antibody produced by the hybridoma deposited under ATCC Deposit No. PTA-8134.

20. The hybridoma cell line of claim 9, wherein the hybridoma is N-MCJ 3C1.3F3 deposited under ATCC Deposit No. PTA-8135 or N-MCJ 2A2.5E4 deposited under ATCC Deposit No. PTA-8134.

* * * * *

SEQUENCE LISTING

```
<160> NUMBER OF SEQ ID NOS: 33

<210> SEQ ID NO 1
<211> LENGTH: 21
<212> TYPE: PRT
<213> ORGANISM: Homo sapiens

<400> SEQUENCE: 1

Met Ala Ala Arg Gly Val Ile Ala Pro Val Gly Glu Ser Leu Arg Tyr
1               5                   10                  15

Ala Glu Tyr Leu Cys
            20

<210> SEQ ID NO 2
<211> LENGTH: 20
<212> TYPE: PRT
<213> ORGANISM: Homo sapiens

<400> SEQUENCE: 2

Met Ala Ala Arg Gly Val Ile Ala Pro Val Gly Glu Ser Leu Arg Tyr
1               5                   10                  15

Ala Glu Tyr Leu
            20

<210> SEQ ID NO 3
<211> LENGTH: 29
<212> TYPE: PRT
<213> ORGANISM: Homo sapiens

<400> SEQUENCE: 3

Met Ala Ala Arg Gly Val Ile Ala Pro Val Gly Glu Ser Leu Arg Tyr
1               5                   10                  15

Ala Glu Tyr Leu Gln Pro Ser Ala Lys Arg Pro Asp Ala
            20                  25

<210> SEQ ID NO 4
<211> LENGTH: 24
<212> TYPE: PRT
<213> ORGANISM: Homo sapiens

<400> SEQUENCE: 4

Met Ala Ala Arg Gly Val Ile Ala Pro Val Gly Glu Ser Leu Arg Tyr
1               5                   10                  15

Ala Glu Tyr Leu Gln Pro Ser Ala
            20

<210> SEQ ID NO 5
<211> LENGTH: 18
<212> TYPE: PRT
<213> ORGANISM: Homo sapiens

<400> SEQUENCE: 5

Met Ala Ala Arg Gly Val Ile Ala Pro Val Gly Glu Ser Leu Arg Tyr
1               5                   10                  15

Ala Glu

<210> SEQ ID NO 6
```

```
<211> LENGTH: 18
<212> TYPE: PRT
<213> ORGANISM: Homo sapiens

<400> SEQUENCE: 6

Arg Gly Val Ile Ala Pro Val Gly Glu Ser Leu Arg Tyr Ala Glu Tyr
1               5                   10                  15

Leu Cys

<210> SEQ ID NO 7
<211> LENGTH: 13
<212> TYPE: PRT
<213> ORGANISM: Homo sapiens

<400> SEQUENCE: 7

Met Ala Ala Arg Gly Val Ile Ala Pro Val Gly Glu Ser
1               5                   10

<210> SEQ ID NO 8
<211> LENGTH: 19
<212> TYPE: PRT
<213> ORGANISM: Homo sapiens

<400> SEQUENCE: 8

Ala Ala Arg Gly Val Ile Ala Pro Val Gly Glu Ser Leu Arg Tyr Ala
1               5                   10                  15

Glu Tyr Leu

<210> SEQ ID NO 9
<211> LENGTH: 31
<212> TYPE: PRT
<213> ORGANISM: Homo sapiens

<400> SEQUENCE: 9

Met Ala Ala Arg Gly Val Ile Ala Pro Val Gly Glu Ser Leu Arg Tyr
1               5                   10                  15

Ala Glu Tyr Leu Gln Pro Ser Ala Lys Arg Pro Asp Ala Asp Val
                20                  25                  30

<210> SEQ ID NO 10
<211> LENGTH: 39
<212> TYPE: PRT
<213> ORGANISM: Homo sapiens

<400> SEQUENCE: 10

Met Ala Ala Arg Gly Val Ile Ala Pro Val Gly Glu Ser Leu Arg Tyr
1               5                   10                  15

Ala Glu Tyr Leu Gln Pro Ser Ala Lys Arg Pro Asp Ala Asp Val Asp
                20                  25                  30

Gln Gln Gly Leu Val Arg Ser
                35

<210> SEQ ID NO 11
<211> LENGTH: 36
<212> TYPE: PRT
<213> ORGANISM: Homo sapiens

<400> SEQUENCE: 11

Met Ala Ala Arg Gly Val Ile Ala Pro Val Gly Glu Ser Leu Arg Tyr
1               5                   10                  15

Ala Glu Tyr Leu Gln Pro Ser Ala Lys Arg Pro Asp Ala Asp Val Asp
                20                  25                  30
```

```
Gln Gln Gly Leu
        35

<210> SEQ ID NO 12
<211> LENGTH: 32
<212> TYPE: PRT
<213> ORGANISM: Homo sapiens

<400> SEQUENCE: 12

Met Ala Ala Arg Gly Val Ile Ala Pro Val Gly Glu Ser Leu Arg Tyr
1               5                   10                  15

Ala Glu Tyr Leu Gln Pro Ser Ala Lys Arg Pro Asp Ala Asp Val Asp
            20                  25                  30

<210> SEQ ID NO 13
<211> LENGTH: 25
<212> TYPE: PRT
<213> ORGANISM: Homo sapiens

<400> SEQUENCE: 13

Met Ala Ala Arg Gly Val Ile Ala Pro Val Gly Glu Ser Leu Arg Tyr
1               5                   10                  15

Ala Glu Tyr Leu Gln Pro Ser Ala Lys
            20                  25

<210> SEQ ID NO 14
<211> LENGTH: 30
<212> TYPE: PRT
<213> ORGANISM: Homo sapiens

<400> SEQUENCE: 14

Met Ala Ala Arg Gly Val Ile Ala Pro Val Gly Glu Ser Leu Arg Tyr
1               5                   10                  15

Ala Glu Tyr Leu Gln Pro Ser Ala Lys Arg Pro Asp Ala Asp
            20                  25                  30

<210> SEQ ID NO 15
<211> LENGTH: 45
<212> TYPE: PRT
<213> ORGANISM: Homo sapiens

<400> SEQUENCE: 15

Met Ala Ala Arg Gly Val Ile Ala Pro Val Gly Glu Ser Leu Arg Tyr
1               5                   10                  15

Ala Glu Tyr Leu Gln Pro Ser Ala Lys Arg Pro Asp Ala Asp Val Asp
            20                  25                  30

Gln Gln Gly Leu Val Arg Ser Leu Ile Ala Val Gly Leu
        35                  40                  45

<210> SEQ ID NO 16
<211> LENGTH: 22
<212> TYPE: PRT
<213> ORGANISM: Homo sapiens

<400> SEQUENCE: 16

Met Ala Ala Arg Gly Val Ile Ala Pro Val Gly Glu Ser Leu Arg Tyr
1               5                   10                  15

Ala Glu Tyr Leu Gln Pro
            20

<210> SEQ ID NO 17
<211> LENGTH: 26
<212> TYPE: PRT
```

<213> ORGANISM: Homo sapiens

<400> SEQUENCE: 17

Met Ala Ala Arg Gly Val Ile Ala Pro Val Gly Glu Ser Leu Arg Tyr
1               5                   10                  15

Ala Glu Tyr Leu Gln Pro Ser Ala Lys Arg
            20                  25

<210> SEQ ID NO 18
<211> LENGTH: 16
<212> TYPE: PRT
<213> ORGANISM: Homo sapiens

<400> SEQUENCE: 18

Gly Val Ile Ala Pro Val Gly Glu Ser Leu Arg Tyr Ala Glu Tyr Leu
1               5                   10                  15

<210> SEQ ID NO 19
<211> LENGTH: 18
<212> TYPE: PRT
<213> ORGANISM: Homo sapiens

<400> SEQUENCE: 19

Ala Arg Gly Val Ile Ala Pro Val Gly Glu Ser Leu Arg Tyr Ala Glu
1               5                   10                  15

Tyr Leu

<210> SEQ ID NO 20
<211> LENGTH: 15
<212> TYPE: PRT
<213> ORGANISM: Homo sapiens

<400> SEQUENCE: 20

Val Ile Ala Pro Val Gly Glu Ser Leu Arg Tyr Ala Glu Tyr Leu
1               5                   10                  15

<210> SEQ ID NO 21
<211> LENGTH: 64
<212> TYPE: DNA
<213> ORGANISM: Artificial Sequence
<220> FEATURE:
<223> OTHER INFORMATION: Synthetic Oligonucleotide

<400> SEQUENCE: 21
gatccccgaa gatttcaact cctagcttca agagagctag gagttgaaat cttcttttttg      60 gaag                                                                    64

<210> SEQ ID NO 22
<211> LENGTH: 29
<212> TYPE: DNA
<213> ORGANISM: Artificial Sequence
<220> FEATURE:
<223> OTHER INFORMATION: Synthetic Oligonucleotide

<400> SEQUENCE: 22
ccttgccagc agatgggctt acacctaaa                                         29

<210> SEQ ID NO 23
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 23

```
cagaaaatga gtaggcgaga agc                                              23
```

<210> SEQ ID NO 24
<211> LENGTH: 26
<212> TYPE: DNA
<213> ORGANISM: Artificial Sequence
<220> FEATURE:
<223> OTHER INFORMATION: Synthetic Oligonucleotide

<400> SEQUENCE: 24

```
tgactctcct atgagctgtt ctaatc                                           26
```

<210> SEQ ID NO 25
<211> LENGTH: 150
<212> TYPE: PRT
<213> ORGANISM: Homo sapiens

<400> SEQUENCE: 25

```
Met Ala Ala Arg Gly Val Ile Ala Pro Val Gly Glu Ser Leu Arg Tyr
1               5                   10                  15

Ala Glu Tyr Leu Gln Pro Ser Ala Lys Arg Pro Asp Ala Asp Val Asp
            20                  25                  30

Gln Gln Arg Leu Val Arg Ser Leu Ile Ala Val Gly Leu Gly Val Ala
        35                  40                  45

Ala Leu Ala Phe Ala Gly Arg Tyr Ala Phe Arg Ile Trp Lys Pro Leu
    50                  55                  60

Glu Gln Val Ile Thr Glu Thr Ala Lys Lys Ile Ser Thr Pro Ser Phe
65                  70                  75                  80

Ser Ser Tyr Tyr Lys Gly Gly Phe Glu Gln Lys Met Ser Arg Arg Glu
                85                  90                  95

Ala Gly Leu Ile Leu Gly Val Ser Pro Ser Ala Gly Lys Ala Lys Ile
            100                 105                 110

Arg Thr Ala His Arg Arg Val Met Ile Leu Asn His Pro Asp Lys Gly
        115                 120                 125

Gly Ser Pro Tyr Val Ala Ala Lys Ile Asn Glu Ala Lys Asp Leu Leu
    130                 135                 140

Glu Thr Thr Thr Lys His
145                 150
```

<210> SEQ ID NO 26
<211> LENGTH: 116
<212> TYPE: PRT
<213> ORGANISM: Homo sapiens

<400> SEQUENCE: 26

```
Met Ala Ser Thr Val Val Ala Val Gly Leu Thr Ile Ala Ala Ala Gly
1               5                   10                  15

Phe Ala Gly Arg Tyr Val Leu Gln Ala Met Lys His Met Glu Pro Gln
            20                  25                  30

Val Lys Gln Val Phe Gln Ser Leu Pro Lys Ser Ala Phe Ser Gly Gly
        35                  40                  45

Tyr Tyr Arg Gly Gly Phe Glu Pro Lys Met Thr Lys Arg Glu Ala Ala
    50                  55                  60

Leu Ile Leu Gly Val Ser Pro Thr Ala Asn Lys Gly Lys Ile Arg Asp
65                  70                  75                  80

Ala His Arg Arg Ile Met Leu Leu Asn His Pro Asp Lys Gly Gly Ser
                85                  90                  95

Pro Tyr Ile Ala Ala Lys Ile Asn Glu Ala Lys Asp Leu Leu Glu Gly
```

Gln Ala Lys Lys
        115

<210> SEQ ID NO 27
<211> LENGTH: 118
<212> TYPE: PRT
<213> ORGANISM: Drosophila melanogaster

<400> SEQUENCE: 27

Met Ala Ser Ser Val Ile Leu Ala Gly Leu Ser Val Ala Ala Val Gly
1               5                   10                  15

Phe Ala Gly Lys His Leu Met Arg Arg Met Pro Gln Met Thr Thr Lys
            20                  25                  30

Phe Asn Glu Ala Leu Lys Asn Leu Pro Lys Tyr Asp Ala Glu Ser Met
        35                  40                  45

Ala Ala Ser Lys Tyr Tyr Lys Gly Gly Phe Asp Pro Lys Met Asn Lys
    50                  55                  60

Arg Glu Ala Ser Leu Ile Leu Gly Val Ser Pro Ser Ala Ser Lys Ile
65                  70                  75                  80

Lys Ile Lys Asp Ala His Lys Lys Ile Met Leu Leu Asn His Pro Asp
                85                  90                  95

Arg Gly Gly Ser Pro Tyr Leu Ala Ala Lys Ile Asn Glu Ala Lys Asp
            100                 105                 110

Phe Leu Asp Lys Ala Lys
        115

<210> SEQ ID NO 28
<211> LENGTH: 112
<212> TYPE: PRT
<213> ORGANISM: Arabidopsis thaliana

<400> SEQUENCE: 28

Met Ala Thr Pro Met Ile Ala Gly Ala Ala Val Ala Ala Ala Ala Val
1               5                   10                  15

Ala Gly Arg Tyr Gly Ile Leu Ala Trp Gln Ala Phe Lys Ala Arg Pro
            20                  25                  30

Arg Val Pro Arg Met Arg Arg Phe Tyr Glu Gly Gly Phe Gln Ser Ser
        35                  40                  45

Met Thr Arg Arg Glu Ala Ala Leu Ile Leu Gly Val Arg Glu Ser Val
    50                  55                  60

Val Ala Asp Lys Val Lys Glu Ala His Arg Arg Val Met Val Ala Asn
65                  70                  75                  80

His Pro Asp Ala Gly Gly Ser His Tyr Leu Ala Ser Lys Ile Asn Glu
                85                  90                  95

Ala Lys Asp Met Met Leu Gly Lys Ser Asn Asn Ser Gly Ser Ala Phe
            100                 105                 110

<210> SEQ ID NO 29
<211> LENGTH: 113
<212> TYPE: PRT
<213> ORGANISM: Dictyostelium discoideum

<400> SEQUENCE: 29

Met Ala Thr Pro Ile Ile Val Gly Ala Thr Ile Ala Gly Ile Ala Tyr
1               5                   10                  15

Ser Ser Arg Phe Leu Ile Arg Val Ile Gln Arg Ala Lys Ser Lys Gln
            20                  25                  30

```
Leu Phe Glu Met Val Ser Thr Pro Gly Phe Thr Val Glu Thr Ile Glu
             35                  40                  45

Asp Gly Phe Glu Asn Lys Met Thr Pro Ala Glu Ala Asn Ile Leu
 50                  55                  60

Gly Leu Lys Glu Ser Thr Lys Glu Ile Lys Ile Arg His Lys
 65                  70                  75                  80

Leu Leu Met Ile Lys Asn His Pro Asp Lys Gly Gly Ser Ser Tyr Leu
                 85                  90                  95

Ala Thr Lys Ile Asn Glu Ala Arg Asn Val Leu Ser Ser Lys Asn Ser
            100                 105                 110

Asn

<210> SEQ ID NO 30
<211> LENGTH: 105
<212> TYPE: PRT
<213> ORGANISM: Emericella nidulans

<400> SEQUENCE: 30

Met Ala Ser Ala Leu Thr Leu Gly Leu Gly Val Ala Thr Ala Ala Phe
 1               5                  10                  15

Leu Gly Arg Ala Gly Leu Val Ala Tyr Arg Arg Ser Lys Gly Gly Val
             20                  25                  30

Asn Ala Leu Gly Lys Ala Phe Tyr Lys Gly Gly Phe Glu Pro Arg Met
             35                  40                  45

Asn Arg Arg Glu Ala Ala Leu Ile Leu Glu Leu Pro Glu Arg Thr Leu
 50                  55                  60

Asn Lys Glu Lys Val Arg Lys Lys His Arg Gln Leu Met Leu Leu Asn
 65                  70                  75                  80

His Pro Asp Arg Gly Gly Ser Pro Tyr Leu Ala Thr Lys Ile Asn Glu
                 85                  90                  95

Ala Lys Glu Phe Leu Asp Lys His Thr
            100                 105

<210> SEQ ID NO 31
<211> LENGTH: 112
<212> TYPE: PRT
<213> ORGANISM: Caenorhabditis elegans

<400> SEQUENCE: 31

Met Thr Gly Gly Leu Ile Val Ala Gly Leu Gly Leu Ala Ala Val Gly
 1               5                  10                  15

Phe Gly Ala Arg Tyr Val Leu Arg Asn Gln Ala Leu Ile Lys Lys Gly
             20                  25                  30

Met Glu Ala Ile Pro Val Ala Gly Gly Ala Phe Ser Asn Tyr Tyr Arg
             35                  40                  45

Gly Gly Phe Asp Gln Lys Met Ser Arg Ala Glu Ala Ala Lys Ile Leu
 50                  55                  60

Gly Val Ala Pro Ser Ala Lys Pro Ala Lys Ile Lys Glu Ala His Lys
 65                  70                  75                  80

Lys Val Met Ile Val Asn His Pro Asp Arg Gly Gly Ser Pro Tyr Leu
                 85                  90                  95

Ala Ala Lys Ile Asn Glu Ala Lys Asp Leu Met Glu Ser Ser Lys Ser
            100                 105                 110

<210> SEQ ID NO 32
<211> LENGTH: 146
<212> TYPE: PRT
<213> ORGANISM: Saccharomyces cerevisiae
```

```
<400> SEQUENCE: 32

Met Val Leu Pro Ile Ile Gly Leu Gly Val Thr Met Val Ala Leu
1               5                   10                  15

Ser Val Lys Ser Gly Leu Asn Ala Trp Thr Val Tyr Lys Thr Leu Ser
            20                  25                  30

Pro Leu Thr Ile Ala Lys Leu Asn Asn Ile Arg Ile Glu Asn Pro Thr
        35                  40                  45

Ala Gly Tyr Arg Asp Ala Leu Lys Phe Lys Ser Ser Leu Ile Asp Glu
    50                  55                  60

Glu Leu Lys Asn Arg Leu Asn Gln Tyr Gln Gly Gly Phe Ala Pro Arg
65                  70                  75                  80

Met Thr Glu Pro Glu Ala Leu Leu Ile Leu Asp Ile Ser Ala Arg Glu
                85                  90                  95

Ile Asn His Leu Asp Glu Lys Leu Leu Lys Lys His Arg Lys Ala
            100                 105                 110

Met Val Arg Asn His Pro Asp Arg Gly Gly Ser Pro Tyr Met Ala Ala
        115                 120                 125

Lys Ile Asn Glu Ala Lys Glu Val Leu Glu Arg Ser Val Leu Leu Arg
    130                 135                 140

Lys Arg
145

<210> SEQ ID NO 33
<211> LENGTH: 168
<212> TYPE: PRT
<213> ORGANISM: Saccharomyces cerevisiae

<400> SEQUENCE: 33

Met Ser Ser Gln Ser Asn Thr Gly Asn Ser Ile Glu Ala Pro Gln Leu
1               5                   10                  15

Pro Ile Pro Gly Gln Thr Asn Gly Ser Ala Asn Val Thr Val Asp Gly
            20                  25                  30

Ala Gly Val Asn Val Gly Ile Gln Asn Gly Ser Gln Gly Gln Lys Thr
        35                  40                  45

Gly Met Asp Leu Tyr Phe Asp Gln Ala Leu Asn Tyr Met Gly Glu His
    50                  55                  60

Pro Val Ile Thr Gly Phe Gly Ala Phe Leu Thr Leu Tyr Phe Thr Ala
65                  70                  75                  80

Gly Ala Tyr Lys Ser Ile Ser Lys Gly Leu Asn Gly Gly Lys Ser Thr
                85                  90                  95

Thr Ala Phe Leu Lys Gly Gly Phe Asp Pro Lys Met Asn Ser Lys Glu
            100                 105                 110

Ala Leu Gln Ile Leu Asn Leu Thr Glu Asn Thr Leu Thr Lys Lys Lys
        115                 120                 125

Leu Lys Glu Val His Arg Lys Ile Met Leu Ala Asn His Pro Asp Lys
    130                 135                 140

Gly Gly Ser Pro Phe Leu Ala Thr Lys Ile Asn Glu Ala Lys Asp Phe
145                 150                 155                 160

Leu Glu Lys Arg Gly Ile Ser Lys
                165
```